(12) United States Patent
Dharmakumar et al.

(10) Patent No.: US 11,690,524 B2
(45) Date of Patent: *Jul. 4, 2023

(54) ASSESSMENT OF IRON DEPOSITION POST MYOCARDIAL INFARCTION AS A MARKER OF MYOCARDIAL HEMORRHAGE

(71) Applicant: Cedars-Sinai Medical Center, Los Angeles, CA (US)

(72) Inventors: Rohan Dharmakumar, Moorpark, CA (US); Ivan Cokic, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 131 days.

This patent is subject to a terminal disclaimer.

(21) Appl. No.: 16/905,702

(22) Filed: Jun. 18, 2020

(65) Prior Publication Data

US 2020/0315468 A1 Oct. 8, 2020

Related U.S. Application Data

(63) Continuation of application No. 15/064,817, filed on Mar. 9, 2016, now Pat. No. 10,694,962, which is a continuation-in-part of application No. 14/125,307, filed as application No. PCT/US2012/042310 on Jun. 13, 2012, now Pat. No. 10,694,961.

(60) Provisional application No. 61/496,441, filed on Jun. 13, 2011.

(51) Int. Cl.
| | |
|---|---|
| A61K 9/127 | (2006.01) |
| A61B 5/026 | (2006.01) |
| A61B 5/00 | (2006.01) |
| G16H 50/30 | (2018.01) |
| G16H 20/10 | (2018.01) |
| G16H 30/40 | (2018.01) |
| A61K 49/06 | (2006.01) |

(52) U.S. Cl.
CPC .......... *A61B 5/0263* (2013.01); *A61B 5/0044* (2013.01); *A61B 5/4848* (2013.01); *A61B 5/7275* (2013.01); *G16H 20/10* (2018.01); *G16H 50/30* (2018.01); *A61K 49/06* (2013.01); *G16H 30/40* (2018.01); *Y02A 90/10* (2018.01)

(58) Field of Classification Search
CPC ... A61B 5/0263; A61B 5/0044; A61B 5/4848; A61B 5/7275; G16H 20/10; G16H 50/30; G16H 30/40; A61K 49/06; Y02A 90/10
See application file for complete search history.

(56) References Cited

U.S. PATENT DOCUMENTS

| | | | |
|---|---|---|---|
| 5,013,718 A | 5/1991 | Adamson et al. | |
| 5,162,313 A | 11/1992 | Kappas et al. | |
| 2002/0045573 A1 | 4/2002 | Lai | |
| 2006/0051806 A1 | 3/2006 | Rothenberg et al. | |
| 2011/0044524 A1 | 2/2011 | Wang et al. | |
| 2011/0105575 A1 | 5/2011 | Nick et al. | |
| 2012/0263362 A1 | 10/2012 | McAuley et al. | |
| 2014/0113008 A1 | 4/2014 | Dharmakumar et al. | |
| 2014/0314676 A1 | 10/2014 | Spino et al. | |
| 2016/0183815 A1 | 6/2016 | Dharmakumar et al. | |
| 2020/0315456 A1 | 10/2020 | Dharmakumar et al. | |

FOREIGN PATENT DOCUMENTS

| | | |
|---|---|---|
| WO | 2012/174157 A1 | 12/2012 |
| WO | 2021087344 A1 | 5/2021 |
| WO | 2021188984 A1 | 9/2021 |

OTHER PUBLICATIONS

Salu et al. (Cardiovasc. Res. 2006, 69, 536-544).*
Williams et al. (Circulation 1991,83, 1006-1014).*
Stenestrand et al. (JAMA 2001, 285, 430-436).*
PCT/U2012/042310 International Search Report and Written Opinion dated Aug. 27, 2012, 10 pages.
PCT/US2012/042310 International Preliminary Report on Patentability dated Dec. 17, 2013, 8 pages.
Anderson et al., Cardiovascular T2-star (T2*) magnetic resonance for the early diagnosis of myocardial iron overload, European Heart Journal, 2001, vol. 22, 2171-2179.
Aronow et al., Atrioventricular Block in Familial Hemochromatosis Treated by Permanent Synchronus Pacemaker, Arch Intern Med, 1969, vol. 123, p. 433.
Bongartz, L., The Severe Cardiorenal Syndrome, Doctoral Dissertation, Utrecht University, 2011.
Bulluck et al., Cardiovascular Magnetic Resonance in Acute ST-Segment-Elevation Myocardial Infarction, 2018, Circulation, vol. 137(18), pp. 1949-1964.
Chan et al., Effect of Iron Chelation on Myocardial Infarct Size and Oxidative Stress in ST-Elevation-Myocardial Infarction, 2012, Circ. Cardiovasc Interv., vol. 5(2), pp. 270-278.
Chatterjee et al., Hemodynamic and Metabolic Responses to Vasodilator Therapy in Acute Myocardial Infarction, Circulation, 1973, vol. 48, pp. 1183-1193.

(Continued)

*Primary Examiner* — Michael G. Hartley
*Assistant Examiner* — Melissa J Perreira
(74) *Attorney, Agent, or Firm* — Nixon Peabody LLP; Linda B. Huber; Suwei Zhu

(57) ABSTRACT

The invention provides various methods of identifying myocardial infarction (MI) patients who have microvascular obstruction (MO), persistent microvascular obstruction (PMO), reperfusion hemorrhage, iron deposition, chronic iron deposition, and/or fat infiltration/accumulation. The invention provides various methods of identifying myocardial infarction (MI) patients who are at risk of prolonged inflammation burden in heart, adverse cardiac remodeling, electrical abnormality, mechanical abnormality, malignant cardiac arrhythmia, ischemic heart failure, and/or sudden cardiac death. The invention also provides various methods of treating these MI patients with chelation drugs, anti-inflammatory drugs, fat-lowering drugs, cooling therapies, or device therapies, or their combinations.

18 Claims, 30 Drawing Sheets
(16 of 30 Drawing Sheet(s) Filed in Color)

(56) References Cited

OTHER PUBLICATIONS

Chevion et al., Copper and Iron are Mobilized Following Myocardial Ischemia: Possible Predictive Criteria for Tissue Injury, Proc. Natl. Acad. Sci. USA, 1993, vol. 90, pp. 1102-1106.

Cokic et al., Iron Deposition following Chronic Myocardial Infarction as a Substrate for Cardiac Electrical Anomalies Initial Findings in a Canine Model, PLoS ONE, 2013, 8(9), e73193, pp. 1-11.

Dharmakumar R., "Rusty hearts": is it time to rethink iron chelation therapies in post-myocardial-infarction setting?, Circ. Cardiovasc. Imaging., 2016, vol. 9(10), 3 Pages. Originally published Oct. 10, 2016.

Ellervik et al., Hereditary Hemochromatosis Genotypes and Risk of Ischemic Stroke, Neurology, 2007, vol. 68, pp. 1025-1031.

Fishbein et al., The Histopathologic Evolution of Myocardial Infarction, Chest, 1978, vol. 73, pp. 843-849.

Foltz et al., MRI Relaxation Fluctuations in Acute Reperfused Hemorrhagic Infarction, 2006, Magnetic Resonance in Medicine, vol. 56, pp. 1311-1319.

Ganame et al., Impact of Myocardial Haemorrhage on Left Ventricular Function and Remodelling in Patients with Reperfused Acute Myocardial Infarction, European Heart Journal 2009, vol. 30, pp. 1440-1449.

Ghugre et al., Quantitative Tracking of Edema, Hemorrhage, and Microvascular Obstruction in Subacute Myocardial Infarction in a Porcine Model by MRI, Mag. Reson. Med 2011, 66, pp. 1129-1141.

Goldfarb et al., Myocardial Fat Deposition after Left Ventricular Myocardial Infarction: Assessment by Using MR Water-Fat Separation Imaging, Radiology, 2009, vol. 253(1), pp. 65-73.

Google Scholar Search for "Hemosiderin Infarct", 2019.

Merriam-Webster Medical Definition of "Hemosiderin", 2019.

Horowitz et al., Iron-mediated cardiovascular injury, Vasc. Med. 1999, vol. 4, pp. 93-99.

Jugdutt et al., Salvage of Ischemic Myocardium by ibuprofen during Infarction in the Conscious Dog, The American Journal of Cardiology, 1980, vol. 46, pp. 74-82.

Kali et al., Chronic Manifestation of Postreperfusion Intramyocardial Hemorrhage as Regional Iron Deposition: A Cardiovascular Magnetic Resonance Study With Ex Vivo Validation, Circ. Cardiovasc. Imaging., 2013, pp. 218-228 and Supplemental Materials, pp. 1-17.

Kamat et al., Dexrazoxane Shows No Protective Effect in the Acute Phase of Reperfusion during Myocardial Infarction in Pigs, 2016, PloS One, vol. 11(12), 14 Pages.

Klipsein-Grobusch et al., Dietary Iron and Risk of Myocardial Infarction in the Rotterdam Study, Am. J. Epidem. 1999, vol. 149, pp. 421-428.

Kloner, Current State of Clinical Translation of Cardioprotective Agents for Acute Myocardial Infarction, Circulation Research, 2013, vol. 113(4), pp. 451-463.

Lakkisto et al., Heme oxygenase-1 and carbon monoxide promote neovascularization after myocardial infarction by modulating the expression of HIF-1a, SDF-1a and VEGF-B, E. J. Pharmacol. 2010, vol. 635, pp. 156-164.

Lesnefsky et al., Deferoxamine Pretreatment Reduces Canine Infarct Size and Oxidavit Injury, The Journal of Pharmacology and Experimental Therapeutics, 1990, vol. 253(3), pp. 1103-1109.

Lewis, H.P., Cardiac Involvement in Hemochromatosis, Trans Am clin Climatol Assoc, 1954, vol. 65, pp. 49-76.

Ono et al., Nicorandil Improves Cardiac Function and Clinical Outcome in Patients with acute Myocardial Infarction Undergoing Primary Percutaneous Coronary Intervention: Role of Inhibitory Effect on Reactive Oxygen Species Formation, American Heart Journal, 2004, vol. 148(4), pp. 1-7.

D'Regan et al., Reperfusion Hemorrhage Following Acute Myocardial Infarction: Assessment with T2* Mapping and Effect on Measuring the Area of Risk, Radiology, 2009, vol. 250, pp. 916-922.

Smith et al., Hemopexin and Haptoglobin: Allies Against Heme Toxicity from Hemoglobin not Contenders, 2015, Front Physiol, vol. 6, Article 187, 20 Pages.

Stenestrand et al., Early Statin Treatment Following Acute Myocardial Infarction and 1-Year Survival, JAMA, 2001, vol. 285(4), pp. 430-436.

Sullivan et al., Do Hemochromatosis Mutations Protect Against Iron-Mediated Atherogenesis, Circ. Cardiovasc. Genet. 2009, vol. 2, pp. 653-657.

Tuomainen et al., Increased Risk of Acute Myocardial Infarction in Carriers of the Hemochromatiosis Gene Cys282Tyr Mutation, Circulation, 1999, vol. 100, pp. 1274-1279.

Voogd et al., Low Molecular Weight Iron and the Oxygen Paradox in Isolated Rat Hearts, J. Clin Invest., 1992, vol. 90, pp. 2050-2055.

Waxman et al., Myocardial Involvement in Primary Hemochromatosis Demonstrated by Magnetic Resonance Imaging, Am. Heart J., 1994, vol. 128, pp. 1047-1049.

Weidler, D. J., Myocardial Damage and Cardiac Arrhythmias After Intracranial Hemorrhage, A Critical Review, Stroke, 1974, vol. 5, pp. 759-764.

Tardif et al., Efficacy and Safety of Low-Dose Colchicine The New England Journal of Medicine, 2019, vol. 381(26), pp. 2497-2505.

Neckar et al., Protective effects of dexrazoxane against acute ischaemia/referpusion injury of rat hearts, Canadian Journal of Physiology and Pharmacology, 2012, vol. 90(9), pp. 1303-1310.

International Search Report and Written Opinion for PCT/US2020/58335 dated Jan. 19, 2021, 9 pages.

He et al., Deferoxamine inhibits microglial activation, attenuates blood-brain barrier disruption, rescues denritic damage, and improves spatial memory in a mouse model of microhemorrhages, J. Neurochem, 2016, vol. 183(3), pp. 436-447.

International Search Report and Written Opinion for PCT/US2021/23292, dated Jul. 8, 2021, 9 pages.

Behrouzi et al., Action of iron chelator on intramyocardial hemorrhage and cardiac remodeling following acute myocardial infarction, Basic Research in Cardiology, 2020, vol. 115(24), pp. 1-18.

Betgem et al., Intramyocardial haemorrhage after acute myocardial infarction, Nature Reviews Cardiology, 2014, pp. 1-12.

NIH Reporter, Mechanistic Insights to A Translatable Therapy for Acute Reperfused Hemorrhagic Myocardial Infarctions, Award Notice Date: Mar. 5, 2020, Award No. 1R01HL147133-01A1.

Wilk et al., Hybrid PET/MR imaging in myocardial inflammation post-myocardial infarction, J. Nucl. Cardiol., 2020, vol. 27(6), pp. 2083-2099.

Nair et al., Reperfused hemorrhagic myocardial infarction in rats, PLOS ONE, 2020, pp. 1-15.

Guan et al., Assessment of intramyocardial hemorrhage with dark-blood T2*-weighted cardiovascular magnetic resonance, Journal of Cardiovascular Magnetic Resonance, 2021, vol. 23(88), pp. 1-15.

NIH Reporter, Developing a MRI-guided Disease-Modifying Therapy for Post Infarction Chronic Heart Failure, Award Notice Date: Award Notice Date: Jun. 30, 2017, Award No. 1R01HL133407-01A1.

Liu et al., Intramyocardial Hemorrhage and the "Wave Front" of Reperfusion Injury Compromising Myocardial Salvage, Journal of the American College of Cardiology, 2022, vol. 79(1), pp. 35-48, Abstract.

Malliaras et al., Validation of Contrast-Enhanced Magnetic Resonance Imaging to Monitor Regenerative Efficacy After Cell Therapy in a Porcine Model of Convalescent Myocardial Infarction, Molecular Cardiology, 2013, retrieved from the Internet: https://www.ahajournals.org/doi/epdf/10.1161/CIRCULATIONAHA.113.002863.

Ishizaka et al., Iron Chelation Suppresses Ferritin Upregulation and Attenuates Vascular Dysfunction in the Aorta of Angiotensin II-Infused Rats, Arterioscler Thromb Vas Biol., 2005, vol. 25, pp. 2282-2288.

Kell, Iron behaving badly: inappropriate iron chelation as a major contributor to the aetiology of vascular and other progressive inflammatory and degenerative diseases, BMC Medical Genomics, 2009, vol. 2(2), pp. 1-79.

\* cited by examiner

FIG. 5A
T2*-weighted Image
FIG. 5B
LGE
7 Day
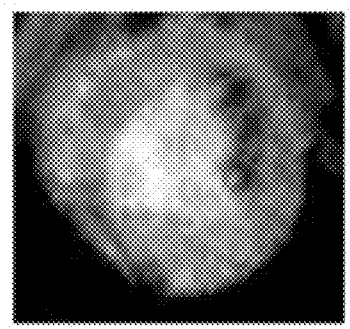 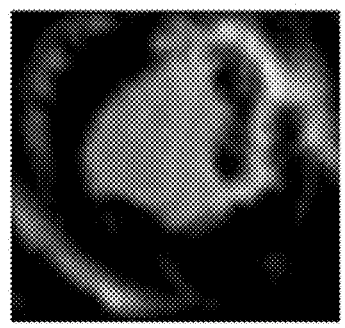
FIG. 5C
FIG. 5D
3 months
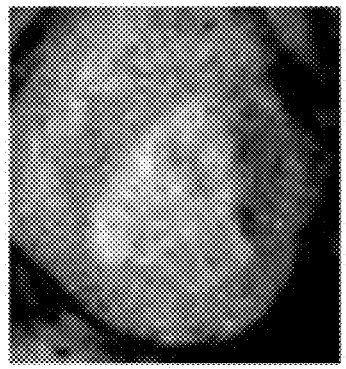 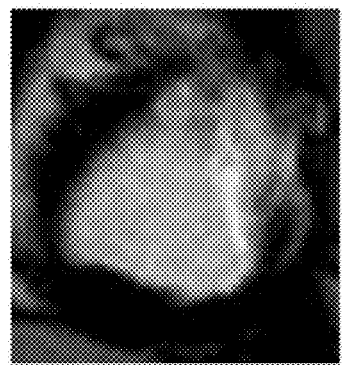
FIG. 5E
TTC Image
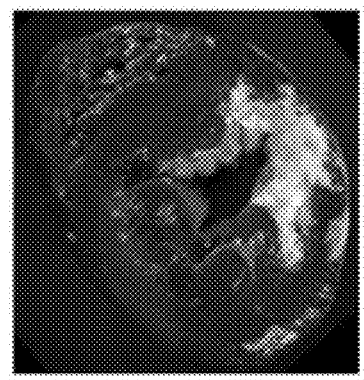

FIG. 6A

Relationship between normalized permittivity and [Fe]

| Normalized Permittivity | Coefficient | Standard Error | Z | P>Z | Lower 95% CI | Upper 95% CI |
|---|---|---|---|---|---|---|
| [Fe] in mg/g of tissue | 1.34 | 0.31 | 4.33 | <0.001 | 0.73 | 1.95 |
| Constant | 0.94 | 0.10 | 9.30 | <0.001 | 0.74 | 1.13 |

FIG. 6B

Relationship between normalized conductivity and [Fe]

| Normalized Conductivity | Coefficient | Standard Error | Z | P>Z | Lower 95% CI | Upper 95% CI |
|---|---|---|---|---|---|---|
| [Fe] in mg/g of tissue | 0.23 | 0.24 | 0.96 | 0.337 | -0.24 | 0.71 |
| Constant | 0.86 | 0.09 | 9.97 | <0.001 | 0.69 | 1.02 |

FIG. 6E

Relationship between normalized permittivity and Log (T2*)

| Normalized Permittivity | Coefficient | Standard Error | Z | P>Z | Lower 95% CI | Upper 95% CI |
|---|---|---|---|---|---|---|
| Log(T2*) | -0.65 | 0.28 | -2.37 | 0.018 | -1.20 | -0.11 |
| Constant | 0.86 | 0.09 | 3.72 | <0.001 | 1.47 | 4.76 |

FIG. 6F

Relationship between normalized conductivity and Log (T2*)

| Normalized Conductivity | Coefficient | Standard Error | Z | P>Z | Lower 95% CI | Upper 95% CI |
|---|---|---|---|---|---|---|
| Log(T2*) | -0.25 | 0.24 | -1.06 | 0.29 | -0.73 | 0.22 |
| Constant | 1.74 | 0.72 | 2.42 | 0.02 | 0.33 | 3.16 |

FIG. 11A    FIG. 11B
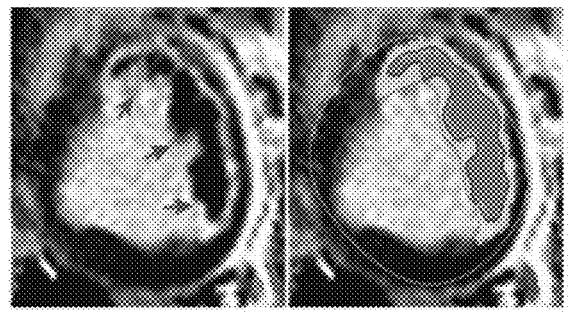
FIG. 11C    FIG. 11D    FIG. 11E
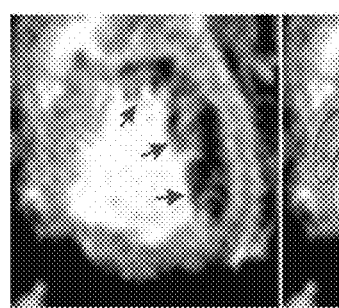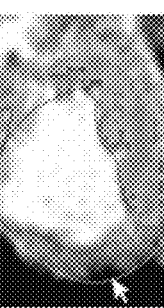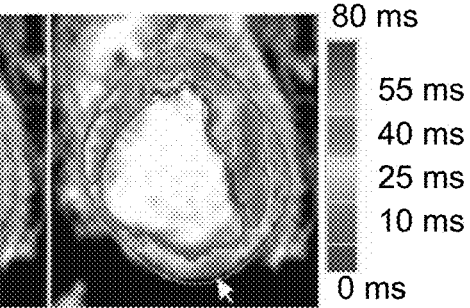
FIG. 12
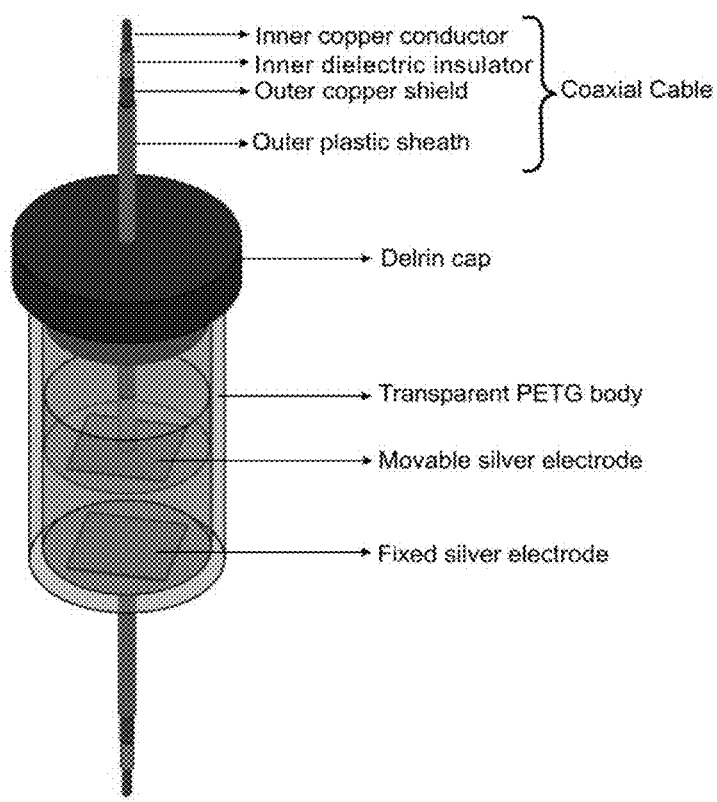

REPERFUSED MI

Infarct Volume

PMO Volume

Iron Volume

PMO vs. Iron

NON-REPERFUSED MI

Infarct Volume

NR-PMO Volume

Iron Volume

Iron Volume vs. NR-PMO Volume

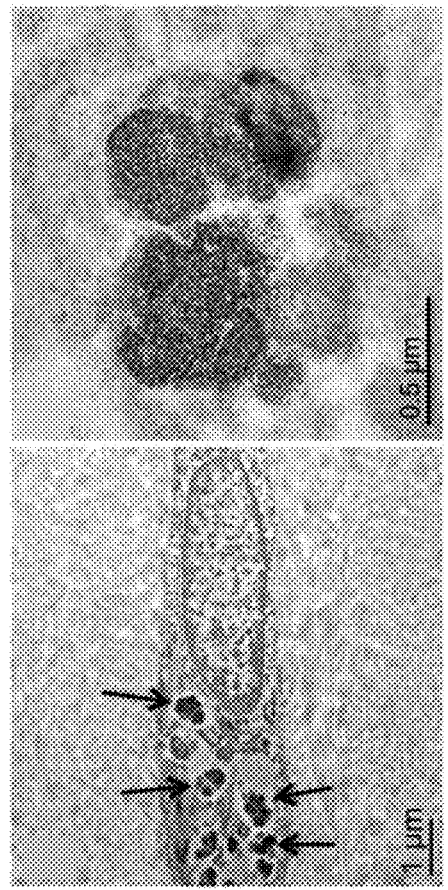
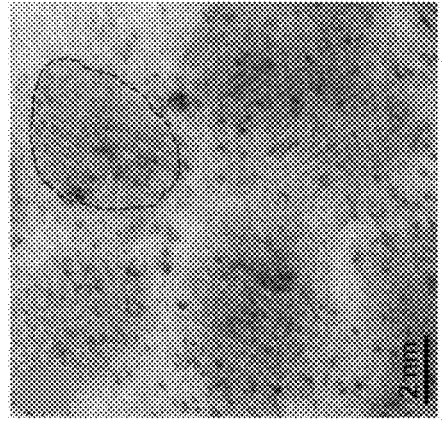
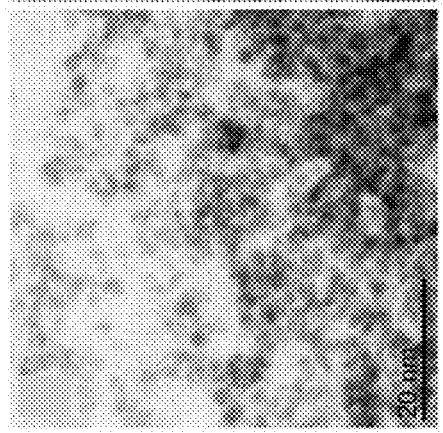
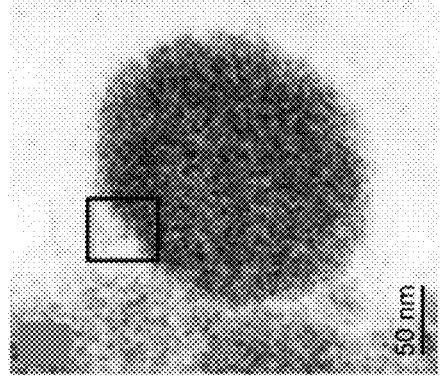
FIG. 25A  FIG. 25B  FIG. 25C  FIG. 25D  FIG. 25E

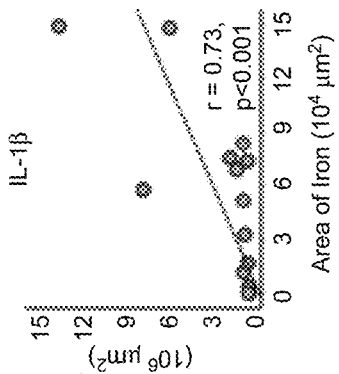
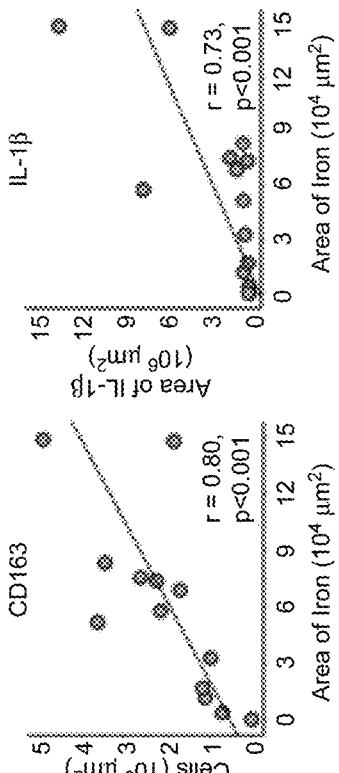
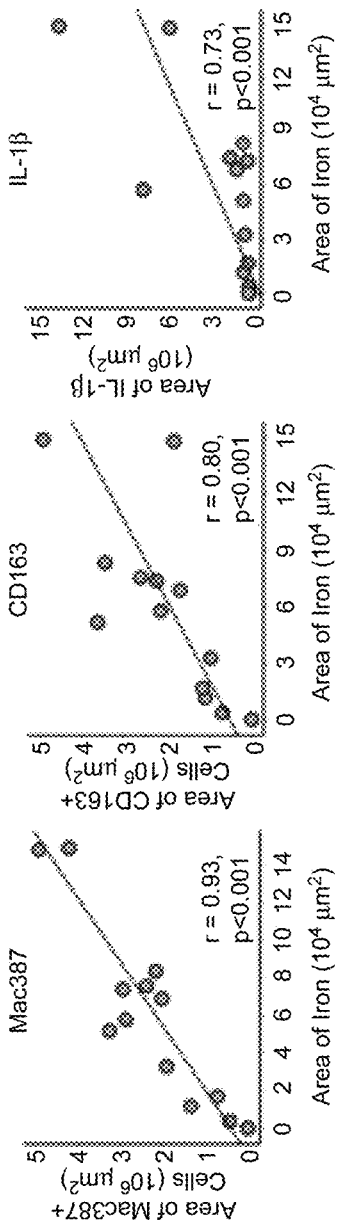
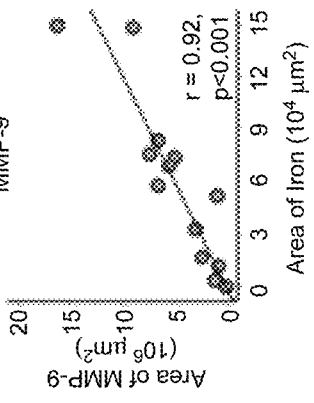
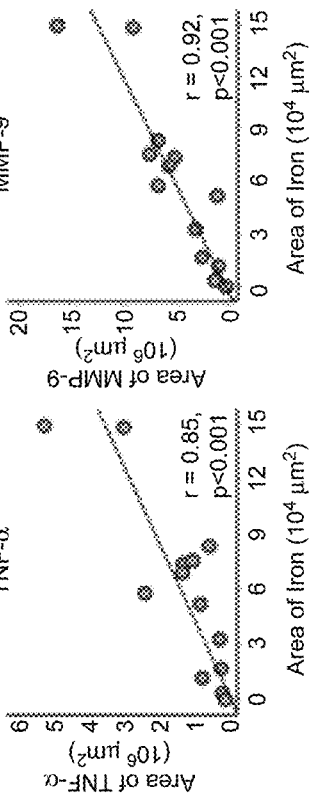
FIG. 27B  FIG. 27C  FIG. 27D
FIG. 27E  FIG. 27F

REPERFUSED MI

NON-REPERFUSED MI

REPERFUSED MI

NON-REPERFUSED MI

ASSESSMENT OF IRON DEPOSITION POST MYOCARDIAL INFARCTION AS A MARKER OF MYOCARDIAL HEMORRHAGE

This application is a continuation of U.S. patent application Ser. No. 15/064,817, filed Mar. 9, 2016, which is a continuation-in-part of U.S. patent application Ser. No. 14/125,307, filed on Dec. 10, 2013, which is the National Phase of International Application PCT/US2012/042310, filed on Jun. 13, 2012, which designated the U.S., was published under PCT Article 21(2) in English, and claims priority under 35 U.S.C. § 119(e) to U.S. provisional patent application No. 61/496,441, filed on Jun. 13, 2011. The contents of all the related applications cross-referenced herein are herein incorporated by reference in their entirety as though fully set forth.

STATEMENT REGARDING FEDERALLY SPONSORED RESEARCH OR DEVELOPMENT

This invention was made with government support under Grant No. HL091989 awarded by the National Institutes of Health. The government has certain rights in the invention.

FIELD OF INVENTION

The invention is directed to methods for diagnosing reperfusion and non-reperfusion hemorrhage, predicting cardiac arrhythmias, sudden cardiac death, and adverse remodeling in subjects post myocardial infarction. The invention also provides treatment methods for subjects at increased risk of sudden cardiac death and heart failure.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Significant narrowing of epicardial coronary arteries due to atherosclerotic disease or acute embolic obstruction can impede blood flow and oxygen to the myocardium resulting in acute myocardial infarction (AMI). Reperfusion therapy is the standard of care for restoring blood flow to the ischemic myocardial tissue. However, reperfusion therapies are also associated with post-infarct complications that are often associated with fatal heart failure. Most heart failures have an origin in ischemic heart disease and fatalities from it are largely related to Sudden Cardiac Death (SCD). In majority of cases, SCD is triggered by the onset of cardiac arrhythmias, an abnormally rapid heart rate originating in the ventricle and/or atria. If undetected and untreated, this can degenerate into asystole leading to hemodynamic impairment causing death.

Although there are diagnostic and therapeutic strategies for managing and treating ischemic heart disease, these strategies have limited value for distinguishing individual patients at risk for arrhythmias and SCD. The symptoms of ventricular arrhythmias (VA) are palpitations, chest pain, presyncope and syncope. In post-myocardial infarction patients or patients with VA symptoms, a 12-lead ECG, Holter monitoring and loop recorders are used to detect cardiac arrhythmias. However, there are no diagnostic strategies for predicting SCD before the onset of symptoms accompanying cardiac arrhythmias.

The spectrum of therapies also has limited benefits. Anti-arrhythmic drugs are frequently prescribed to suppress potential cardiac arrhythmia triggers, but most patients experience serious side effects and more than 40% of patients experience sustained VA recurrence within two years of starting the therapy. Moreover, a majority of anti-arrhythmia medications have pro-arrhythmic potential in patients with structural heart disease, thus, the current ACC (American College of Cardiology) guidelines recommend that antiarrhythmic drugs other than β-blockers should not be used to treat VA unless the patient is protected by an implantable cardioverter-defibrillator (ICD). Cardioversion by shock therapy can be achieved by external electrical defibrillation or internally via an ICD that continuously monitors for and detects episodes of VA. However, ICD therapy is a non-curative approach for patients with VA. It is associated with significantly decreased quality of life associated with VA symptoms and distress of anticipating ICD activation. Radiofrequency ablation offers a potential curative therapy, however the major challenge is the identification of the location of the VA substrate.

Reperfusion hemorrhage is a common consequence of re-establishing epicardial blood flow into severely ischemic myocardium. To date, the long-term effects of hemorrhagic infarcts on electrical conduction in the heart have not been studied. The inventor demonstrates that reperfusion and non-reperfusion hemorrhage leads to deposition of iron particulates within chronic infarcts and examines their role in mediating cardiac arrhythmias (abnormal and rapid beating of heart originating in the ventricle).

SUMMARY OF THE INVENTION

The invention provides a method for diagnosing reperfusion and non-reperfusion hemorrhage in a subject in need thereof comprising obtaining MRI images of the subject's heart, detecting regional iron oxide deposition in the heart, and diagnosing presence or absence of hemorrhage in the subject, wherein presence of iron oxide deposition in regions of the heart is indicative of hemorrhage in the subject, thereby diagnosing hemorrhage in the subject.

The invention is also directed to a method for predicting cardiac arrhythmias in a subject in need thereof comprising diagnosing hemorrhage in the subject by the method described above, wherein presence of hemorrhage is indicative of increased likelihood of cardiac arrhythmias in the subject, thereby predicting cardiac arrhythmias in the subject.

The invention is further directed to a method for predicting sudden cardiac death in a subject in need thereof comprising predicting cardiac arrhythmias by the method described above, wherein increased likelihood of cardiac arrhythmias is indicative of increased likelihood of sudden cardiac death in the subject, thereby predicting sudden cardiac death in the subject.

The invention also provides a method for treating a subject at an increased risk of sudden cardiac death or heart failure associated with regional iron deposition in the heart comprising administering to the subject an effective amount of a chelating agent, so as to treating the subject at an increased risk of sudden cardiac death associated with regional iron deposition in the heart.

The invention further provides a method for determining the prognosis after a myocardial infarction in a subject in need thereof comprising diagnosing reperfusion hemorrhage in the subject by the method described above, wherein the presence of reperfusion and non-reperfusion hemorrhage in the subject is indicative of a poor prognosis, thereby determining the prognosis of a myocardial infarction in the subject.

BRIEF DESCRIPTION OF FIGURES

The patent or application file contains at least one drawing executed in color. Copies of this patent or patent application publication with color drawing(s) will be provided by the Office upon request and payment of the necessary fee.

Exemplary embodiments are illustrated in referenced figures. It is intended that the embodiments and figures disclosed herein are to be considered illustrative rather than restrictive.

FIG. 3A: Gross histochemical staining (TTC) of short-axis sections of hearts show the site of myocardial infarction (pale color, yellow arrows) in acute and chronic reperfusion injury. The acute section shows blood within the necrotic tissue and the chronic section shows yellow-brown stain within the necrotic tissue. Microstructural histopathology (100× magnification) of acute infarct (a1-a6) and corresponding remote sections show extravasation of red blood cells (Hematoxylin & Eosin, yellow arrows, inset), early deposition of collagen (Masson's Trichrome) and iron (Perl's stain, black arrows, inset) in the infarcted section (not observed in remote territories). Histopathology (100× magnification) of chronic infarct (b1-b6) and corresponding remote sections show grossly damaged myocardium (Hematoxylin & Eosin), dense deposition of collagen (Masson's trichrome) and iron (Perl's stain, black arrows, inset) in the infarcted section (not observed in remote territories). Insets show detailed views of tissue structures collected from regions indicated by arrows. Note the presence of iron among cardiomyocytes in incompletely infarcted sites (lower inset of b3). FIG. 3B: ICP-MS analysis of myocardial tissue obtained from Shams, Remote, Hemo−, and Hemo+ sections on day 56 post reperfusion (chronic) showed significantly higher amount of iron in Hemo+ compared to all other sections (*, $p<0.001$).

FIG. 4A: Representative CMR images (T2* and LGE) acquired from an animal with hemorrhagic myocardial infarction in acute and chronic phases along the long- and short-axis (along the dashed red line in the long axis images), along with corresponding ex-vivo images are shown. In-vivo T2* images (both acute and chronic phases) clearly demonstrate the evidence of signal loss in the LAD territory (arrows), where the hemorrhagic infarctions were expected to occur. Arrows in LGE images point to the site of infarction. For clarity, T2* maps (color-coded) are provided only along the short axis, and the corresponding long-axis T2*-weighted images, acquired at TE=18 ms, are also shown. FIG. 4B: Linear regression analysis between in-vivo T2* (acute and chronic) and ex-vivo T2* showed strong correlations indicating that ex-vivo T2* provides a reasonable estimate of in-vivo T2*. FIG. 4C: Linear regression analysis between ex-vivo log (T2*) and −log([Fe]) showed a strong correlation. FIG. 4D: Mixed-model linear regression analysis of mean ex-vivo T2* of Shams, Remote, Hemo−, and Hemo+ infarct sections showed significantly lower T2* (*, $p<0.001$) in Hemo+ compared to all other sections.

FIGS. 5A-5E depict, in accordance with various embodiments of the present invention, non-reperfusion hemorrhage mediated iron deposition. This figure depicts an example of short-axis T2* map (FIG. 5A) and LGE image (FIG. 5B) from a dog on day 7 post ligation of the left anterior descending coronary artery. As in FIG. 4, T2* changes were more pronounced in regions with hemorrhage. LGE MRI showed the area of MI and the extent of microvascular injury (hyperintense core). T2* images of chronic infarction (Day 113 post ligation, FIG. 5C) also show the presence of persistent byproducts of hemorrhage and the LGE MR (FIG. 5D) image show region of infarction corresponding to the region with hemorrhage 3 months post MI. (FIG. 5E) The TTC stained image confirms the presence of infarction and the brown discoloration within the infracted territories show presence of iron oxide deposition within the myocardial infarcts.

FIGS. 6A-6F depict, in accordance with various embodiments of the present invention, iron deposition increases electrical capacitance of chronic myocardial infarcts. FIG. 6A: Mixed-effects multi-linear regression analysis showed that the normalized permittivity (ratio of electrical permittivity of infarcted sections to remote sections, $\bar{\varepsilon}$) was dependent on [Fe]; FIG. 6B: however, a similar dependence was not found between normalized conductivity (ratio of electrical conductivity of infarcted sections to remote sections, $\bar{\sigma}$) and [Fe]. FIG. 6C: Mixed-model linear regression of mean $\bar{\varepsilon}$ measured from Remote, Hemo−, and Hemo+ infarct sections showed significantly greater $\bar{\varepsilon}$(*, $p<0.001$) in Hemo+ compared to Remote and Hemo− sections; FIG. 6D: however, mean $\bar{\sigma}$ measured from Remote, Hemo−, and Hemo+ infarct sections did not show any statistical difference in $\bar{\sigma}$ between the different sections. FIG. 6E: Mixed-effects multi-linear regression analysis between $\bar{\varepsilon}$ and log (T2*) was found to be dependent on log(T2*); FIG. 6F: however, a similar dependence was not found between $\bar{\sigma}$ and log(T2*).

FIG. 7A: Representative CMR images (acquired from a 42-year old patient following successful angioplasty) with significant T2* loss (arrows) at the site of acute and chronic myocardial infarction (infarction sites identified by LGE imaging, arrows) are shown. FIG. 7B: Linear regression analysis between acute and chronic T2* showed strong correlations. FIG. 7C: Mixed-model linear regression analysis of mean T2* of remote, non-hemorrhagic infarct (Hemo−), and hemorrhagic (Hemo+) infarct sections showed significantly lower T2* (^,*, p<0.001) in Hemo+ compared to all other sections in both acute and chronic infarctions, but were not different between remote and Hemo− in both acute and chronic states. However, no differences in T2* were observed between acute and chronic phases in Remote, Hemo−, and Hemo+ tissues.

FIGS. 11A-11E depict, in accordance with various embodiments of the present invention, the semi-automatic threshold-based analysis of images acquired from an infarcted dog during acute phase (day 3) MiII studies. (FIG. 11A) Representative LGE image showing gadolinium hyperenhanced infarcted region (red arrows) with microvascular obstruction (MO; dark region) enclosed within. (FIG. 11B) Infarcted myocardium (highlighted yellow pixels on the LGE image from (A)) identified as the hyperintense region with mean signal intensity (SI) 5 standard deviations (SDs) greater than that of reference ROI (blue ROI). MO (orange region) was included in the final analysis of infarcted myocardium. (FIG. 11C) Representative T2*-weighted image acquired at TE=18.38 ms showing hypointense hemorrhagic myocardium (red arrows). (FIG. 11D) Hemorrhagic myocardium (highlighted blue pixels on the T2*-weighted image from (C)) identified as the region with mean SI 2 SDs lesser than that of reference ROI (blue ROI). Region affected by off-resonance artifacts (white arrow) was not included in the analysis. (FIG. 11E) Color-coded T2* map showing the hemorrhagic myocardium (bright red region within a red ROI). Region affected by off-resonance artifact (white arrow) was excluded.

FIG. 12 depicts, in accordance with various embodiments of the present invention, schematic three-dimensional drawing of a capacitor cell used for tissue electrical measurements.

FIG. 19A shows a section of a macrophage with pronounced intracellular electron-dense material (arrows), which is organized into nodules (FIG. 19B). FIG. 19C shows lysosomal structures with disrupted membranes (arrow); intact membrane highlighted in red for ease of visualization. FIG. 19D shows atomic-resolution TEM images of a representative nanocrystalline particle from a nodular cluster. Notice the highly ordered pattern of aligned atomic columns. FIG. 19E shows the EDS spectrum confirming the strong presence of iron. FIG. 19F shows a selected area diffraction pattern obtained from the nodules, which reveals an exact fit with the pattern of a 6-line ferrihydrite with rings at 1) 0.150 nm, 2) 0.176 nm, 3) 0.214 nm, 4) 0.226 nm and 5) 0.256 nm.

FIGS. 25A-25E depict, in accordance with various embodiments of the present invention, transmission electron microscopy images of crystalline deposits within macrophages found in the territories of chronic myocardial infarction. FIG. 25A shows a longitudinal section of the macrophage cell with pronounced intracellular electron-dense material deposits (arrows). FIG. 25B and FIG. 25C show enlarged area of a typical nodular pattern of material deposition. FIG. 25D shows the nodules are composed of clustered highly crystalline nanoparticles with an approximate diameter of 2.5 nm.

FIG. 26A shows atomic resolution STEM image of a representative nanocrystalline particle from a Fe nodular cluster in a macrophage intracellular space. Notice the highly ordered pattern of aligned atomic columns. FIG. 26B shows the EDS spectrum of the nodular material confirms the strong Fe presence. FIG. 26C shows a selected area diffraction pattern obtained from the Fe nodules reveals an exact fit with the pattern of a 6-line ferrihydrite (see e.g., Jansen E, Kyek A, Schafer W, Schwertmann U. The structure of six-line ferrihydrite. Appl Phys a-Mater 2002; 74: S1004-S1006). The respective values of diffraction rings are: 1) 0.150 nm, 2) 0.176 nm, 3) 0.214 nm, 4) 0.226 and 5) 0.256 nm.

FIGS. 27A-27F depict, in accordance with various embodiments of the present invention, relationship between pro-inflammatory burden and chronic iron deposition. Representative contiguous ex-vivo histology sections stained with EMT, Perls, and monoclonal antibodies for MAC387, CD163, Il-1β, TNF-α and MMP-9 are shown from reperfused and non-reperfused canines with and without $T_2^*$ losses ($T_2^*+$ and $T_2^*-$ respectively) as observed in ex-vivo $T_2^*$-weighted images (FIG. 27A). Note significant co-localization of Mac387+ cells, TNF-α activity, and MMP-9 activity with chronic iron deposits. Strong linear relationships of the area of iron (measured from Perls stain) were observed with area of MAC387+ cells ($R^2=0.87$, p<0.001; FIG. 27B), area of CD163+ cells ($R^2=0.64$, p<0.001; FIG. 27C), area of IL-1β activity ($R^2=0.53$, p<0.001; FIG. 27D), area of TNF-α activity ($R^2=0.73$, p<0.001; FIG. 27E), and area of MMP-9 activity ($R^2=0.85$, p<0.001; FIG. 27F).

DETAILED DESCRIPTION OF THE INVENTION

Figure 1:
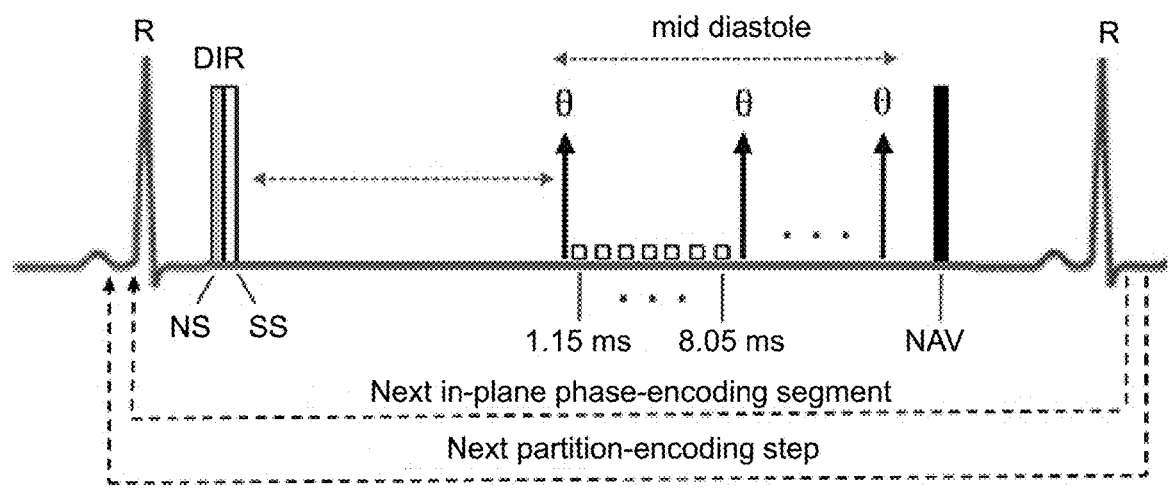
FIG. 1 depicts, in accordance with various embodiments of the present invention, the timing diagram for navigator-gated, ECG-triggered segmented, dark-blood prepared 3D multi gradient-echo T2* mapping sequence. Double Inversion block (DIR) is (non-selective (NS) and slice-selective (SS) inversion pulses; TI is the inversion time to null blood; θ is the flip angle; and NAV is the navigator pulse for respiratory gating. DIR is applied during late diastole with a trigger delay (also the TI time) during which the blood in the left-ventricle (inverted by the SS pulse) is replaced with fresh blood prior to data acquisition (mid diastole).

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ *ed*, Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ *ed*., revised ed., J. Wiley & Sons (New York, N.Y. 2006); Smith, *March's Advanced Organic Chemistry Reactions, Mechanisms and Structure* 7$^{th}$ *ed*., J. Wiley & Sons (New York, N.Y. 2013); Singleton, *Dictionary of DNA and Genome Technology* 3$^{rd}$ *ed*., Wiley-Blackwell (Nov. 28, 2012); and Green and Sambrook, *Molecular Cloning: A Laboratory Manual* 4th *ed*., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described. For purposes of the present invention, the following terms are defined below.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of persistent microvascular obstruction (PMO) or microvascular obstruction (MO), delay or slowing of PMO or MO, and amelioration or palliation of symptoms associated with PMO or MO.

"Diseases", "conditions" and "disease conditions," as used herein may include, but are in no way limited to any form of cardiovascular conditions, diseases or disorders. Cardiovascular diseases are a class of diseases that involve the heart or blood vessels. Non-limiting examples of cardiovascular disease include: persistent microvascular obstruction (PMO), microvascular obstruction (MO), ischemic heart disease (IHD), myocardial infarction, acute myocardial infarction, hemorrhagic myocardial infarction, coronary artery disease, coronary heart disease, cardiomyopathy, stroke, hypertensive heart disease, heart failure, pulmonary heart disease, ischemic syndrome, coronary microvascular disease, cardiac dysrhythmias, rheumatic heart disease (RHD), aortic aneurysms, cardiomyopathy, atrial fibrillation, congenital heart disease, endocarditis, inflammatory heart disease, endocarditis, inflammatory cardiomegaly, myocarditis, valvular heart disease, cerebrovascular disease, and peripheral artery disease (PAD).

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, via inhalation, oral, anal, intra-anal, peri-anal, transmucosal, transdermal, parenteral, enteral, topical or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., PMO or MO) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

"Mechanical abnormalities" as used herein refers to deviations in cardiac contractions that lead to changes in mechanical deformations that mediate potential changes in standard volumetric indices. Regional abnormalities in cardiac contraction leading to alterations in volumetric indices including but not limited to ejection fraction (EF), blood pressure, cardiac output (CO), and/or left ventricle end diastolic volume (LVEDV) in the heart due to iron deposition post myocardial infarction. Poor myocardial contraction can also lead to blood stasis (i.e. clot/thrombus formation), which can subsequently become a systemic embolus/emboli that lead to stroke, secondary myocardial infarction, or cause other vascular obstructions.

"Electrical abnormalities" as used herein refer to deviation in heart rhythm and heart rate. In particular, the surface ECG and endo- and/or epi-cardial electrograms that identify changes in QRS duration, QT duration/dispersion, heart-rate variability, Q-waves, T-waves, effective refractory period (ERP), action potential duration, isolated late potentials, or combinations thereof may be used.

"Hemorrhage" as used herein refers to pooling of blood within a vessel or extravasation of blood into the interstitial space Post infarction remodeling which leads to ischemic heart failure and sudden cardiac death are not well understood. The inventors have shown that chronic iron deposition following myocardial infarction can be a source of active inflammation that contributes to these adverse outcomes. The inventors demonstrate that myocardial infarction patients with persistent microvascular obstruction (PMO) or microvascular obstruction (MO) have regional chronic iron deposition and that this residual iron is a source of prolonged inflammatory burden, which mediates adverse left ventricular remodeling and malignant ventricular arrhythmia. Moreover, the inventors show that PMO or MO may happen in acute phase of infraction and may be identified with MRI.

Device therapy (e.g., implantable cardioverter-defibrillator (ICD)) to overcome ventricular arrhythmia and chelation therapy to remove metallic substrates in post infarction patients have been attempted. However, these approaches did not show significant benefit because they failed to target appropriate infarction patients (i.e., those predisposed to or with iron deposition following myocardial infarction on the basis of MRI).

The inventors use MRI to identify appropriate infarction patients since it is in these patients the expensive medical therapies are expected to be most effective. The inventors show that patients with hemorrhagic infarction and patients without hemorrhage but with persistent microvascular obstruction (i.e., those with blood stasis within MI from non-reperfused MIs) can have chronic iron deposition. Using MRI to identify appropriate infarct patient population and then taking therapeutic measures to marginalize adverse outcomes are important in the optimal management of these patients.

In various embodiments, the invention is directed towards developing a non-invasive image-guided approach, based on Magnetic Resonance Imaging (MRI), for predicting cardiac arrhythmias that cause sudden cardiac death. While not wishing to be bound by any particular theory, the inventors hypothesize that reperfusion hemorrhaging leads to localized depositions of iron oxide within the myocardium, which can be characterized by MRI. These iron particulates may act as substrates for cardiac arrhythmias mediating sudden cardiac death. The inventors have also show that hemorrhage of the myocardium is not only limited to reperfusion but is also associated with non-reperfused myocardial infarction and that such infarctions also lead to gross deposition of iron-oxide. Since iron oxide induces changes in electrical properties of myocardium, both non-reperfused and reperfused MIs with iron deposition are prone to a higher degree of risk of cardiac arrhythmias.

A subpopulation of MI patients develop microvascular obstruction (MO) in their hearts (MO+); and further, a subpopulation of MO+ patients develop persistent microvascular obstruction (PMO) (PMO+). PMO+ patients can be categorized into four subgroups based on if their hearts are reperfused or not and if their hearts have hemorrhage. These four groups are: reperfusion with hemorrhage (PMO+R/H+ patients), reperfusion without hemorrhage (PMO+R/H− patients), non-reperfusion with hemorrhage (PMO+NR/H+ patients), and non-reperfusion without hemorrhage (PMO+NR/H− patients). Among these four subgroups, PMO+R/H− and PMO+NR/H− patients together constitute a subpopulation of MI patients with PMO but without hemorrhage (PMO+H− patients), while PMO+R/H+ and PMO+NR/H+ patients together constitute a subpopulation of MI patients with PMO and hemorrhage (PMO+H+ patients). In other words, MI patients with PMO may be divided into two subpopulations: those without hemorrhage (PMO+H− patients) and those with hemorrhage (PMO+H+ patients). Hemorrhagic myocardial infarction (hMI) patients belong to the PMO+H+ subpopulation.

As hemorrhage is always accompanied with PMO, patients without PMO (PMO−) have no hemorrhage and are always H−. As such, PMO− patients may be divided into two groups: reperfusion (PMO− R/H− patients) and non-reperfusion (PMO− NR/H− patients).

The inventors investigated MI patients without hemorrhage, as MI patients may be divided into two subpopulations: those with hemorrhage (H+ patients; e.g., hMI patients) and those without hemorrhage (H− patients; e.g., non-hMI patients). While H+MI patients always have PMO, H− MI patients do not necessarily have PMO. As such, H− MI patients can be further divided into two subgroups: those with PMO (PMO+H−) and those without PMO (PMO−H−).

In various embodiments, the present invention provides a prognosis method of determining the prognosis for a subject who had myocardial infarction (MI). The method comprises: imaging the subject's heart; identifying persistent microvascular obstruction (PMO), and/or iron deposition, and/or fat accumulation in the subject's heart; and determining a poor prognosis for the subject. In some embodiments, the method comprises: identifying persistent microvascular obstruction (PMO) in the subject's heart; and determining a poor prognosis for the subject. In some embodiments, the method comprises: identifying iron deposition in the subject's heart; and determining a poor prognosis for the subject. In some embodiments, the method comprises: identifying fat accumulation in the subject's heart; and determining a poor prognosis for the subject. In various embodiments, the subject has no hemorrhage in the heart, that is, H− patient (e.g., non-hMI patient). In certain embodiments, the method further comprises identifying no hemorrhage in the subject's heart.

In various embodiments, the present invention provides a treatment method of treating a subject who had myocardial infarction (MI). The method comprises: imaging the subject's heart; identifying persistent microvascular obstruction (PMO), and/or iron deposition, and/or fat accumulation in the subject's heart; and administering to the subject a therapeutically effective amount of a therapeutic agent, thereby treating the subject. In some embodiments, the method comprises: identifying persistent microvascular obstruction (PMO) in the subject's heart; and administering to the subject a therapeutically effective amount of a therapeutic agent, thereby treating the subject. In some embodiments, the method comprises: identifying iron deposition in the subject's heart; and administering to the subject a therapeutically effective amount of a therapeutic agent, thereby treating the subject. In some embodiments, the method comprises: identifying fat accumulation in the subject's heart; and administering to the subject a therapeutically effective amount of a therapeutic agent, thereby treating the subject. In various embodiments, the subject has no hemorrhage in the heart, that is, H− patient (e.g., non-hMI patient). In certain embodiments, the method further comprises identifying no hemorrhage in the subject's heart.

In various embodiments, the present invention provides a method of treating a subject with heart PMO and/or a condition associated with heart PMO, heart iron deposition and/or a condition associated with heart iron deposition, heart fat accumulation and/or a condition associated with heart fat accumulation. The method comprises: providing a therapeutic agent, wherein the therapeutic is a chelating agent, anti-inflammatory agent, lipid-lowering agent, carbon monoxide therapy, heme-oxygenase regulating drug, or an agent capable of promoting heart blood flow, or a combination thereof; and administering to the subject a therapeutically effective amount of the therapeutic agent, thereby treating the subject. In some embodiments, the method treats heart PMO and/or a condition associated with heart PMO. In some embodiments, the method treats heart iron deposition and/or a condition associated with heart iron deposition. In some embodiments, the method treats heart fat accumulation and/or a condition associated with heart fat accumulation. In various embodiments, PMO, and/or iron deposition, and/or fat accumulation in the subject's heart is identified through imaging the subject's heart. In various embodiments, the subject is a subject is a MI patient who was identified with PMO, and/or iron deposition, and/or fat accumulation in the heart through an imaging method as described herein. In various embodiments, the subject has been prognosed with a prognosis method as disclosed herein.

In some embodiments, the subject had reperfusion in the heart. In other embodiments, the subject had no reperfusion in the heart. In some embodiments, the subject is an H− patient. In other embodiments, the subject is an H+ patient. In some embodiment, the subject is a PMO+R/H− patient. In some embodiment, the subject is a PMO+NR/H− patient. In some embodiment, the subject is a PMO+R/H+ patient. In some embodiment, the subject is a PMO+NR/H+ patient.

In various embodiments, imaging the subject's heart is performed with cardiac magnetic resonance imaging (CMR), late-gadolinium enhancement CMR (LGE-CMR), cine CMR, T2* CMR, chemical shift-encoded T2* CMR, T2 CMR, T1 CMR, T1ρ CMR, SPECT, PET, CT, or echocardiography (ECG), or a combination thereof. In certain embodiments, imaging the subject's heart is performed with CMR. Examples of CMR include but are not limited to LGE-CMR, cine CMR, T2* CMR, and chemical shift-encoded T2* CMR, T2 CMR, T1 CMR, and T1ρ CMR.

In various embodiments, persistent microvascular obstruction (PMO), and/or iron deposition, and/or fat accumulation is identified in the heart's infarcted region, or non-infarcted region, or a combination thereof.

In various embodiments, persistent microvascular obstruction (PMO), and/or iron deposition, and/or fat accumulation is identified in the heart's myocardial tissue, non-myocardial tissue, myocardium, endocardium, epicardium, pericardium, or pericardial cavity, or a combination thereof. In various embodiments, persistent microvascular obstruction (PMO), and/or iron deposition, and/or fat accumulation is identified in the heart's valvular tissue, non-valvular tissue, pulmonary valve, tricuspid valve, mitral valve, or aortic valve, or a combination thereof.

In various embodiments, persistent microvascular obstruction (PMO), and/or iron deposition, and/or fat accumulation is identified in the heart's blood vessel, coronary blood vessel, non-coronary blood vessel, or a combination thereof. In various embodiments, persistent microvascular obstruction (PMO), and/or iron deposition, and/or fat accumulation is identified in the heart's coronary artery, right coronary artery, left coronary artery, left anterior descending artery, coronary vein, cardiac vein, great cardiac vein, middle cardiac vein, small cardiac vein, or anterior cardiac vein, or a combination thereof. In various embodiments, persistent microvascular obstruction (PMO), and/or iron deposition, and/or fat accumulation is identified in the heart's superior vena cava, inferior vena cava, pulmonary trunk, pulmonary artery, pulmonary vein, right pulmonary vein, left pulmonary vein, or aorta, or a combination thereof.

In various embodiments, the poor prognosis is prolonged inflammation burden, increased likelihood of adverse cardiac remodeling, increased likelihood of electrical abnormality, increased likelihood of mechanical abnormality, increased likelihood of cardiac arrhythmia, increased likelihood of ischemic heart failure, increased likelihood of chronic heart failure (CHF), increased likelihood of major adverse cardiovascular event (MACE), or increased likelihood of sudden cardiac death, or a combination thereof.

In various embodiments, a prognosis or treatment method as disclosed herein further comprises comprising measuring the subject's blood levels of any one or more of hepcidin, biliverdin, bilirubin, carbon monoxide, heme (heam) oxgenase, Fe bound to transferrin, ferritin, IL-1β, TNF-α, IL-6, MMP, NLRP3 inflammasome, CD36, CD163, GLUT-4, adiponectin, and unbound iron binding capacity (UIBC); and detecting increased blood levels of any one or more of hepcidin biliverdin, bilirubin, carbon monoxide, heme (haem) oxygenase, Fe bound to transferrin, ferritin, IL-1β, TNF-α, IL-6, MMP, NLRP3 inflammasome, CD36, CD163, and adiponectin and/or detecting decreased blood levels of UIBC.

In various embodiments, a treatment method as disclosed herein treats a symptom or condition that is associated with MI. Exemplar symptoms or conditions associated with MI include but are not limited to inflammation burden, adverse cardiac remodeling, electrical abnormality, mechanical abnormality, cardiac arrhythmia, ischemic heart failure, chronic heart failure (CHF), major adverse cardiovascular event (MACE), and sudden cardiac death.

In various embodiments, a treatment method as disclosed herein treats a symptom or condition that is associated with PMO, iron deposition, or fat accumulation, or a combination thereof. Exemplar symptoms or conditions associated with PMO in the heart include but are not limited to inflammation burden, adverse cardiac remodeling, electrical abnormality, mechanical abnormality, cardiac arrhythmia, ischemic heart failure, chronic heart failure (CHF), major adverse cardiovascular event (MACE), and sudden cardiac death. Exemplar symptoms or conditions associated with iron deposition in the heart include but are not limited to inflammation burden, adverse cardiac remodeling, electrical abnormality, mechanical abnormality, cardiac arrhythmia, ischemic heart failure, chronic heart failure (CHF), major adverse cardiovascular event (MACE), and sudden cardiac death. Exemplar symptoms or conditions associated with fat accumulation in the heart include but are not limited to inflammation burden, adverse cardiac remodeling, electrical abnormality, mechanical abnormality, cardiac arrhythmia, ischemic heart failure, chronic heart failure (CHF), major adverse cardiovascular event (MACE), and sudden cardiac death.

In various embodiments, the therapeutic agent is provided in a pharmaceutical composition. In various embodiments, the therapeutic agent is a chelating agent, anti-inflammatory agent, cellular therapies, lipid-lowering agent, carbon monoxide therapy, heme-oxygenase regulating drug, an agent capable of promoting heart blood flow, an agent capable of promoting clearance of iron with enhanced macrophage activity, a phagocytosis-enhancing agent, or an agent capable of disrupting the biosynthesis of iron oxide crystals or preventing aggregation of nanocrystals, or a combination thereof.

In various embodiments, the chelating agent is deferoxamine, deferasirox, or deferiprone, or a combination thereof.

In various embodiments, the anti-inflammatory agent is a corticosteroid, nonsteroidal anti-inflammatory drug (NSAID), anti-IL-1beta (e.g., Anakinra), anti-TNF-a (e.g., Etanercept and Infliximab), anti-IL-6 (e.g., Tocilizumab), anti-MMP (e.g., PG-116800 and Doxycycline), macrophage modulators (e.g., phosphatidylserine-presenting liposomes), NLRP3 inflammasome inhibitors (e.g., 16673-34-0 (5-chloro-2-methoxy-N-[2-(4-sulfamoylphenyl)ethyl]benzamide)), inflammasome antagonists (e.g., P2X7 antagonist), or anti-diabetic medications (for example, insulin (e.g., Humulin, Novolin, Humalog), metformin (e.g., Glucophage, Glucophage XR, Fortamet, Glumetza, Riomet), sulfonylureas, meglitinides, incretin mimetics, biguanides, amylinomimetic agent (e.g., Pramlintide), lipase inhibitors such as orlistat (e.g., Xenical, Alli), thiazolidinediones, Pioglitazone (e.g., Actos), Rosiglitazone (e.g., Avandia), corticosteroids such as Prednisone (e.g., Rayos), dipeptidyl peptidase-4 inhibitors, SGLT2 inhibitors, and glucagon-like peptide-1 analogs or agonists such as Exenatide (e.g., Bydureon, Byetta) and Liraglutide (e.g., Victoza)), or a combination thereof.

In various embodiments, the lipid-lowering agent is a statin, cholesterol absorption inhibitors (e.g., ezetimbie), bile-acid-binding resins/sequestrants (e.g., Cholestyramine), niacin, or vitamin B3, or a combination thereof.

In various embodiments, the agent capable of promoting heart blood flow is arterial $CO_2$, adenosine, regadenoson, dypridamole, persantine, or nitric oxide, or a combination thereof.

In various embodiments, the therapeutic agent is an agent capable of promoting clearance of iron with enhanced macrophage activity. In various embodiments, the agent capable of promoting clearance of iron with enhanced macrophage activity is a phagocytosis-enhancing agent, for example, green tea polyphenols, arabinoxylan, recombinant interferon gamma and nitric oxide.

In various embodiments, the therapeutic agent is an agent capable of disrupting the biosynthesis of iron oxide crystals or preventing aggregation of nanocrystals.

In various embodiments, the invention provides methods for diagnosing reperfusion/non-reperfusion hemorrhage and predicting cardiac arrhythmias and sudden cardiac death in subjects comprising using imaging techniques to detect regional iron oxide deposition. In various embodiments, the invention also provides treatment methods for subject at increased risk of sudden cardiac death.

In various embodiments, the present invention provides a method for diagnosing reperfusion and/or non-reperfusion hemorrhage in a subject in need thereof. The method comprises: obtaining MRI images of the subject's heart; detecting regional iron oxide deposition in the heart; and diagnosing presence or absence of reperfusion and/or non-reperfusion hemorrhage in the subject, wherein presence of iron oxide deposition in regions of the heart is indicative of reperfusion and/or non-reperfusion hemorrhage in the subject, so as to diagnose reperfusion/non-reperfusion hemorrhage in the subject. In various embodiments, the method further comprises measuring blood levels of any one or more of hepcidin, carbon monoxide, bilirubin, unbound iron binding capacity (UIBC), Fe bound to transferrin, ferritin, heme (heam) oxgenase, biliverdin or a combination thereof, in the subject, wherein an increase in hepcidin biliverdin, bilirubin, carbon monoxide, heme (haem) oxygenase, Fe bound to transferrin, ferritin and/or a decrease in UIBC is indicative of hemorrhagic myocardial infarction in the subject.

In various embodiments, the present invention provides a method for diagnosing reperfusion hemorrhage in a subject, comprising: obtaining MRI images of the subject's heart; detecting regional iron oxide deposition in the infarcted region of the heart; and diagnosing presence or absence of reperfusion hemorrhage in the subject, wherein presence of iron oxide deposition in the infarcted regions of the heart is indicative of reperfusion hemorrhage in the subject, so as to diagnose reperfusion hemorrhage in the subject, wherein the subject has had a hemorrhagic myocardial infarction. In various embodiments, the method further comprises measuring blood levels of any one or more of hepcidin, carbon monoxide, bilirubin, unbound iron binding capacity (UIBC), Fe bound to transferrin, ferritin, heme (heam) oxgenase, biliverdin or a combination thereof, in the subject, wherein an increase in hepcidin biliverdin, bilirubin, carbon monoxide, heme (haem) oxygenase, Fe bound to transferrin, ferritin and/or a decrease in UIBC is indicative of hemorrhagic myocardial infarction in the subject.

In various embodiments, the present invention provides a method for predicting cardiac arrhythmias in a subject in need thereof. The method comprises diagnosing reperfusion and/or non-reperfusion hemorrhage in the subject by a method as described herein, wherein presence of reperfusion and/or non-reperfusion hemorrhage is indicative of increased likelihood of cardiac arrhythmias in the subject, thereby predicting cardiac arrhythmias in the subject.

In various embodiments, the present invention provides a method for predicting cardiac arrhythmias in a subject that has had a hemorrhagic myocardial infarction, comprising diagnosing reperfusion hemorrhage in the subject by a method as described herein, wherein presence of reperfusion hemorrhage is indicative of increased likelihood of cardiac arrhythmias in the subject, thereby predicting cardiac arrhythmias in the subject.

In various embodiments, the present invention provides a method for predicting sudden cardiac death in a subject in need thereof. The method comprises predicting cardiac arrhythmias by a method as described herein, wherein increased likelihood of cardiac arrhythmias is indicative of increased likelihood of sudden cardiac death in the subject, thereby predicting sudden cardiac death in the subject.

In various embodiments, the present invention provides a method for predicting sudden cardiac death in a subject that has had a hemorrhagic myocardial infarction, comprising predicting cardiac arrhythmias by a method as described herein, wherein increased likelihood of cardiac arrhythmias is indicative of increased likelihood of sudden cardiac death in the subject, thereby predicting sudden cardiac death in the subject.

In various embodiments, the present invention provides a method for determining the prognosis after a myocardial infarction in a subject in need thereof. The method comprises diagnosing reperfusion and/or non-reperfusion hemorrhage in the subject by a method as described herein, wherein the presence of reperfusion and/or non-reperfusion hemorrhage in the subject is indicative of a poor prognosis, thereby determining the prognosis of a myocardial infarction in the subject.

In various embodiments, the present invention provides a method for determining the prognosis after a hemorrhagic myocardial infarction in a subject, comprising diagnosing reperfusion hemorrhage in the subject by a method as described herein, wherein the presence of reperfusion hemorrhage in the subject is indicative of a poor prognosis, thereby determining the prognosis of a hemorrhagic myocardial infarction in the subject.

In various embodiments, the present invention provides a method for predicting cardiac arrhythmias in a subject in need thereof. The method comprises: obtaining MRI images of the subject's heart; detecting regional iron oxide deposition in the heart, wherein the subject has not undergone a myocardial infarction and wherein the presence of iron oxide deposits in one or more regions of the heart is indicative of increased likelihood of cardiac arrhythmia in the subject, so as to predict cardiac arrhythmia in the subject.

In various embodiments, the present invention provides a method for predicting cardiac arrhythmias in a subject comprising: obtaining MRI images of the subject's heart; detecting regional iron oxide deposition in the infarcted region of the heart, wherein the subject has undergone a hemorrhagic myocardial infarction and wherein the presence of iron oxide deposits in one or more infarcted regions of the heart is indicative of increased likelihood of cardiac arrhythmia in the subject, so as to predict cardiac arrhythmia in the subject.

In various embodiments, the present invention provides a method for treating a subject at an increased risk of sudden cardiac death associated with regional iron deposition in the heart. The method comprises: providing a composition comprising a chelating agent; and administering to the subject an effective amount of the composition, so as to treating the subject at an increased risk of sudden cardiac death associated with regional iron deposition in the heart. In various embodiments, the method further comprises administering a composition comprising carbon monoxide and/or a composition comprising haem-oxygenase regulating drug.

In various embodiments, the present invention provides a method for treating a subject that has had a hemorrhagic myocardial infarction and is at an increased risk of sudden cardiac death associated with regional iron deposition in the heart, comprising: providing a composition comprising a chelating agent; and administering to the subject an effective amount of the composition, so as to treating the subject at an increased risk of sudden cardiac death associated with regional iron deposition in the infarcted region of the heart. In various embodiments, the method further comprises administering a composition comprising carbon monoxide and/or a composition comprising haem-oxygenase regulating drug.

In various embodiments, the present invention provides a method for treating a subject with localized deposition of iron oxide in myocardial tissue. The method comprises: obtaining MRI images of the subject's heart; detecting localized iron oxide deposition in the heart; providing a composition comprising a chelating agent; and administering an effective amount of the composition to the subject so as to treat the subject with localized deposition of iron in the myocardial tissue. In various embodiments, the method further comprises administering a composition comprising carbon monoxide and/or a composition comprising haem-oxygenase regulating drug.

In various embodiments, the present invention provides a method for treating a subject with localized deposition of iron oxide in myocardial tissue, comprising: obtaining MRI images of the subject's heart; detecting localized iron oxide deposition in the infarcted region of the heart; diagnosing presence or absence of reperfusion hemorrhage in the subject, wherein presence of localized iron oxide deposition in the infarcted region of the heart is indicative of reperfusion hemorrhage in the subject; providing a composition comprising a chelating agent to the subject diagnosed with reperfusion hemorrhage; and administering an effective amount of the composition to the subject so as to treat the subject with localized deposition of iron in the infarcted region of the myocardial tissue, wherein the subject has had a hemorrhagic myocardial infarction. In various embodiments, the method further comprises administering a composition comprising carbon monoxide and/or a composition comprising haem-oxygenase regulating drug.

In various embodiments, the present invention provides a method of treating a subject with electrical conduction abnormalities and/or mechanical abnormalities in the myocardium. The method comprises: obtaining MRI images of the subject's heart; detecting localized iron oxide deposition in the heart; providing a composition comprising a chelating agent; and administering an effective amount of the composition to the subject so as to treat the subject with localized deposition of iron in the myocardial tissue, wherein the electrical conduction abnormalities and/or mechanical abnormalities result from localized deposition of iron oxide in myocardial tissue. In various embodiments, the method further comprises administering a composition comprising carbon monoxide and/or a composition comprising haem-oxygenase regulating drug.

In various embodiments, the present invention provides a method of treating a subject with electrical conduction abnormalities and/or mechanical abnormalities in the myocardium, comprising: obtaining MRI images of the subject's heart; detecting localized iron oxide deposition in the infarcted region of the heart; diagnosing presence or absence of reperfusion hemorrhage in the subject, wherein presence of localized iron oxide deposition in the infarcted region of the heart is indicative of reperfusion hemorrhage in the subject; providing a composition comprising a chelating agent to the subject diagnosed with reperfusion hemorrhage; and administering an effective amount of the composition to the subject so as to treat the subject with localized deposition of iron in the infarcted region of the myocardial tissue, wherein the electrical conduction abnormalities and/or mechanical abnormalities result from localized deposition of iron oxide in the infarcted region of myocardial tissue, wherein the subject has had a hemorrhagic myocardial infarction. In various embodiments, the method further comprises administering a composition comprising carbon monoxide and/or a composition comprising haem-oxygenase regulating drug.

In various embodiments, the present invention provides a method for reducing myocardial inflammation in a subject in need thereof. The method comprises: obtaining MRI images of the subject's heart; detecting regional iron oxide deposits in the heart, wherein presence of iron oxide deposits is indicative of increased myocardial inflammation; and administering an effective amount of a composition comprising a chelating agent so as to reduce myocardial inflammation in the subject. In various embodiments, the method further comprises administering a composition comprising carbon monoxide and/or a composition comprising haem-oxygenase regulating drug.

In various embodiments, the present invention provides a method for reducing myocardial inflammation in a subject, comprising: obtaining MRI images of the subject's heart; detecting regional iron oxide deposits in the infarcted region of the heart, wherein presence of iron oxide deposits is indicative of increased myocardial inflammation; and administering an effective amount of a composition comprising a chelating agent so as to reduce myocardial inflammation in the subject, wherein the subject has had a hemorrhagic myocardial infarction. In various embodiments, the method further comprises administering a composition comprising carbon monoxide and/or a composition comprising haem-oxygenase regulating drug.

In various embodiments, the present invention provides a method for reducing adverse remodeling of the heart in a subject in need thereof. The method comprises reducing myocardial inflammation by a method as described herein. In various embodiments, the method further comprises administering a composition comprising carbon monoxide and/or a composition comprising haem-oxygenase regulating drug.

In various embodiments, the chelating agent is any one or more of Deferoxamine, Deferasirox, Deferiprone or a combination thereof. In various embodiments, the composition comprising the chelating agent and the composition comprising carbon monoxide and/or the composition comprising haem-oxygenase regulating drugs are administered concurrently or sequentially.

In various embodiments, the localized deposition of iron in the myocardial tissue results in cardiac arrhythmia. In various embodiments, cardiac arrhythmia is atrial arrhythmia or ventricular arrhythmia.

In various embodiments, the subject is any one or more of human, monkey, ape, dog, cat, cow, horse, goat, pig, rabbit, mouse and rat. In various embodiments, the subject is any one or more of myocardial infarction patient, a patient with ischemic heart disease or a patient with chronic iron deposition in the heart. In some embodiments, the subject is a patient with ischemic heart disease. In various embodiments, the subject is a myocardial infarction patient whose treatment is initiated at least 4 hours after the onset of symptoms of myocardial infarction. In various embodiments, the symptoms of myocardial infarction are any one or more of chest pain, elevated ST segment in an electrocardiogram (ECG)

and/or elevated troponin levels in the blood. In various embodiments, the subject has undergone one or more hemorrhagic myocardial infarctions resulting in myocardial inflammation. In various embodiments, the subject is implanted with an implantable cardioverter-defibrillator (ICD) or a pacemaker.

Free-Breathing 3D T2* Maps at 3 T for Characterizing Iron Depositions in the Heart Breath-held, ECG-triggered, 2D T2* mapping at 1.5 T is the current standard for identifying iron overload in the heart. However, this approach has a number of limitations for the inventors' application: (i) the inventor's early studies and the literature suggest that, in the setting of large infarcts, breath holding may trigger arrhythmias, (ii) repetitive breath-held image acquisitions have led to fatal arrhythmias in canines with hemorrhage, and (iii) non-fatal arrhythmias demand undesirably long breath holding times. Partial volume effects in the through-plane direction can significantly reduce the conspicuity of the regions with an iron overload.

Bright blood T2* maps are prone to significant image artifacts (ghosts and smearing), particularly when echo times (TE) are long. At 1.5 Tesla (T), the sensitivity for visualizing smaller iron depositions can be limited and require the use of longer TEs in spite first-order flow compensation at every TE. Doubling the field strength is known to increase the image contrast for detecting iron particulates by a factor of 4, which in turn implies that significantly shorter TEs may be used to generate T2* maps. Flow compensation at shorter TEs and dark-blood imaging may be ideal for overcoming these artifacts.

The current approach also has limited signal-to-noise (S/N) characteristics. 3D mGRE acquisitions, particularly when performed at 3.0T, can increase the S/N and permit the use of image acceleration strategies to reduce scan time without compromising S/N. The herein proposed dark-blood T2* MRI may provide greater patient comfort/safety, substantially improved image quality and sensitivity for detecting localized myocardial iron deposits.

Iron Deposition in Chronic Infarcts Following Reperfusion and Non-Reperfusion

Until recently, non-invasive imaging methods for detecting reperfusion and non-reperfusion in vivo were not available. Therefore, studies of reperfusion and non-reperfusion relied solely on autopsy data, were primarily observational descriptions, and were limited in size. Although T2*-based detection of reperfusion is gaining recognition, the fate of reperfusion hemorrhage and its relation to an aging (chronic) infarction has not been previously studied. The inventor herein provides evidence (both imaging and histology) to suggest that reperfusion and non-reperfusion hemorrhage leads to regional iron overloading in the heart and may have a role in the progression of heart failure.

Iron Deposits within Chronic Infarcts Mediating Fatal Cardiac Arrhythmia

Cardiac arrhythmias are common among patients with reperfused and non-reperfused infarctions, and if untreated and undetected, they can cause sudden cardiac death. Current understanding is that the infarct territories enable re-entry currents leading to ventricular tachycardia (VT) or VF. However, it is also known that not all infarct territories can mediate cardiac arrhythmias. In fact, the true substrate(s) that catalyze cardiac arrhythmia are not fully understood. The inventors propose that iron deposition within the chronic infarcts (cMI) may be an important substrate for altering the electrical conductivity in the heart. The inventor hypothesizes that iron deposits from hemorrhagic infarcts, hemosiderin (highest conductive compound found in living organisms can alter the tissue capacitance and thereby serve as a source of potential (voltage) sinks. As the conduction potential is drained from the depolarizing current, regional conduction abnormalities culminate in mechanical dysynchrony, which facilitate hemodynamic impairment causing death. The inventors' show that cMI with iron overload have significantly greater electrical capacitance than healthy (remote). Identification of iron particulates as a critical substrate for cardiac arrhythmia on the basis of noninvasive imaging is likely to be a significant finding in the overall understanding of SCD in patients with a history of cMI.

Reducing the Risk of Fatal Ventricular Arrhythmias or Adverse Ventricular Remodeling Via Drug Therapy Chronic, localized, iron overloading is a feature of hemorrhagic stroke. Such iron overload has been shown to catalyze free-radical reactions that lead to significant tissue damage. The benefits of iron chelation therapies in this setting are well recognized. Additionally, chelation therapies in the heart for thalassemia (ferritin cardiomyopathy) have also shown to be highly beneficial. These studies suggest that the use of clinically approved iron chelators, such as Deferoxamine, may also allow for the removal of iron deposits from reperfusion and non-reperfusion hemorrhage in the heart. To date, the use of chelators for removing myocardial iron deposits from infarcted territories has not been studied. The demonstration that iron chelators may be used to reduce the risk of cardiac arrhythmia in patients with a history of chronic infarction may prove to be an important medical treatment for infarct patients with a risk of SCD.

In addition to chelation therapies to remove iron oxide deposits, carbon monoxide therapies, and other haem-oxygenase regulating drugs may also be used to prevent deposition of iron. These additional drug therapies can be used alone or in conjunction with chelation therapies to augment the reduction of iron in myocardial tissue. In some embodiments, subjects with iron oxide deposits are implanted with an implantable cardioverter-defibrillator (ICD) or a pacemaker. Currently, the substrate mediating the development of malignant ventricular arrhythmias (mVAs) in CMI patients is unclear. Earlier studies examining the nature of arrhythmogenesis in CMI indicate that fibrosis has been the primary structural observation associated with mVA. The principal mechanism was slowing of conduction as a result of the presence of collagen fibers acting as a barrier against electrophysiological propagation. Paradoxically, not all patients with CMI develop mVA despite the presence of intramyocardial collagen.

More recent findings suggest that fat deposits secondary to lipomatous metaplasia (LM) may also be associated with the pathogenesis of mVA in CMI. It has been demonstrated that intramyocardial adipose significantly impedes myocardial conduction and attenuates both electrogram amplitude and slope to a greater degree than the presence of collagen in the ovine model of CMI. In addition, Arrhythmogenic Right Ventricular Dysplasia (ARVD), in which a congenitally absent myocardium of the right ventricle may be partially or completely replaced by adipose and fibrous tissue, is also known to carry the risk of SCD from mVAs. The mechanism is related to the localised lipomatous infiltrates in the region of conducting system causing an actual delay in the intraventricular transmission of impulses, with the subsequent development of re-entrant ventricular arrhythmias. Similarly, large scar volume is not critical for the development of life-threatening arrhythmias in ARVD with ventricular adiposity.

To date, the substrate underlying LM post-AMI is unknown. Hence, there is a critical need to identify novel substrates of LM that can function as potential therapeutic targets.

Diagnostic and Treatment Methods of the Invention

The invention is directed to methods for diagnosing reperfusion and/or non-reperfusion hemorrhage in a subject in need thereof. The method comprises obtaining images of the subject's heart, detecting regional iron oxide deposits in the heart, and diagnosing presence or absence of reperfusion and/or non-reperfusion hemorrhage in the subject. The presence of iron oxide deposits in regions of the heart is indicative of reperfusion and/or non-reperfusion hemorrhage in the subject. Alternatively, an increase in the iron oxide deposition in regions of the subject's heart compared to the control subject is indicative of reperfusion and/or non-reperfusion hemorrhage in the subject. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxgenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction in the subject (Okuhara et al., Change in bilirubin level following acute myocardial infarction is an index for heme oxygenase activation *South Med J.* 2010 September; 103(9):876-81; *Peptides* 2010 September; 31(9):1786-90. Epub 2010 May 27). In one embodiment, the subject is a myocardial infarction patient that has undergone reperfusion. In another embodiment, the subject is a myocardial infarction patient that has not undergone reperfusion.

The invention also provides methods for diagnosing myocardial hemorrhage in subjects that are treated with anti-platelet drugs and/or anticoagulant drugs. In some embodiments, the side-effects of antiplatelets and/or anticoagulants include subjects later developing hemorrhagic infarctions resulting in increased risk of cardiac arrhythmias and/or heart failure. Accordingly, the method comprises obtaining images of the subject's heart, detecting regional iron oxide deposits in the heart, and diagnosing presence or absence of myocardial hemorrhage associated wherein the subject is or was administered antiplatelet drugs and/or anticoagulant drugs. The presence of iron oxide deposits in regions of the heart is indicative of myocardial hemorrhaging in the subject. Alternatively, an increase in the iron oxide deposition in regions of the subject's heart compared to the control subject is indicative of myocardial hemorrhaging in the subject. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxgenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction in the subject, wherein the subject is or was administered antiplatelet drugs and/or anticoagulant drugs. In some embodiments, myocardial hemorrhaging in subjects that were or are administered antiplatelet drugs and/or anticoagulant drugs, is indicative of increased risk of cardiac arrhythmias and/or heart failure.

The invention also provides methods for predicting cardiac arrhythmias in a subject in need thereof comprising. The method for predicting cardiac arrhythmias includes diagnosing reperfusion and/or non-reperfusion hemorrhage in the subject comprising obtaining images of the subject's heart, detecting regional iron oxide deposition in the heart, and diagnosing presence or absence of reperfusion and/or non-reperfusion hemorrhage in the subject. The presence of iron oxide deposits in regions of the subject's heart is indicative of reperfusion and/or non-reperfusion hemorrhage in the subject. The presence of reperfusion and/or non-reperfusion hemorrhage in the subject is indicative of increased likelihood of cardiac arrhythmias. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxgenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction and increased likelihood of cardiac arrhythmias in the subject. In one embodiment, the subject is a myocardial infarction patient that has undergone reperfusion. In another embodiment, the subject is a myocardial infarction patient that has not undergone reperfusion.

The invention also provides methods for predicting sudden cardiac death in a subject in need thereof. The method comprises diagnosing reperfusion and/or non-reperfusion hemorrhage and/or detecting regional iron oxide deposits in the subject's heart by the methods described above. In an embodiment, the methods comprise obtaining images of the subject's heart, detecting regional iron oxide deposits in the heart, and diagnosing presence or absence of reperfusion and/or non-reperfusion hemorrhage in the subject. The presence of iron oxide deposits in regions of the subject's heart is indicative of reperfusion and/or non-reperfusion hemorrhage in the subject and therefore is indicative of increased likelihood of sudden cardiac death or cardiac arrhythmias in the subject. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxgenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction, increased likelihood of sudden cardiac death and/or cardiac arrhythmias in the subject. In one embodiment, the subject is a myocardial infarction patient that has undergone reperfusion. In another embodiment, the subject is a myocardial infarction patient that has not undergone reperfusion.

Also provided is a method for determining the prognosis after a myocardial infarction in a subject in need thereof. The method comprises diagnosing reperfusion/non-reperfusion hemorrhage and/or regional iron oxide deposits in the subject's heart by the methods described above. In one embodiment, the presence of reperfusion/non-reperfusion hemorrhage and/or regional iron oxide deposit in the subject is indicative of a poor prognosis. In another embodiment, increased reperfusion/non-reperfusion hemorrhage and/or regional iron oxide deposit in the subject compared to the control subject is indicative of poor prognosis. In some embodiments, the method further comprises measuring blood and/or serum levels of any one or more of hepcidin, carbon monoxide, bilirubin, unbound iron binding capacity (UIBC), Fe bound to transferrin, ferritin, heme (heam) oxgenase, biliverdin or a combination thereof in the subject. An increase in any one or more of hepcidin, biliverdin, bilirubin, carbon monoxide, heme (haem) oxygenase, Fe bound to transferrin, ferritin and/or a decrease in UIBC is indicative of hemorrhagic infarction and poor prognosis in the subject. In one embodiment, the subject is a myocardial infarction patient that has undergone reperfusion. In another embodiment, the subject is a myocardial infarction patient that has not undergone reperfusion.

Additionally, the invention provides methods for treating a subject at an increased risk of sudden cardiac death. The method comprises administering an effective amount of a chelating agent to the subject so as to treat the subject at an increased risk of sudden cardiac death. In an embodiment, an increased risk of sudden cardiac death is associated with one or more regional iron deposits in the heart. In an embodiment, carbon monoxide therapies and other haem-oxygenase regulating drugs may also be used to treat or prevent deposition of iron oxide. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker. In one embodiment, the subject is a myocardial infarction patient that has undergone reperfusion. In another embodiment, the subject is a myocardial infarction patient that has not undergone reperfusion.

The invention further provides a method for treating a subject with localized deposits of iron oxide in myocardial tissue. The method includes obtaining MRI images of the subject's heart, detecting localized iron oxide deposition in the heart, providing a composition comprising a chelating agent and administering an effective amount of the composition to the subject so as to treat a subject with localized deposition of iron in the myocardial tissue. In some embodiments, the localized deposition of iron in the myocardial tissue results in cardiac arrhythmia. In some embodiments, cardiac arrhythmia is atrial fibrillation and ventricular arrhythmia. In various embodiments, atrial arrhythmia includes but is not limited to atrial fibrillation, atrial flutter and/or a combination thereof and ventricular arrhythmia includes but is not limited to ventricular tachycardia, ventricular fibrillation, bundle-branch block, A-V block, and/or a combination thereof. In an embodiment, carbon monoxide therapies and other haem-oxygenase regulating drugs may also be used to remove iron oxide deposits. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker. In one embodiment, the subject is a myocardial infarction patient that has undergone reperfusion. In another embodiment, the subject is a myocardial infarction patient that has not undergone reperfusion.

The invention further provides methods for treating a subject with electrical conduction abnormalities and/or mechanical abnormalities in the myocardium. In an embodiment, the electrical conduction abnormalities and/or mechanical abnormalities are due to localized deposits of iron oxide in the myocardium. The treatment method includes obtaining MRI images of the subject's heart, detecting localized iron oxide deposition in the heart, providing a composition comprising a chelating agent and administering an effective amount of the composition to the subject so as to treat a subject with electrical conduction abnormalities and/or mechanical abnormalities in the myocardium. In an embodiment, carbon monoxide therapies and other haem-oxygenase regulating drugs may also be used to remove iron oxide deposits. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker. In one embodiment, the subject is a myocardial infarction patient that has undergone reperfusion. In another embodiment, the subject is a myocardial infarction patient that has not undergone reperfusion.

The invention further provides a method for reducing myocardial inflammation in subjects in need thereof. The method includes obtaining MRI images of the subject's heart, detecting regional iron oxide deposits in the heart, wherein presence of iron oxide deposits is indicative of increased myocardial inflammation; and administering an effective amount of a composition comprising a chelating agent so as to reduce myocardial inflammation in the subject. In an embodiment, the subject has undergone one or more hemorrhagic infarctions resulting in myocardial inflammation. In an embodiment, carbon monoxide therapies and other haem-oxygenase regulating drugs may also be used to remove iron oxide deposits. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker. In one embodiment, the subject is a myocardial infarction patient that has undergone reperfusion. In another embodiment, the subject is a myocardial infarction patient that has not undergone reperfusion.

The invention also provides a method for reducing adverse remodeling of the heart in subject in need thereof. The method includes obtaining MRI images of the subject's heart, detecting regional iron oxide deposits in the heart, wherein presence of iron oxide deposits is indicative of increased myocardial inflammation; and administering an effective amount of a composition comprising a chelating agent so as to reduce myocardial inflammation in the subject and thereby reducing the adverse remodeling of the heart. In an embodiment, the subject has undergone one or more hemorrhagic infarctions resulting in myocardial inflammation. In an embodiment, carbon monoxide therapies and other haem-oxygenase regulating drugs may also be used to prevent iron deposition. Carbon monoxide therapies and haem-oxygenase regulating drugs may be used alone or in conjunction with chelation therapies to augment the prevention/reduction of iron in myocardial tissue. In one embodiment, the subject is a myocardial infarction patient that has undergone reperfusion. In another embodiment, the subject is a myocardial infarction patient that has not undergone reperfusion.

The invention also provides a method for predicting cardiac arrhythmias in a subject in need thereof. The method includes obtaining MRI images of the subject's heart and detecting regional iron oxide deposits in the heart. In an embodiment, the subject has not undergone a myocardial infarction. The presence of iron oxide deposits in one or more regions of the heart is indicative of increased likelihood of cardiac arrhythmia in the subject, so as to predict cardiac arrhythmia in the subject. In one embodiment, the subject is a myocardial infarction patient that has undergone reperfusion. In another embodiment, the subject is a myocardial infarction patient that has not undergone reperfusion.

In various embodiments of the invention, the subject is any one or more of myocardial infarction patient, a patient with ischemic heart disease, a patient with chronic iron deposition in the heart or a combination thereof. In some embodiments, the subject is a myocardial infarction patient whose treatment is initiated at least 2 hours, at least 3 hours, at least 4 hours, at least 5 hours or at least 6 hours after the onset of symptoms of myocardial infarction. In a further embodiment, the symptoms of onset of myocardial infarction are any one or more of chest pain, elevated ST segment in an electrocardiogram (ECG), elevated troponin levels in the blood or a combination thereof.

In some embodiments, the images for the methods of the invention are obtained using Magnetic Resonance Imaging (MRI) or Computed Tomography (CT). In an embodiment, the images for the methods of the invention are obtained using MRI.

In some embodiments, images may be obtained 4-24 hours post-reperfused or non-reperfused MI, 1-5 days post reperfused or non-reperfused MI, 5-10 days post reperfused or non-reperfused MI, 10-15 days post reperfused or non-reperfused MI, 15-20 days post reperfused or non-reperfused MI, 20-25 days post reperfused or non-reperfused MI and/or 25-30 days post reperfused or non-reperfused MI. Images may also be acquired in the chronic period following infarction, several months post MI for detection of chronic iron deposition.

In a further embodiment, iron levels at or above 0.04 mg/g of tissue within infarcted myocardium is indicative of hemorrhagic infarction in the subject.

In one embodiment, the chelating agent may be any one or more of Deferoxamine, Deferasirox, Deferiprone or a combination thereof. In another embodiment, the chelating agents (for example Deferoxamine, Deferasirox, Deferiprone) may be used at a dose of any one or more of 100-200 mg/day, 200-300 mg/day, 300-400 mg/day, 400-500 mg/day, 500-600 mg/day, 600-700 mg/day, 700-800 mg/day, 800-900 mg/day, 900-100 mg/day or a combination thereof. The chelating agent may be administered intramuscularly (IM). If more than one chelating agent is used, each chelating agent may be administered concurrently or sequentially. A person of ordinary skill in the art would know the optimum chelating agent that may be used for iron oxide removal and the optimum dosage of the one or more chelating agents that may be used for iron oxide removal.

In some embodiments, carbon monoxide therapies and other haem-oxygenase regulating drugs may also be used to prevent iron deposition in myocardium (Motterlini R, Otterbein L E, Therapeutic Potential of Carbon Monoxide, *Nature*, 2010 September; 9(9):728-43; Pamplona et al., Heme oxygenase-1 and carbon monoxide suppress the pathogenesis of experimental cerebral malaria, 2007 *Nature Medicine* Vol 13, 703-710). Carbon monoxide therapies and haem-oxygenase regulating drugs may be used alone or in conjunction with chelation therapies to augment the prevention/reduction of iron in myocardial tissue. In an embodiment, carbon monoxide therapies and other haem-oxygenase regulating drugs may also be used to remove iron oxide deposits. Carbon monoxide therapies and haem-oxygenase regulating drugs may be used alone or in conjunction with chelation therapies to augment the prevention/reduction of iron in myocardial tissue. In some embodiments, subjects with iron oxide deposits are implanted with an implantable cardioverter-defibrillator (ICD) or a pacemaker.

Carbon monoxide (CO) and haem-oxygenase regulating drugs may be administered via inhalational, intraperitoneally (i.p), intravenously (i.v), orally (p.o), and/or topically. In some embodiments, the dosage of carbon monoxide is such that the carboxyhemoglobin levels do not exceed 20%. The amount of CO administered may be any one or more of 0.1-0.5 ppm, 0.5-5 ppm, 5-50 ppm, 50-100 ppm, 100-200 ppm, 200-300 ppm 300-400 ppm, 0.1-400 ppm or a combination thereof.

In an additional embodiment, the subject is any one or more of human, monkey, ape, dog, cat, cow, horse, goat, pig, rabbit, mouse and rat.

One of the major complications associated with myocardial infarctions is post-infarct remodeling of the heart, which in time culminates in heart failure. The inventor hypothesizes that one of the key factors that drive an infarcted heart into heart failure is the presentation of iron from biodegradation of intramyocardial hemorrhage. Elevated tissue deposition of iron is expected to increase oxidative stress to the myocardium resulting in increased tissue necrosis in the acute phase of the infarction. In response, the remodeling of the heart in the post-infarct period is accelerated compared to infarctions that are non-hemorrhagic.

Since MRI can be used to determine whether reperfusion therapy or no reperfusion has led to hemorrhage, the imaging information can be used to evaluate improved reperfusion strategies that pre-emptively limit hemorrhage and/or aid in chelation (or other medical) therapies aimed at preventing the iron from hemorrhagic infarction in the post-reperfusion phase.

Advantages of the Invention

This invention provides a method for classifying an infarction (both reperfused and non-reperfused types) to be hemorrhagic or non-hemorrhagic based on MRI in order to provide therapeutic interventions to prevent iron deposition in the chronic period of infarction. In addition it also provides a means to verify whether the therapeutic intervention was effective in preventing hemorrhagic infarction, subsequent iron deposition, or serial imaging to determine the rate of clearance of iron deposition.

Many variations and alternative elements have been disclosed in embodiments of the present invention. Still further variations and alternate elements will be apparent to one of skill in the art. Among these variations, without limitation, are the selection of constituent modules for the inventive methods, compositions, kits, and systems, and the various conditions, diseases, and disorders that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1 Experimental Methods

Surgical Procedure

Figure 10:
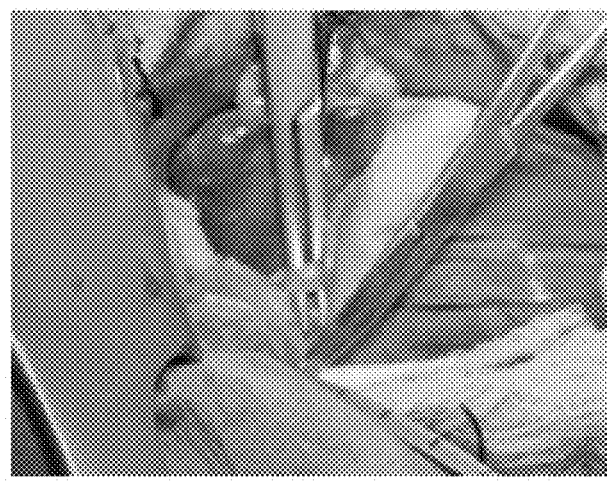
FIG. 10 depicts, in accordance with various embodiments of the present invention, the isolation of left anterior descending (LAD) artery for the placement of hydraulic occluder.

Canines (n=23, 20-25 kg) were enrolled and studied according to the protocols approved by the Institutional Animal Care and Use Committee. Each dog was given an intramuscular injection of the pre-anesthetic tranquilizer Innovar (0.4 mg/ml of fentanyl and 20 mg/ml of droperidol) at a dose of 1 ml/25-50 kg of body weight. Subsequently, the dog was anesthetized with an intravenous injection of Propofol (5.0-7.5 mg/kg), endotracheally intubated and maintained on gas anesthesia (2.0-2.5% isoflurane with 100% oxygen). Animals were artificially ventilated at 1-2 L/min with the respiration rate being continuously adjusted to maintain partial pressure of $CO_2$ in blood ($PaCO_2$) between 30 and 35 mmHg. Left lateral thoracotomy was performed at the fourth intercostal space, and the exposed heart was suspended in a pericardial cradle (FIG. 10). Aortic and left atrial catheters were inserted and secured for invasive blood pressure monitoring and drug delivery. A portion of the proximal left anterior descending artery (LAD) was isolated and a hydraulic occluder was looped around the vessel 1.0-1.5 cm distal to the bifurcation of left main coronary artery. A Doppler ultrasound flow probe (Crystal Biotech, Northborough, Mass.) was circumferentially secured 2.0-2.5 cm downstream from the occluder to verify the fidelity of occlusion. Systemic $O_2$ saturation, $PaCO_2$, body temperature, blood pressure, respiration rate, heart rhythm and rate were continuously monitored throughout the surgery. The chest was closed and the dog was allowed to recover for 7 days prior to I/R injury.

Inducing Ischemia-Reperfusion Injury

On day 7 post-surgery, each dog was anesthetized and reversible LAD stenosis was induced by gently forcing saline through the open end of the occluder tubing using a micro-push syringe (250 μl GASTIGHT syringe, Hamilton Company, Reno, Nev.) resulting in the constriction of LAD. The extent of LAD occlusion was continuously monitored by Doppler flow velocities. After achieving complete LAD occlusion, the ballooned tubing was clamped and held for 3 hours. At the end of 3 hours of ischemia, reperfusion was established by releasing the clamp and completely drawing out the saline from the tubing. Vital parameters, similar to those described earlier for the surgical procedure, were continuously monitored. To minimize fatal ventricular arrhythmias from I/R injury, all dogs were pre-treated with Amiodarone (200 mg/day, TEVA Pharmaceuticals USA, Sellersville, Pa.) for 2 weeks prior to I/R injury. Arrhythmias occurring during the ischemia and reperfusion were controlled by intravenous injection of 1-2 ml lidocaine (20 mg/ml) as needed.

Experimental Groups

All animals underwent proton Magnetic Resonance Imaging ($^1$H-MRI) on days 3 (acute) and 56 (chronic) following I/R injury, unless noted otherwise. Four dogs died within the first 2 hours of establishing reperfusion (despite resuscitation efforts) and in two dogs, reperfusion was not established due to the failure of occluder implementation. The remaining dogs were assigned to two different groups—Controls (n=3) and Infarcted (n=14). The control group underwent the surgical procedure (shams), but was not subjected to I/R injury. The infarcted group underwent 3 hours of no-flow ischemia followed by reperfusion. Among the infarcted dogs, three dogs were sacrificed on day 3 for histological validation of acute hemorrhagic infarctions. All the results (except histological evidence for acute hemorrhagic infarctions) were obtained from the remaining 11 dogs of the infarcted group and 3 dogs of the control group that were sacrificed immediately following the chronic phase MRI study.

In-Vivo $^1$H-MRI Studies

All $^1$H-MRI studies on animals were performed on a clinical 1.5 T MRI system (MAGNETOM Espree, Siemens Medical Solutions, Erlangen, Germany) equipped with a high-performance gradient system (maximum gradient amplitude of 40 mT/m, maximum slew rate of 200 T/m/s). The animals were anesthetized, intubated and ventilated as described before for the surgical procedure. They were placed on the scanner table in feet-first, right anterior position. A flexible eight-channel phased-array surface coil was placed on their chests for signal reception. $B_1$ field changes were transmitted using the scanner's integrated body coil. Scout images were acquired to localize the heart and a volume-selective shim covering the whole heart was performed to minimize off-resonance artifacts. Multiple cardiac-gated breath-held 2D images of contiguous short-axis sections covering the entire left-ventricle (LV) and the three long-axis views (2 chamber, 3 chamber and 4 chamber) were acquired using cardiac phase resolved SSFP (cine-SSFP), T2*-weighted imaging and Late Enhancement (LE) imaging. Multi-gradient echo (T2*-weighted) and LGE images were acquired at mid-diastole when the cardiac motion is minimal. Cardiac gating was achieved by using prospective ECG triggering and breath-holding was achieved by suspending ventilation at end-expiration. Anesthesia was carefully controlled during breath-holding to avoid any spontaneous breathing. A 2-3 minute rest period between successive breath-holds was given to maintain the heart rate at a constant level throughout all acquisitions.

Cardiac wall motion was visually assessed using cine-SSFP images. Typically used cine imaging parameters were TR/TE=3.5/1.75 ms, flip angle=70°, 20-25 cardiac phases per imaging section and readout bandwidth (BW)=930 Hz/pixel. Significant wall motion abnormalities were observed in the LAD territories of infarcted dogs both during acute and chronic phase MRI studies. Acute hemorrhage and chronic iron loading were evaluated using T2*-weighted images acquired by a multiple gradient-echo sequence. Typically used imaging parameters were TR=220 ms, 12 echoes with TEs=3.4, 6.4, 9.4, 12.4, 15.4, 18.4, 21.4, 24.3, 27.3, 30.3, 33.3 and 36.3 ms, flip angle=12° and BW=566 Hz/pixel. All in-vivo imaging studies were terminated with the acquisition of Phase-Sensitive Inversion Recovery LGE images using a non-selective inversion recovery (IR) prepared SSFP sequence. Initially, 0.2 mmol/kg of Gadolinium-DTPA contrast agent (Magnevist, Bayer Healthcare Pharmaceuticals Inc., Wayne, N.J.) was administered intravenously using a power injector followed by a 10 ml saline flush. An optimal inversion time (TI) to null the apparent normal myocardium was then determined from TI scout images. LGE images were acquired 10-15 minutes after contrast administration using the following imaging parameters: TR/TE=3.5/1.75 ms, flip angle=400 and BW=1002 Hz/pixel. Other commonly used imaging parameters for all the scans were Field-of-view (FOV)=166 mm×280 mm, imaging matrix=116×192, imaging section thickness=8 mm and number of averages=1. FOV was rectangular for all the scans. No image acceleration methods were used.

All animals in the infarcted group sustained acute hemorrhagic infarctions as indicated by the acute phase T2*-weighted and LGE images. All animals in the control group did not sustain any myocardial infarction throughout the study as verified by both acute and chronic phase LGE images.

Ex-Vivo $^1$H-MRI Studies

Animals were euthanized immediately after the chronic phase MRI study by intravenously administering 0.2 ml/kg body weight of Euthasol (390 mg/ml sodium pentobarbital and 50 mg/ml phenytoin sodium) and their hearts were excised. Each heart was manually sliced into 1 cm thick slices along the LV short-axis. Each slice was immersed in 0.05M Phosphate-buffered saline (PBS; pH=7.4) and ex-vivo 2D T2*-weighted and Phase-Sensitive Inversion Recovery LGE images were acquired using a multiple gradient-echo sequence and IR-prepared SSFP sequence respectively. A head coil was used for signal reception for ex-vivo imaging. Typical imaging parameters used for ex-vivo T2*-weighted and LGE images were the same as those used for the corresponding in-vivo T2*-weighted and LGE images. The imaging section was carefully selected to avoid any partial-voluming between the myocardial tissue and the PBS bath. FOV was rectangular and no image acceleration method was used.

Patient $^1$H-MRI Studies $^1$H-MRI studies were performed on patients (n=15, 3 females) according to the protocols approved by the Institutional Review Board. Patients with acute ST-elevated myocardial infarction meeting American Heart Association diagnostic criteria were enrolled in the study only if successful percutaneous coronary intervention (PCI) was performed within 12 hours of the onset of symptoms. Patients were excluded from the study if they had previous myocardial infarctions or were contraindicated for a cardiac MRI study. All enrolled patients underwent $^1$H-MRI 3 days after successful PCI and again at 6 months after initial enrollment.

All patient imaging studies were performed on a clinical 1.5 T MRI system (MAGNETOM Avanto, Siemens Medical Solutions, Erlangen, Germany) equipped with high-performance gradient system (maximum gradient amplitude of 45 mT/m and maximum slew rate of 200 T/m/s). $B_1$ field was transmitted using the scanner's integrated body coil and an eight-channel flexible phased-array coil was placed on the chest for signal reception. All anatomical axes were localized and a volume-selective shim covering the whole heart was performed. Contiguous short-axis sections covering the entire LV along with 2, 3 and 4 chamber long-axis views of the heart were acquired at mid-diastole using cine-SSFP, Multi-gradient echo (T2*-weighted) and LGE imaging. Typical imaging parameters used for cine-SSFP images were TR/TE=3.32/1.16 ms, flip angle=65°, BW=930 Hz/pixel, 25 cardiac phases, FOV=340 mm×276 mm, imaging matrix=192×156, imaging section thickness=10 mm and number of averages=1. T2*-weighted images were acquired using a multiple gradient-echo technique. Typical imaging parameters used for T2*-weighted images were TR=240 ms, 8 echoes with TEs=2.6, 4.8, 7.0, 9.3, 11.5, 13.7, 16.0 and 18.2 ms, flip angle=10°, BW=355 Hz/pixel, FOV=420 mm×328 mm, imaging matrix=256×200, imaging section thickness=10 mm and number of averages=1. LGE images were acquired 10-15 minutes after an intravenous Gadolinium-DTPA administration (0.2 mmol/kg of body weight) using an optimal TI to suppress signal from remote myocardium. An IR-prepared fast low angle shot (FLASH) sequence was employed with the typical imaging parameters being TR=1 R-R interval, TE=3.32 ms, BW=235 Hz/pixel, FOV=400 mm×300 mm, imaging matrix=256×192, imaging section thickness=10 mm and number of averages=1. FOVs were rectangular and no image acceleration method was used.

Gross Histological Identification of Myocardial Infarcts

All ex-vivo myocardial slices from every animal were stained with triphenyltetrazolium chloride (TTC) to histochemically validate irreversible myocardial damage and delineate the infarcted territories from the viable myocardium. TTC stains viable myocardium brick-red as membrane-bound dehydrogenases and other cofactors reduce the tetrazolium salts to a brick-red formazan pigment, while infarcted myocardium remains unstained. Briefly, the slices were incubated in 1% (w/v) TTC in PBS at 37° C. for 15-20 minutes and photographed under room light. Chronic iron overloading appears yellowish-brown within the pale infarcted territories. All infarcted dogs contained a number of slices with TTC-unstained infarct regions within the LAD territory of LV. Few slices were negative for infarction and were discarded. All slices from the control dogs were negative for infarction.

Semi-Automatic In-Vivo Image Analysis

All in-vivo image analyses (both acute and chronic from animals and patients) were performed off-line using validated and certified cardiac MR image processing software (cmr$^{42}$, Circle Cardiovascular Imaging Inc., Calgary, AB, Canada). To minimize unwanted off-resonance and flow artifacts, in-vivo T2* maps were constructed by fitting the multi-echo data from only the first 6 echoes (TEs from 3.4-18.4 ms for animals and 2.6-13.7 ms for patients) to a mono-exponential decay. Endocardial and epicardial contours were drawn for each imaging section on the cine-SSFP image corresponding to the appropriate mid-diastolic phase. The contours were then copied on to both T2*-weighted and LGE images and adjusted when necessary. Remote myocardium was identified as the region showing no hyperintensity on LGE images. A reference region-of-interest (ROI) was drawn in the remote myocardium and a threshold based semi-automatic method was used to detect infarcted myocardium on LGE images. Infarcted myocardium was defined as the hyperintense region on LGE images with ≥10 adjacent pixels having mean signal intensity (SI) 5 standard deviations (SD) greater than the mean SI of reference ROI (45).

In the final analysis of infarcted myocardium on LGE images, regions of hypointense territories (microvascular obstruction) within the hyperintense territories were manually included. Refer to FIGS. 11A-11E.

Figure 13:
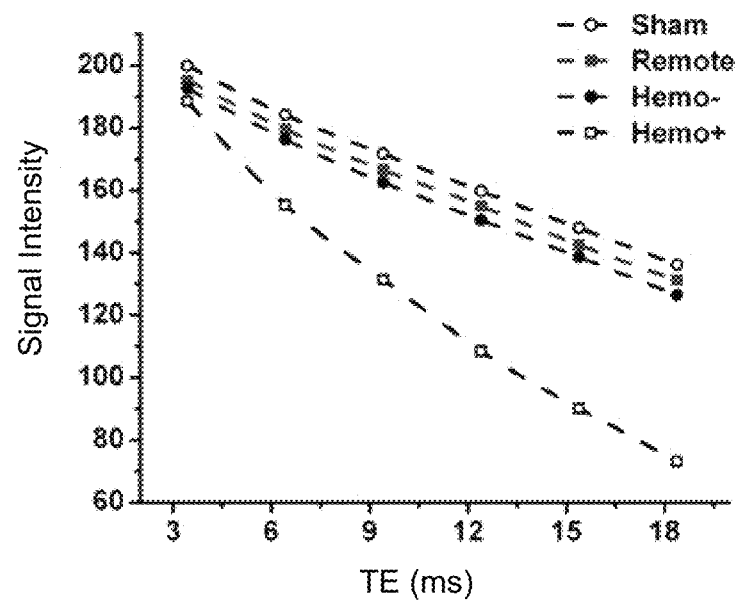
FIG. 13 depicts, in accordance with various embodiments of the present invention, the monoexponential fits of multi-echo data from T2*-weighted images. Representative mono-exponential fits for Sham (T2*=42.1 ms), Remote (T2*=40.7 ms), Hemo+(T2*=19.1 ms) and Hemo−(T2*=39.6 ms) myocardium are shown.

The reference ROI from the LGE image was copied on to the T2*-weighted image acquired at the longest TE among all the echoes used to construct the T2* map (FIG. 13), i.e. TE=18.4 ms for animals and TE=13.7 ms for patients. Hemorrhagic myocardium was identified on this image as the hypointense region with ≥10 adjacent pixels having mean SI at least 2 SDs below the mean SI of the reference ROI (46). While drawing the reference ROI and in the final analysis of the hemorrhagic myocardium, care was taken not to include regions affected by blooming artifacts arising from susceptibility shifts at the heart-lung interface. Also, any hypo-intense region lying outside the infarcted territory was excluded from the analysis.

Classification of In-Vivo Imaging Sections

For animals, all in-vivo imaging sections were divided into three different groups based on in-vivo LGE and T2*-weighted images. Myocardial imaging sections that contained hyper-intense LAD infarct regions on LGE images with a hemorrhagic core on the corresponding T2*-weighted images were classified as hemorrhagic infarct sections. Similarly, imaging sections that contained LAD infarct regions on LGE images but no hemorrhagic core on the corresponding T2*-weighted images were classified as non-hemorrhagic infarct sections. Imaging sections that did not contain any infarcted regions were not used for further analysis. Imaging sections from the control dogs (no patients) were classified as Sham. Mean per-section in-vivo T2* values were measured for hemorrhagic infarct (Hemo+), non-hemorrhagic infarct (Hemo−), remote myocardium (Remote) and sham myocardium (Sham) from the corresponding T2* maps (in-vivo T2*section). Also, mean whole-heart in-vivo T2* values were measured for each heart from Hemo+, Hemo−, Remote and Sham groups by averaging across the corresponding imaging sections (in-vivo T2*heart).

For patients, a similar classification of in-vivo imaging sections was used and in-vivo T2* values on a per-section and whole-heart basis were measured for Hemo+, Hemo− and remote groups (no shams) from the corresponding T2* maps.

Semi-Automatic Ex-Vivo Image Analysis and Classification

All ex-vivo image analysis was also performed offline using cmr[42]. T2* maps for each ex-vivo myocardial slice from all the animals were constructed by fitting multi-echo data from only the first 6 echoes (TEs 3.4-18.4 ms) to a mono-exponential decay. Remote myocardium was defined as the region stained brick-red by TTC along with the absence of hyperintensity on ex-vivo LGE image. A reference ROI was drawn within the remote myocardium on LGE image and infarcted myocardium was defined as the region with ≥10 adjacent pixels having mean SI at least 5 SDs above the mean SI of the reference ROI. Subsequently, the reference ROI was copied on to the T2*-weighted image acquired at TE=18.4 ms. Hemorrhagic myocardium was defined as the region with ≥10 adjacent pixels having a mean SI at least 2 SDs below the mean SI of the reference ROI.

On the basis of ex-vivo LGE and T2*-weighted images, as well as corresponding TTC staining, all ex-vivo myocardial slices were also classified as sham, hemorrhagic infarct or non-hemorrhagic infarct slices as earlier (refer to in-vivo image analysis). Excellent correlation between TTC-unstained infarcted region and hyperintense infarcted region on LGE images was observed. Slices from the infarcted dogs that did not contain TTC-unstained infarcted regions or hyperintense regions on corresponding ex-vivo LGE images were discarded. Mean per-slice ex-vivo T2* values for hemorrhagic infarcts (Hemo+), non-hemorrhagic infarcts (Hemo−), remote myocardium (Remote) and sham slices (Sham) were measured from T2* maps (ex-vivo T2*$_{slice}$). Also, mean whole-heart ex-vivo T2* values for each dog were measured for Hemo+, Hemo−, Remote and Sham groups by averaging across all the corresponding slices (ex-vivo T2*$_{heart}$).

Isolation of Tissue Samples

From both ex-vivo hemorrhagic and non-hemorrhagic infarct slices, unstained TTC sections (only from the densely infarcted areas) were carefully cut out. Care was taken not to cut into the infarct border zone or any surrounding TTC-stained viable myocardium. To accommodate further tissue analysis, all blocks of hemorrhagic and non-hemorrhagic infarcts were further cut into their constituent smaller hemorrhagic (Hemo+) and non-hemorrhagic (Hemo−) infarct samples (0.5-0.8 cm$^3$). Similarly, from each hemorrhagic and non-hemorrhagic infarct slice, at least 2 samples of TTC-stained viable myocardium were cut out (Remote). From each sham slice (obtained from control dogs), at least two samples of TTC-stained normal myocardium were cut out (Sham). An average of 30 myocardial samples was obtained from each infarcted dog; while an average of 10 samples was obtained from each control dog. In all nearly 360 samples were obtained and analyzed for the entire study.

Histopathological Studies

A representative myocardial sample from each of the Hemo+, Hemo−, Remote and Sham groups was obtained from every infarcted and control dog. The sample was dehydrated, embedded in a paraffin block and three contiguous 5 μm sections were obtained using a microtome. The three sections were stained with regressive Hematoxylin and Eosin (H & E), Masson's Trichrome and Perl's stains respectively using standard techniques. The sections were mounted on glass slides and scanned at 100× magnification using an ACIS II technology based ChromaVision digital slide scanner (Clarient Inc., Aliso Viejo, Calif.). The slides were also imaged at 400× magnification using an Olympus BX41 stereo compound microscope with dual view side (Olympus America Inc., Center Valley, Pa.).

H&E staining was used to distinguish between necrotic and viable myocardium. Hematoxylin stained nuclei of viable cells blue, while eosin stained the cytoplasmic structures pinkish red. Acute infarcted myocardium showed massive infiltration of inflammatory cells. Extravasated red blood cells (eosinophilic structures) in hemorrhagic infarctions were stained intensely red by eosin. Chronic infarcted myocardium was stained faint pink with no distinctly visible individual cells.

Masson's trichrome staining was used to identify collagen deposition within the infarcted myocardium. Viable myocardium was stained dark red, while collagenous scar was stained intensely blue. Perl's staining was used to visually identify iron deposition within the infarcted myocardium. Iron deposits externalized from the extravasated red blood cells were stained blue, while cells and cytoplasmic structures were stained pink.

Capacitor Cell Design and Electrical Impedance Measurements

Bulk electrical impedance of each tissue sample from Hemo+, Hemo−, Remote and Sham groups were measured using two-terminal electrode technique as previously described by Schwan (*Physical techniques in biological research. Volume VI, Electrophysiological methods*. Part B, W. L. Nastuk, Ed. (Academic Press, New York; London, 1963), pp. 323-407.). A capacitor cell, with a variable electrode distance similar to that described by Schwartzman et al (*J Interv Card Electrophysiol* 3, 213 October, 1999), was designed to measure bulk electrical impedance of each sample using alternating-current (AC) impedance spectroscopy. The capacitor cell consisted of a transparent tubular glycol-modified polyethylene teraphthalate (PETG) body that is closed at one end and fitted with a removable Delrin cap at the other end. Two square silver electrodes, each of 1.5 cm² surface area, were enclosed in the tubular body. One electrode was affixed to the closed end, while the other electrode was affixed to a PETG disk that can move through the tubular body. The electrodes were soldered to the inner conductors of copper coaxial cables, which in turn were connected to the analyzer. The outer conductors were connected to electrical ground.

Each sample was incubated at 37° C. for 15 minutes prior to use. The sample was then sandwiched between the two electrodes of the capacitor cell and 10 μA of alternating current was passed parallel to the myocardial fibers. The voltage that developed across the sample was measured using Solartron 1260 impedance/gain-phase analyzer (Solartron Instruments, Hampshire, UK) and acquired using ZPlot data acquisition software. The induced voltage was divided by the current passed to derive the complex AC-impedance (Z in ohms) of the sample. The impedance values were measured at frequencies ranging from 100 Hz to 10 MHz with 10 measurements in each frequency decade. Stray effects in the measurements were corrected using methods described by Schwan (above). To minimize the effects of α-dispersion (Schwan and Kay, *Ann N Y Acad Sci* 65, 1007 Aug. 9, 1957) (occurring around 100 MHz) and undesired myocardial sample preparation errors (such as an inhomogeneous sample containing both infarct region and surrounding viable myocardium), all analysis was limited to impedance data acquired at 1 MHz.

Normalized Conductivity and Permittivity Measurements

Bulk electrical permittivity and conductivity of each sample were derived from the AC-impedance measurements. Surface area (A in m²) and distance between the electrodes (d in m) after the sample is placed between the electrodes were measured. The complex admittance Y (in Siemens S) of the sample was calculated as the reciprocal of Z, which can be further expressed as follows (S. Grimnes, M. Ø. G., in *Bioelectricity and Bioimpedance Basics*. (Academic Press, London, U. K., 2008), pp. 57-92)

$$Y = G + i\omega C$$

where G is the conductance (in S), C is the capacitance (in F), ω is the angular frequency (in rad/s) and i is $\sqrt{-1}$. G and C can be further expressed as follows $$G = \frac{A \times \sigma}{d}$$

$$C = \frac{A \times \varepsilon}{d}$$

where σ and ε are bulk conductivity (in S/m) and permittivity (in F/m) respectively. Bulk σ and ε of each sample were therefore calculated from the original complex impedance data (Z) as follows $$\sigma = \frac{\operatorname{Re}\left(\frac{1}{Z}\right) \times d}{A}$$

-continued $$\varepsilon = \frac{\operatorname{Im}\left(\frac{1}{Z}\right) \times d}{A \times \omega}$$

For a given heart from an infarcted dog, mean conductivity ($\sigma'_{Remote}$) and permittivity ($\varepsilon'_{Remote}$) of its remote myocardium were calculated by weight-averaging the conductivities and permittivities of all its constituent remote samples as follows $$\sigma'_{Remote} = \frac{\Sigma(\sigma_{Remote} \times W_{Remote})}{\Sigma W_{Remote}}$$

$$\varepsilon'_{Remote} = \frac{\Sigma(\varepsilon_{Remote} \times W_{Remote})}{\Sigma W_{Remote}}$$

where $\sigma_{Remote}$ and $\varepsilon_{Remote}$ are the individual conductivity and permittivity of each constituent remote sample of a heart and $W_{Remote}$ is its corresponding sample weight. Normalized conductivity ($\overline{\sigma}_{sample}$) and permittivity ($\overline{\varepsilon}_{sample}$) of each Hemo+, Hemo− and Remote sample from the heart were then derived as follows:

$$\overline{\sigma}_{sample} = \frac{\sigma_{sample}}{\sigma'_{Remote}}$$

$$\overline{\varepsilon}_{sample} = \frac{\varepsilon_{sample}}{\varepsilon'_{Remote}}$$

Also, per-slice normalized conductivity ($\overline{\sigma}_{slice}$) and permittivity ($\overline{\varepsilon}_{slice}$) were calculated for the Hemo+, Hemo−, Remote and Sham groups by weight-averaging $\overline{\sigma}_{sample}$ and $\overline{\varepsilon}_{sample}$ respectively from their constituent samples.

Local Iron Deposition Measurements

The extent of iron (Fe) deposition within each myocardial sample from the Hemo+, Hemo−, Remote and Sham groups was analyzed using Inductively Coupled Plasma-Mass Spectrometry (ICP-MS) (J. P. Carpenter et al., *Circulation* 123, 1519 Apr. 12, 2011). The samples were briefly rinsed with ultrapure double-distilled deionized (Milli-Q) water (resistivity of 18MΩ-cm at 25° C.), blotted, weighed and placed in individual autoclavable Teflon centrifuge tubes (Thermo-Fisher Scientific, Waltham, Mass.). The Teflon tubes were soaked in 3% nitric acid overnight and rinsed with Milli-Q water before use. 2 ml of 69% (w/v) trace-metal grade nitric acid (GFS Chemicals Inc., Columbus, Ohio) was added to the samples and vented. The samples were then microwave digested using a Milestone EthosEZ closed microwave digestion system (Milestone S.r.l., Bergamo, Italy) equipped with temperature and pressure sensors (maximum temperature of 260° C. and maximum pressure of 10 MPa). The digestion temperature was ramped up at 12° C./min and maintained at 120° C. for 10 minutes before allowing to cool down to room temperature. The digested samples were then filtered through 0.45 μm Teflon syringe-filters (Thermo-Fisher Scientific) and the filtrates were collected in individual 15 ml metal-free polypropylene tubes (VWR International Inc., Bridgeport, N.J.). The filtrates were diluted to 1:40 of original concentration with Milli-Q water and an internal standard mixture (CPI International, Santa Rosa, Calif.) containing Sc, Tb, Y, In and Bi was added. A set of standards with concentrations ranging from 0 ppb to 100 ppb was prepared using a mixed element solution (CPI International, Santa Rosa, Calif.). All samples and standards were prepared in duplicates in a 2% nitric acid matrix.

All samples were analyzed on a quadrupole based X Series 2 ICP-MS (Thermo-Fisher Scientific) equipped with Collision Cell Technology to reduce interference from doublets. Samples were introduced into the ICP-MS at a rate of 0.5 ml/min using an automated SC-FAST system (Elemental Scientific Inc, Omaha, Nebr.) comprising of an autosampler, diaphragm vacuum pump, PFA-ST nebulizer and a Peltier-cooled cyclonic spray chamber. Data was acquired using the dedicated PlasmaLab software. Fe content measured within each sample was averaged between the two duplicates and expressed as µg of Fe per g of sample ($Fe_{sample}$). Also, per-slice Fe content of Hemo+, Hemo−, Remote and Sham groups ($Fe_{slice}$) were measured by weight-averaging $Fe_{sample}$ of their constituent samples.

Statistical Analysis

All statistical analyses (both animals and patients) were performed using STATA 10.1 (StataCorp, College Station, Tex.). All data are expressed as Mean±SD. For animals, ex-vivo $T2*_{slice}$ (per-slice ex-vivo T2*), $Fe_{sample}$ (Fe content within myocardial sample), $\bar{\sigma}_{sample}$ and $\bar{\epsilon}_{sample}$ were compared among Hemo+, Hemo−, Remote and Sham groups using mixed-model linear regression. The null hypothesis was that there was no difference in each tested parameter among the four different groups. Since differences among the animals were of no interest, canines were entered as random effects. Samples from each heart (or myocardial slice) were nested in the analysis to account for repeated measurements from a single heart (or myocardial slice). The relationship between in-vivo $T2*_{heart}$ (from both acute and chronic phase MRI studies) and the corresponding ex-vivo $T2*_{heart}$ was analyzed using mixed-model linear regression. Similarly, the relationships of log(ex-vivo $T2*_{slice}$) with log($Fe_{slice}$), $\bar{\sigma}_{sample}$ and $\bar{\epsilon}_{sample}$ with log($Fe_{sample}$), $\bar{\sigma}_{slice}$ and $\bar{\epsilon}_{slice}$ with log(ex-vivo $T2*_{slice}$) were analyzed. The null hypothesis was that there was no linear relationship between the tested parameters.

Similarly, for patients, mixed-model linear regression was used to compare in-vivo $T2*_{section}$ among the Hemo+, Hemo− and Remote groups. The null hypothesis was that there was no difference in in-vivo $T2*_{section}$ among the three different groups. Patients were entered as random effects and repeated measurements from each heart (or imaging section) were accounted for by nesting the measurements for analyses. The relationship between mean in-vivo $T2*_{heart}$ from acute and chronic phase MRI studies was analyzed using mixed-model linear regression. The null hypothesis was that there was no linear relationship between mean in-vivo $T2*_{heart}$ from acute and chronic phase MRI studies. A two-tailed p-value <0.05 was considered to be statistically significant for all animal and patient data analyses.

Example 2 Free-Breathing, ECG-Triggered, Dark-Blood Prepared 3D T2* MRI

Breath-held, ECG-triggered, 2D T2* mapping at 1.5 T is the current standard for identifying iron overload in the heart. However, this approach has a number of limitations for our application: (i) Our early studies and the literature suggest that, in the setting of large infarcts, breath holding may trigger arrhythmias. In our experience, repetitive breath-held image acquisitions have led to fatal arrhythmias in canines with hemorrhage; and non-fatal arrhythmias demand undesirably long breath holding times; (ii) Partial volume effects in the through-plane direction can significantly reduce the conspicuity of the regions with an iron overload; (iii) Bright blood T2* maps are prone to significant image artifacts (ghosts and smears), particularly when TEs are long. At 1.5T, the sensitivity for visualizing smaller iron depositions can be limited and require the use of longer TEs in spite first-order flow compensation at every TE. Doubling the field strength is known to increase the image contrast for detecting iron particulates by a factor of 4, which in turn implies that significantly shorter TEs may be used to generate T2* maps. Flow compensation at shorter TEs and dark-blood imaging may be ideal for overcoming these artifacts. The current approach also has limited signal-to-noise (S/N) characteristics. 3D mGRE acquisitions, particularly when performed at 3.0T, can increase the S/N and permit the use of image acceleration strategies to reduce scan time without compromising S/N.

To overcome these limitations we propose a navigator-gated, double inversion recovery prepared 3D multi gradient echo (mGRE) sequence so that significantly artifact-reduced, free breathing, high-resolution, T2* maps can be generated. The timing diagram for this imaging sequence is shown in FIG. 1.

Example 3 Detecting Acute Myocardial Reperfusion Hemorrhage (aMRH) with MRI

T2 and T2* MRI have both been shown to be sensitive for detecting aMRH. However, there is (i) no consensus on which of the two methods yield the most desirable means for detecting aMRH, and (ii) no histology studies that confirm T2 or T2* MRI can and do identify myocardial hemorrhage (O'Regan D P, Ahmed R, Karunanithy N, et al. Reperfusion hemorrhage following acute myocardial infarction: assessment with T2* mapping and effect on measuring the area at risk. Radiology 2009; 250:916-922. Ganame J, Messalli G, Dymarkowski S, et al. Impact of myocardial haemorrhage on left ventricular function and remodelling in patients with reperfused acute myocardial infarction. Eur Heart J 2009; 30:1440-1449). The inventors determined the optimal quantitative MRI approach for detecting a MRH and to validate that iron composites are found within hemorrhagic infarctions on the basis tissue histology.

Ischemia reperfusion injury (3 hour occlusion of LAD followed by reperfusion) was inflicted in canines (n=9). Serial MRI studies (T2 and T2* mapping, and delayed enhancement (LGE)) were performed post-reperfusion on days 2, 5 and 7. Hemorrhagic infarctions (MH+) were determined by the presence of hypointense territories on T2* maps within the infarcted zones identified from LGE images. In the MH+ group, ROIs from the T2* maps around the hemorrhagic cores and remote territories were copied onto the T2 maps. In non-hemorrhagic infarctions (MH−), manually drawn ROIs on LGE images around the infarcted zones and remote territories were copied onto T2 and T2* maps. T2 and T2* values from the MH+, MH− and remote territories were measured and compared (p<0.05). Animals were sacrificed on day 7 and TTC staining and histological analysis (H&E and Prussian blue) was performed.

Figure 2:
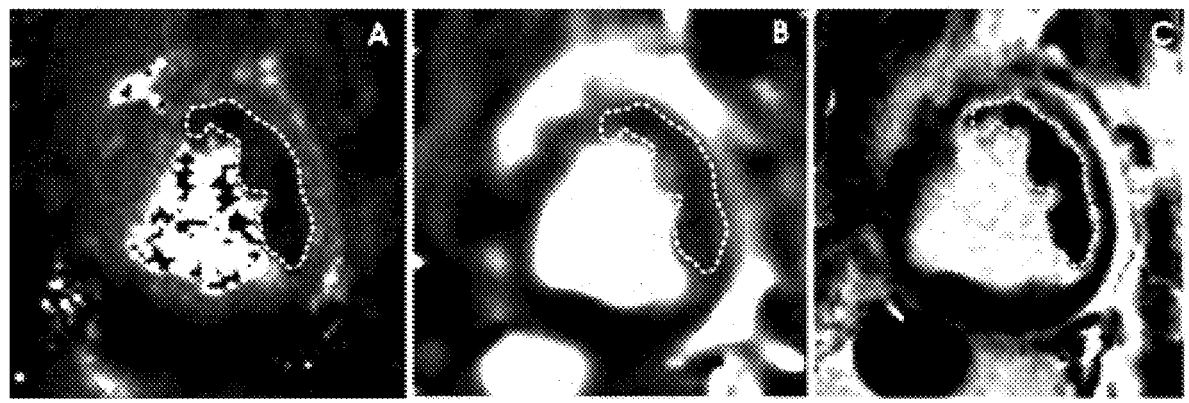
FIG. 2 depicts, in accordance with various embodiments of the present invention, cardiac MRI images showing high sensitivity for detection of hemorrhage. This figure depicts an example of short-axis T2* map (A), T2 map (B) and LGE image (C) from a dog on day 2 post-reperfusion. Manually traced ROI (dotted line boundary) around the hemorrhagic territory are shown. T2* changes, compared to T2 changes, were more pronounced in the presence of hemorrhage. Late-gadolinium enhancement (LGE) MRI showed the area of MI and the extent of microvascular injury (hyperintense core). Similar results were observed on days 5 and 7.
Figure 3A:
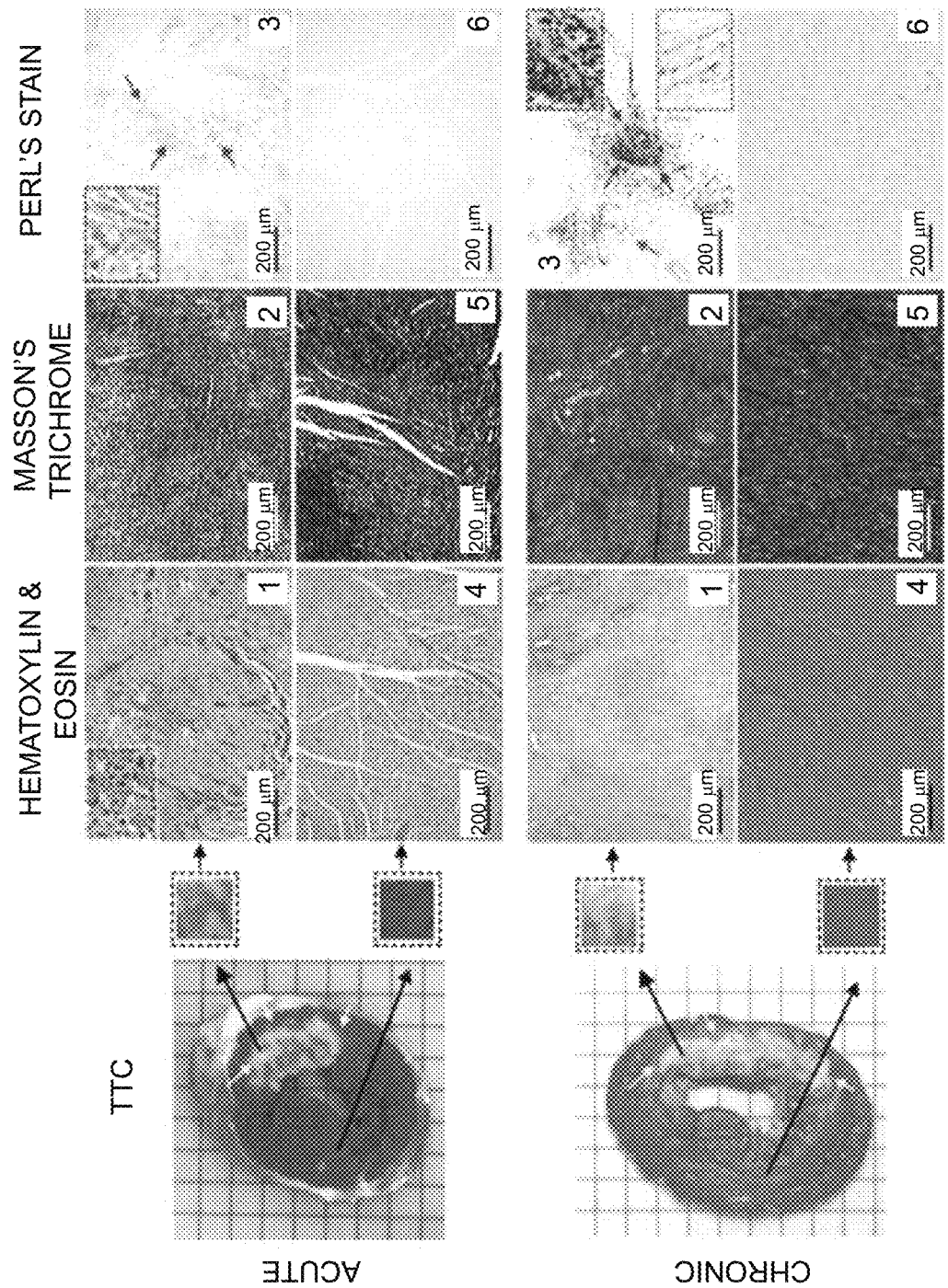
FIGS. 3A-3B depict, in accordance with various embodiments of the present invention, chronic iron deposition in hemorrhagic myocardial infarction.

MH was observed in 7 dogs, but not in the remaining 2 dogs. FIG. 2 shows a representative set of T2* and T2 maps and the corresponding LGE image in an animal with aMRH. Table 1 lists the respective values and the change in T2 and T2* between MH+, MH−, and remote territories. TTC stains and histology results are shown in FIG. 3A (a, a1-a6). TTC confirmed the infarction; and histology confirmed the presence of pooled red blood cells and iron within regions of reperfused infarcts.

TABLE 1

| | Region | | | | |
|---|---|---|---|---|---|
| | | | | % Change | |
| Technique | Remote | MH+ | MH− | MH+ | MH− |
| T2* (ms) | 41 ± 5 | 23 ± 5 | 43 ± 6 | −42 ± 14% | 8 ± 17% |
| T2 (ms) | 55 ± 6 | 62 ± 5 | 72 ± 4 | 13 ± 14% | 35 ± 11% |

Table 1: Mean T2* and T2 values of hemorrhagic (MH+), non-hemorrhagic (MH−) and remote territories averaged across all animals and study days are shown. Percentage T2* and T2 changes of MH+ and MH− are computed relative to remote myocardium. T2* of MH+ decreased significantly compared to MH− and remote myocardium. T2 of both MH+ and MH− was significantly higher relative to remote myocardium. Only T2* changes were statistically lower than remote regions (t-test, $p<0.05$).

T2* of MH+ territories were significantly lower than the T2* of MH− and remote territories. This was not the case in T2 maps. The reduced conspicuity of MH on T2 maps is likely due to its intrinsic sensitivity to myocardial edema. The insensitivity of T2* MRI to edema and strong sensitivity to hemorrhage makes T2* maps the most effective method for detecting a RMH. Histological evidence confirmed that the hypointense regions within infarcted myocardium in T2* MRI are hemorrhagic. These results support our hypothesis that T2* MRI is suited for noninvasive identification of myocardial hemorrhage in vivo.

Example 4 Iron Deposition Electrical Properties of Myocardial Infarcts

Previous studies have shown that introducing highly conductive particulates into an otherwise poor dielectric medium acts to enhance the bulk electrical permittivity of the medium. Since magnetite crystals have a relatively high electrical conductivity (approximately $2.5 \times 10^4$ S/m at the physiologic temperature), pathological elevations of it within localized regions of the heart muscle (with conductivity <1 S/m may act to increase the electrical permittivity of infarcted myocardial tissue.

Figure 6C:
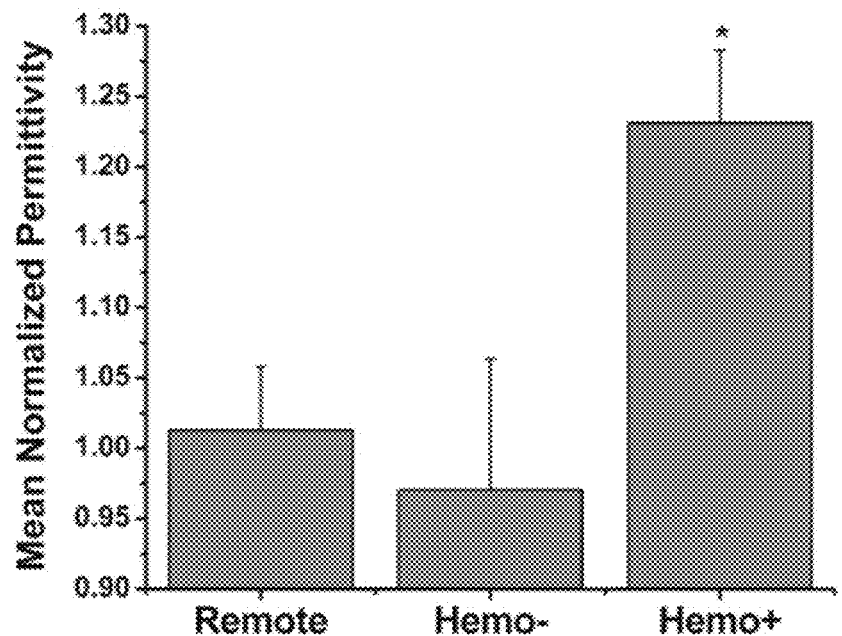
Figure 6D:
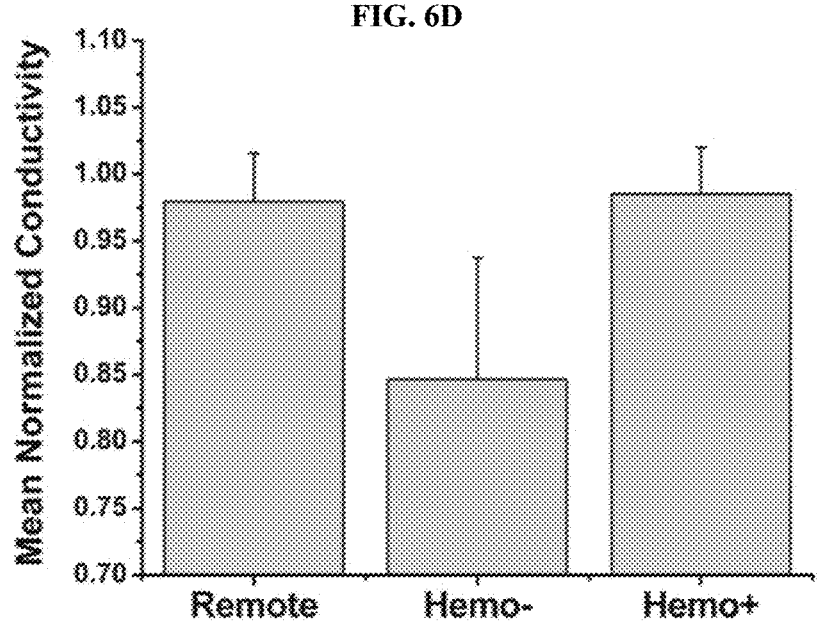
Figure 14:
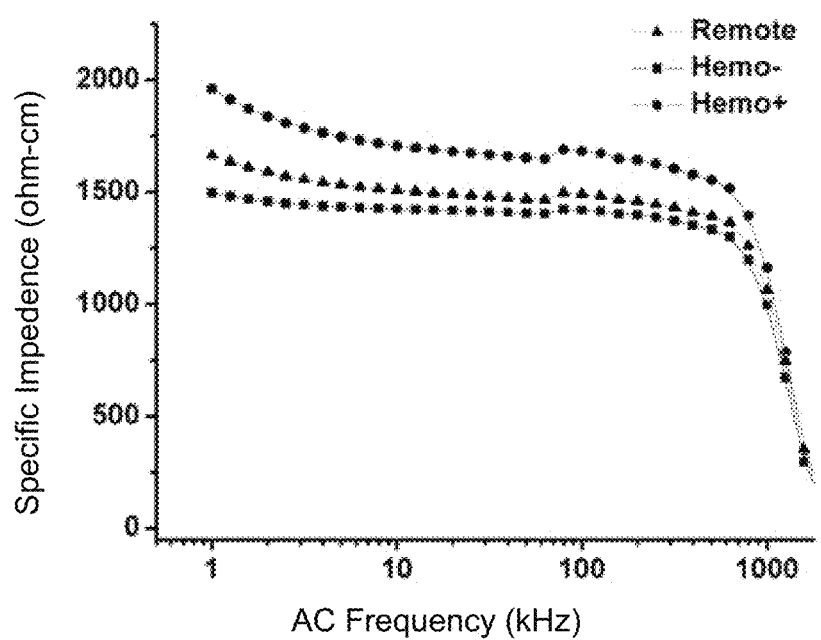
FIG. 14 depicts, in accordance with various embodiments of the present invention, representative specific impedance spectroscopy measurements from Remote, Hemo−, and Hemo+ myocardial samples. Note that for a given AC frequency, specific impedance of Hemo+ sample is higher than those of the Remote and Hemo− samples.

To investigate the influence of iron deposition on the electrical permittivity and conductivity of infarcted tissue, specific impedance spectra were obtained from ex-vivo tissue samples (Remote, Hemo−, and Hemo+) using a custom-built capacitor cell (FIG. 12) over an alternating-current frequency range of 100 Hz to 10 MHz (FIG. 14). From the impedance measures, estimates of normalized permittivity ($\bar{\varepsilon}$) and conductivity ($\bar{\sigma}$) of Hemo− and Hemo+ tissues (normalized to mean values of remote tissue for the whole-heart), were derived. To mitigate systematic errors in impedance measures from α-dispersion[36] and tissue preparation errors (resulting in unwanted tissue mixing), both of which can be prominent at low frequencies, the analysis was limited to 1 MHz. A mixed-effects multi-linear regression analysis (accounting for variations among animals and tissue slices) was performed to test for the existence of a linear relation between [Fe] (obtained from ICP-MS measurements above) and $\bar{\varepsilon}$ and $\bar{\sigma}$, respectively. Regression analysis showed a statistically significant relation between $\bar{\varepsilon}$ and [Fe]: $\bar{\varepsilon}=1.34$ [Fe]+0.93, with $p<0.001$; but not between $\bar{\sigma}$ and [Fe], (see FIGS. 6A and 6B). Mean $\bar{\varepsilon}$ for Hemo+ sections was significantly different from mean $\bar{\varepsilon}$ for Hemo− and Remote tissues ($p<0.001$), while $\bar{\varepsilon}$ of Hemo− and Remote sections were not statistically different from 1 (FIG. 6C). Similarly, comparisons of mean $\bar{\sigma}$ were not significantly different among the different tissue types (FIG. 6D). Averaged across all studies, we observed a mean increase in $\bar{\varepsilon}$ of approximately 25% in the infarcted territories with iron deposition, while no change was observed in remote or infarcted territories without iron. Since the observed changes in $\bar{\varepsilon}$ were not accompanied by changes in $\bar{\sigma}$, it appears that the effect of iron deposition is to transform the infarcted territory into an ideal capacitor.

A noninvasive, image-guided index that can be calibrated against electrical tissue permittivity may be valuable for in-vivo monitoring and characterization of chronically infarcted myocardium. Given that the iron within infarcted tissue influences the myocardial T2* and $\bar{\varepsilon}$ (but not $\bar{\sigma}$) of that tissue, we expected to find a similar relation between T2* and $\bar{\varepsilon}$ (but not $\bar{\sigma}$). A mixed-effects multi-linear regression analysis, performed between log(T2*) and $\bar{\varepsilon}$ and $\bar{\sigma}$, respectively, showed a statistically significant linear relation between $\bar{\varepsilon}$ and log(T2*): $\bar{\varepsilon}=-0.66$ log(T2*)+3.11, with $p<0.02$; but not between $\bar{\sigma}$ and [Fe], (see FIGS. 6E and 6F). While this analysis showed a strong relation between ex-vivo T2* and $\bar{\varepsilon}$, given the correlation between ex-vivo and in-vivo T2* (FIG. 4B), it is likely that such a relation may also be extended between in-vivo T2* and $\bar{\varepsilon}$. Our findings here showed that it may be possible to acquire a non-invasive marker for changes in electrical permittivity (or capacitance) of infarcted territories with CMR on the basis of T2* relaxometry.

Example 5 Chronic Iron Deposition Takes Place Following Hemorrhagic Myocardial Infarction A total of 17 canines (3 controls/Shams and 14 subjected to ischemia-reperfusion (I/R) injury (3 hours of ischemia in the territory supplied by the left anterior descending coronary artery (LAD) followed by reperfusion)) were studied. Of the 14 animals with I/R injury, 3 animals were sacrificed on day 3 for gross and histopathologic analysis. The remaining 11 animals were allowed to recover into a chronic phase and sacrificed on day 56, when tissue analysis was performed.

Myocardial tissue analysis from animals sacrificed on day 3 showed that I/R injury led to large myocardial infarctions evidenced by positive staining in Triphenyl Tetrazolium Chloride (TTC) with internal bleeding at the core of the myocardial infarction. Hematoxylin & Eosin (H&E) stains confirmed the tissue damage and morphological alterations in regions positive for infarction in TTC stainings. H&E stains also showed extravasation of RBCs into the interstitial space of the infarcted regions. Perl's stains confirmed a local accumulation of iron in the infarct areas. Gross observation of TTC-stained myocardial tissue from animals with chronic infarcts showed the presence of large infarcted regions with yellowish-brown discoloration at the core of the infarct. H&E stains from the same tissue confirmed the presence of extensive tissue damage and Masson's Trichrome stain showed collagenous tissue in the infarct zone. Interestingly, Perl's stain of corresponding myocardial territories showed a persistent and heterogeneous deposition of iron within the infarction. Iron was also found to be inter-spread among viable cardiomyocytes in incompletely infarcted territories (FIG. 3A (b6), lower inset). For a given stain, tissue from remote (unaffected) territories were similar between acute and chronic stages of the infarction, but were markedly different from infarcted territories (see FIG. 3A).

Figure 3B:
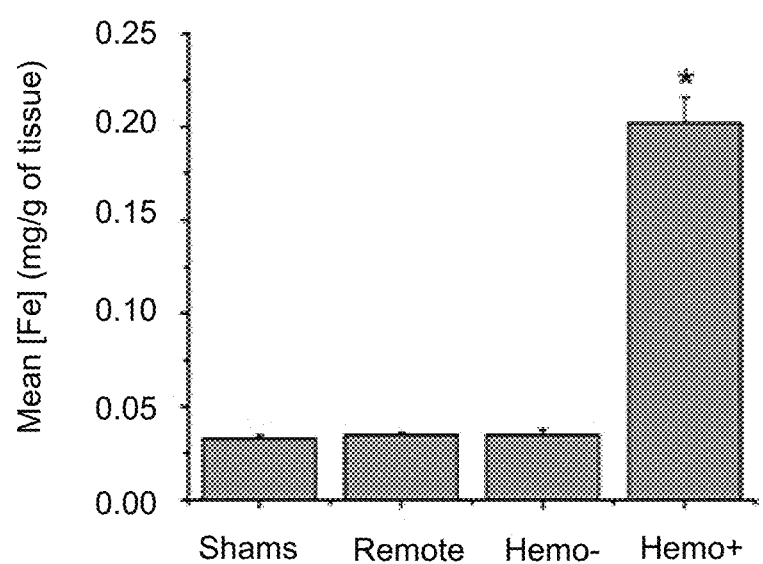

To examine the extent of iron deposition within chronic infarcts, Inductively Coupled Plasma Mass Spectrometry (ICP-MS) was performed on the myocardial tissue in the chronic stage of shams and animals subjected to I/R injury. Tissue iron content ([Fe], in mg of iron/g of muscle) from Shams, remote (Remote), infarction without hemorrhage (Hemo−), and those with hemorrhagic infarctions (Hemo+) were measured. The mean value of iron content in Hemo+ was significantly elevated (p<0.0001) compared to all the control tissues (Shams, Remote, and Hemo−), (see FIG. 3B). Thus, ICP-MS data shows that hemorrhage from I/R injury leads to nearly an order of magnitude greater iron content in infarcted tissue compared to the different control groups (Shams, Remote, and Hemo−). Our findings are consistent with previous observations of the deposition of iron in tissue in the form of hemosiderin (magnetite-crystalline $Fe_3O_4$ particles) following the biodegradation of RBCs in other pathologies.

Example 6 MRI can Non-Invasively Detect Iron Deposition within Myocardial Infarcts Biogenic magnetite is known to have the highest conductivity of any cellular material. It is also ferromagnetic in the range of physiological temperatures and acts as a strong dipole in a magnetic field. Magnetic field variations surrounding these "biological bar magnets" can impart significant influence on the phase coherence of protons ($^1H$) and enhance T2* relaxation, which provides opportunities for in-vivo proton Magnetic Resonance Imaging (MRI) (63). To determine if hemosiderin deposition within chronic infarctions can be identified non-invasively, each animal (from above) underwent Cardiovascular Magnetic Resonance (CMR) imaging during the acute (day 3) and chronic (day 56) phase following I/R injury in a whole-body clinical 1.5 T MRI System. Sham-operated animals were imaged at the same time points. Following the in-vivo CMR scan on day 56, animals were sacrificed and the hearts were harvested and imaged. Each scan protocol included the acquisition of myocardial T2* maps for detection of hemorrhage in the acute phase and iron deposition within the infarcted territories in the chronic phase. Late gadolinium enhancement (LE) CMR scans were also performed for detection/confirmation of infarction.

Figure 4A:
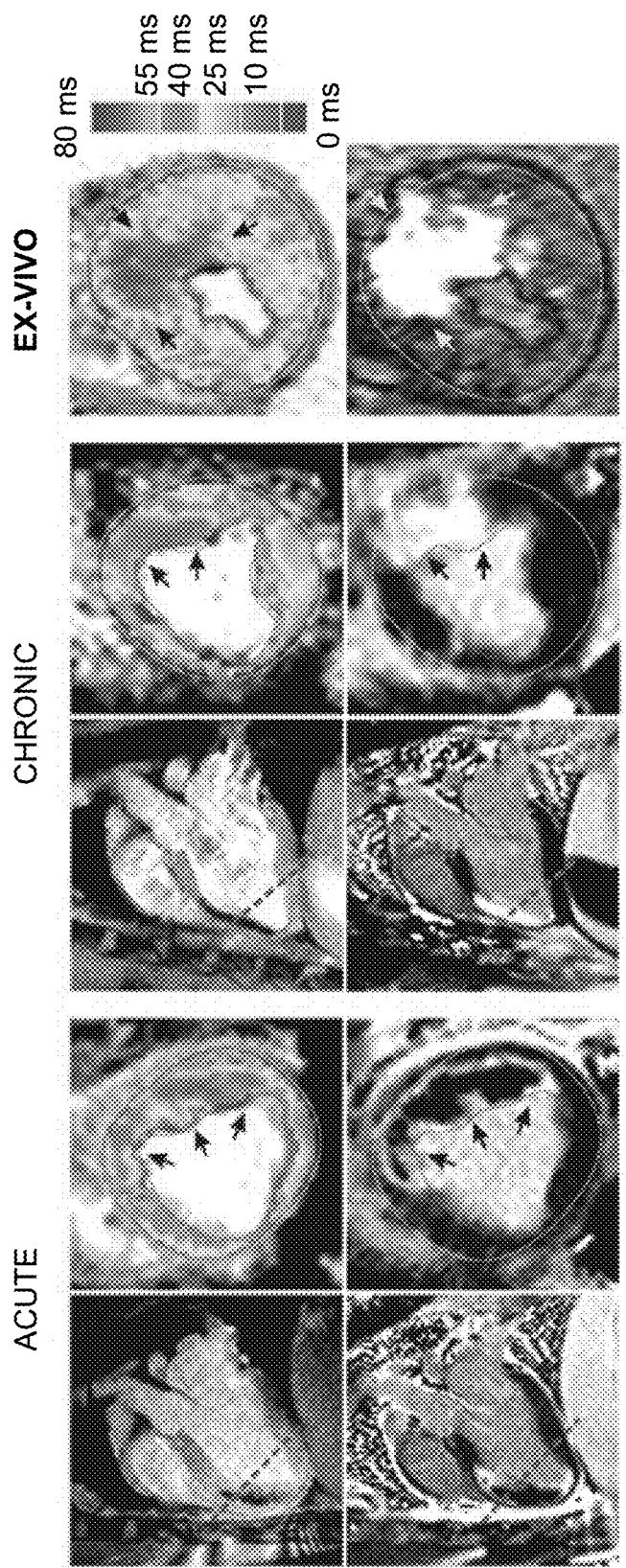
FIGS. 4A-4D depict, in accordance with various embodiments of the present invention, a non-invasive CMR image-guided characterization of regional iron deposition following reperfused hemorrhagic myocardial infarction.
Figure 4B:
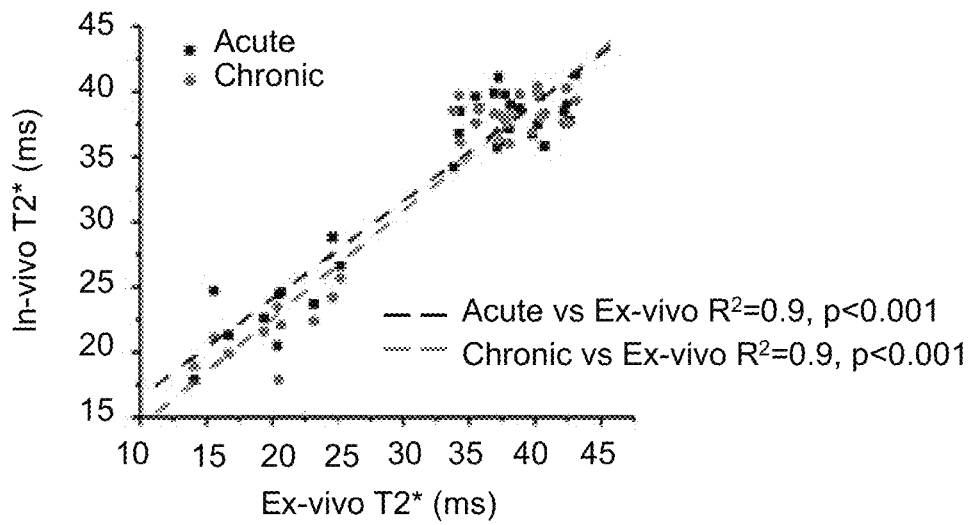
Figure 4C:
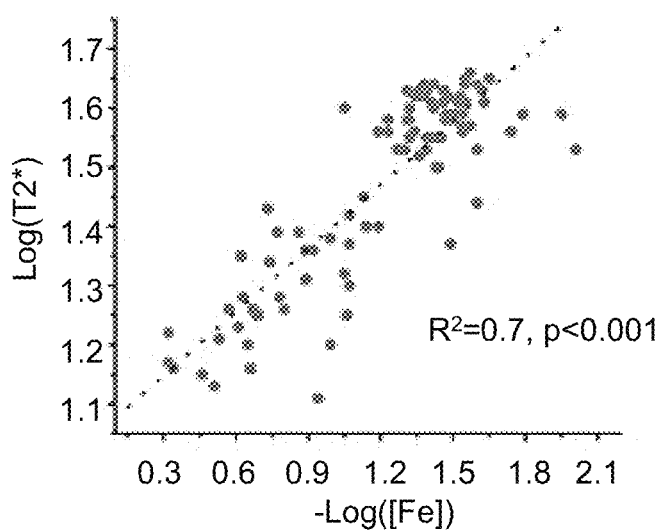
Figure 4D:
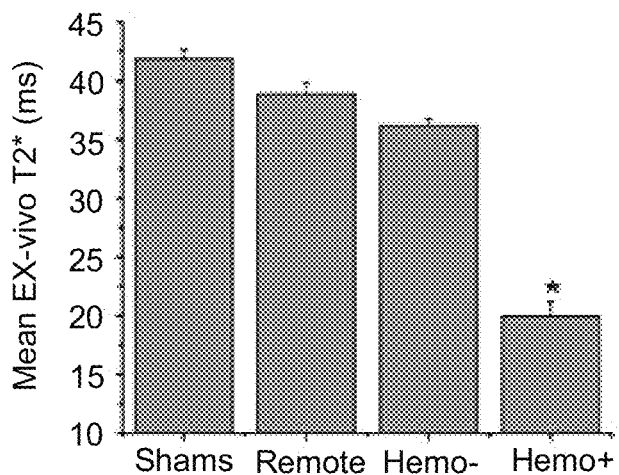

Representative images obtained from the CMR studies are shown in FIG. 4A. Significant T2* decreases were observable in the LAD territories (where hemorrhagic infarctions were expected) in the acute and chronic phases. The T2* of Remote and LAD territories in the acute and chronic tissue were nearly constant. From the T2* maps, the mean myocardial T2* values of the sham, Remote, Hemo− and Hemo+ tissues were measured. Pooled mean T2* values from these tissues on days 3 and 56 (in vivo), regressed individually against ex-vivo T2* estimates, showed very strong correlations ($R^2$=0.9 for day 3 vs. ex vivo and 0.9 for day 56 vs. ex vivo; p<0.001 for both cases; see FIG. 4B). Regressions between T2* estimates and tissue iron content (determined from ICP-MS) also showed a strong correlation (log (T2*) vs −log ([Fe]), $R^2$=0.7; p<0.001; see FIG. 4C). Comparison of mean ex-vivo T2* among the different groups showed that only Hemo+ was significantly different from the other groups (p<0.001; see FIG. 4D). We also observed that the mean T2* values of Remote, Hemo− and Hemo+ tissues in the acute and chronic tissue to be nearly constant and that the T2* values between Remote and Hemo− tissue groups were not different and were independent on when the T2* measures (acute or chronic) were made. On average, we observed a near 40% decrease in T2* in regions of hemorrhagic infarctions compared to the control groups at 1.5T. Most notably, the CMR studies showed that iron deposition within chronic hemorrhagic infarctions could be reliably detected and quantified with a whole-body clinical MR scanner.

Example 7 Evidence for Iron Deposition in Humans with Reperfused Myocardial Infarction The specific long-term consequences of hemorrhagic transformation of myocardial infarction in humans are unknown. We investigated whether patients suspected of having hemorrhagic infarctions showed iron loading within infarcted territories on the basis of CMR. Fifteen patients were enrolled and scanned 3 days and 6 months following successful angioplasty for a first ST-elevation myocardial infarction. Each scan protocol included the acquisition of myocardial T2* maps for detection of hemorrhage in the acute phase and regional iron deposition within the infarcted territories in the chronic phase. Late gadolinium enhancement CMR scans were also prescribed for detection/confirmation of infarction. In the acute phase (day 3), eleven patients were identified positive for having had hemorrhage (T2* decrease within the infarcted myocardium) and four patients were not positive for hemorrhage.

Figure 7A:
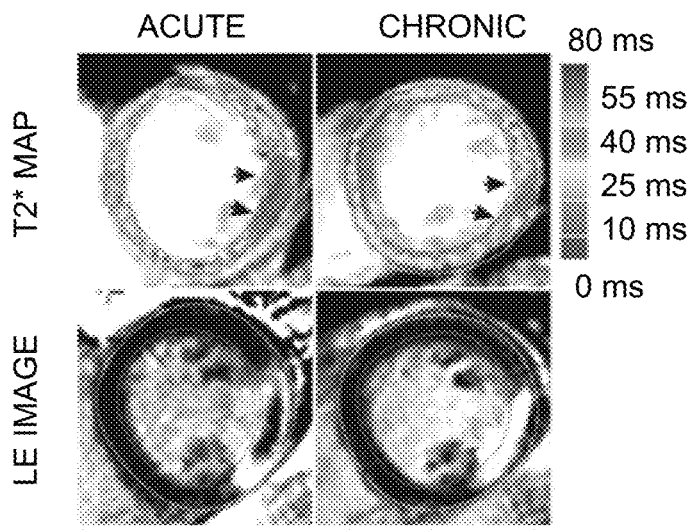
FIGS. 7A-7C depict, in accordance with various embodiments of the present invention, non-invasive imaging-guided evidence for regional iron deposition in humans following hemorrhagic myocardial infarctions.
Figure 7B:
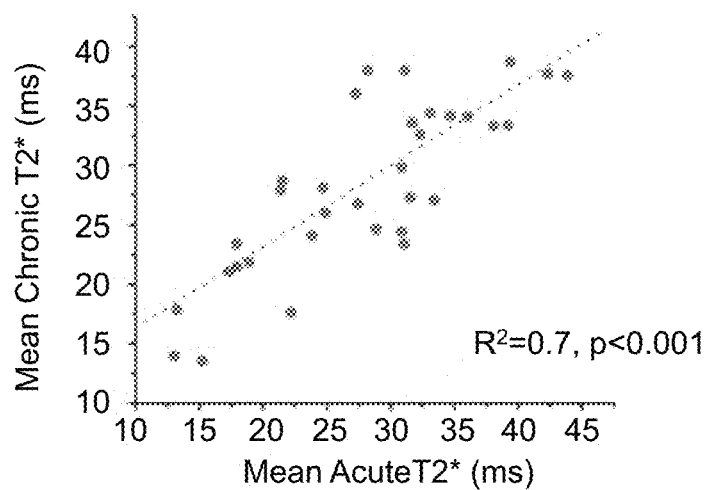
Figure 7C:
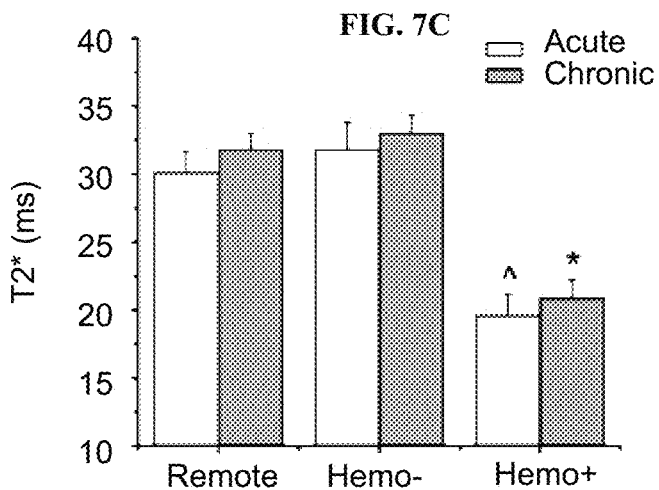

A representative set of CMR images acquired at 3 days and 6 months post angioplasty in a patient suspected of having had hemorrhagic infarction is shown in FIG. 7A. Significant T2* decreases were observed in the infarcted territories in eleven patients and such losses continued to be evident on the 6-month follow up images. In four patients, T2* losses were not evident on day 3 and were also not detected on the 6-month follow up scans. From the myocardial T2* maps, the mean myocardial T2* values of the Remote, Hemo− and Hemo+ territories were estimated. Pooled mean T2* values from these tissues on day 3 and 6 month, regressed against one-another showed a strong correlation ($R^2$=0.70, p<0.001), (see FIG. 7B). Comparison of mean T2* among the different groups obtained from the acute and chronic scans showed that only Hemo+ was significantly different from the other groups (p<0.001), (see FIG. 7C).

Consistent with animal studies, we also observed the mean T2* values of Remote, Hemo− and Hemo+ tissues in the acute and chronic tissue to be nearly constant and were similar to T2* values in animals. Moreover, T2* values between Remote and Hemo− tissue groups were not different and were independent on when the T2* measures were made post angioplasty. Similar to the animals studies, on average, we observed an approximate decrease of 40% decrease in T2* in regions of Hemo+ compared to the control sections, Remote and Hemo−. Our findings here indicate that one of the long-term effects of hemorrhage in the chronic stage of infarction is focal loading of iron deposits within the infarcted territories and that such deposits can be detected non-invasively with CMR.

Figure 9:
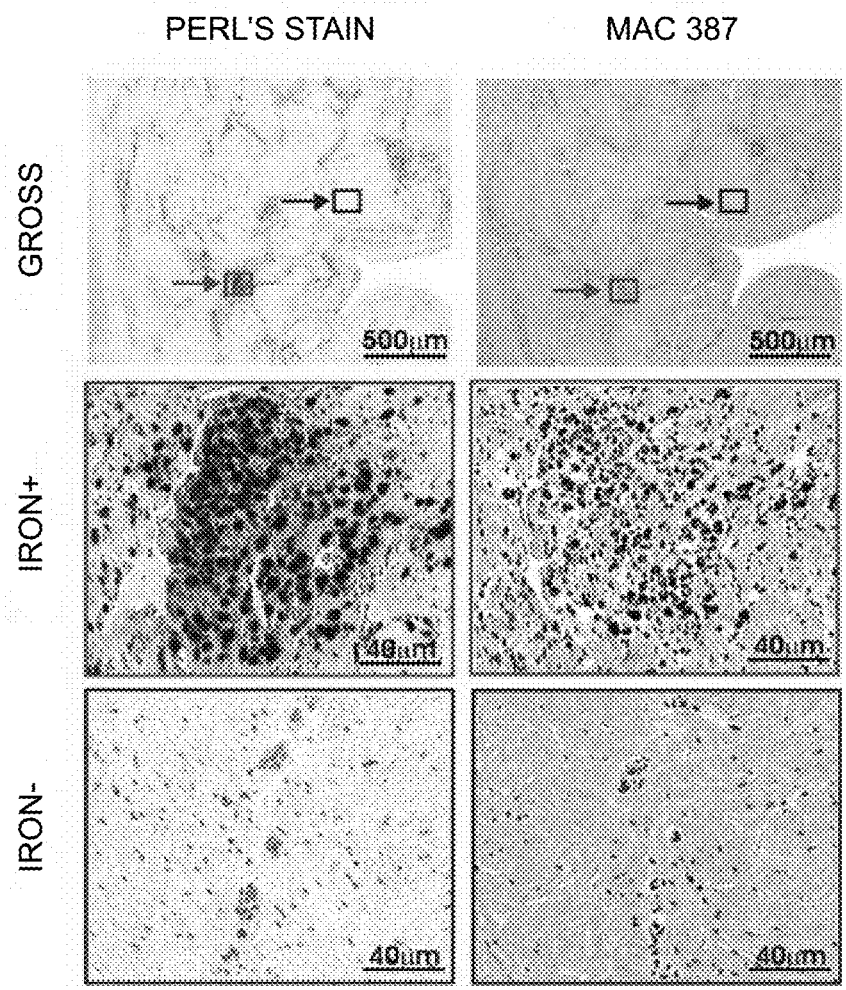
FIG. 9 depicts, in accordance with various embodiments of the present invention, the co-localization of newly recruited macrophages with chronic iron deposits. Contiguous histological sections of a chronic hemorrhagic infarction stained with Perl's and MAC 387 stains are shown. Macrophages are highly co-localized with the iron deposits throughout the infarct (GROSS). Magnified regions with (IRON+; red box) and without (IRON−; blue box) iron depositions show that macrophages preferentially co-localize at the site iron depositions.

Example 8 Evidence for Prolonged Inflammatory Reaction at Sites with Chronic Iron Deposition from Hemorrhagic Myocardial Infarction Tissue sections from animals in Example 6 with and without hemorrhagic infarctions were stained with MAC 387 (for macrophages) stains respectively using standard techniques and imaged at 100× and 400× magnifications. MAC 387 staining of chronic infarctions showed that macrophages were highly co-localized with the chronic iron deposits identified on Perl's stain (FIG. 9). Minimal/no macrophages were observed in the infarcted myocardial territories that were devoid of iron deposits. The long-term deposition of iron, combined with macrophage infiltration at the site of iron, suggests that hemorrhagic infarctions may be subjected to extended periods of inflammation. This may be one of the potential mechanisms associated with adverse cardiac remodeling due to hemorrhagic infarctions.

Example 9 Early Evidence of VT in Dogs with Chronic Hemorrhagic MIs

Figure 8:
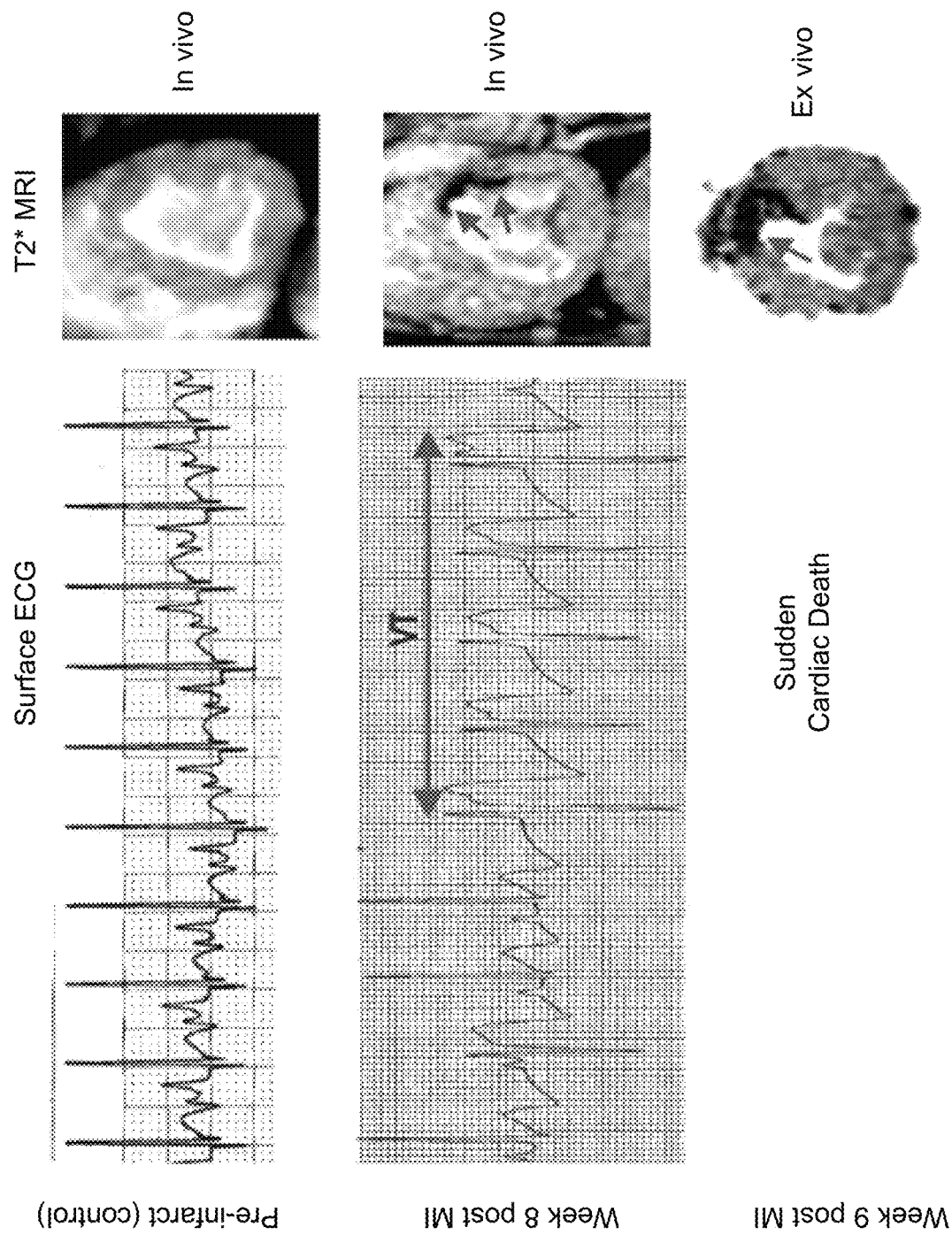
FIG. 8 depicts, in accordance with various embodiments of the present invention, ECG recordings from a dog with pre- and post-hemorrhagic MI. This figure depicts representative ECG tracings along with T2* MRI from a dog (pre- and post-MI with chronic iron overload) that was succumb to sudden cardiac death (SCD) on week 9 post MI. Ex-vivo T2* MRI, immediately after death, clearly shows the presence of chronic focal iron overload. Note the presence of VT on week 8 (the week preceding SCD). Focal, chronic iron overload in T2* MRI is indicated by arrows (dark cores).

From our studies in Example 5, three animals died from sudden cardiac death before week 10. ECG traces were normal in healthy dogs but pre-mature ventricular complexes (PVCs) were observed in all animals in weeks 8-10 (FIG. 8). Early evidence shows that iron deposition leads to changes in electrical permittivity (Example 4) are significantly increased in regions of chronic MI with iron deposition compared to control tissues. These findings, combined with the evidence of sustained PVCs and VTs, in animals with chronic I/R injury and iron deposits lend further support to the inventor's hypothesis.

Example 10 Evidence for Iron Deposition Following Non-Reperfused Myocardial Infarction A total of 16 canines subjected to non-reperfused MI (by permanently ligating left anterior descending coronary artery) were studied. T2* CMR images were acquired on day 7 and 3 months post MI. Images clearly showed the persistence of T2* loss within late enhancement territories on day 7 and week 8. Representative CMR images (on day 7 and month 3) and TTC stained slice acquired from one of the 16 animals is shown in FIGS. 5A-5E.

Example 11 Persistent Microvascular Obstruction Leads to Chronic Iron Deposition and Proinflammatory Burden Re-establishment of blood flow (reperfusion) through coronary arteries has reduced immediate death from acute myocardial infarctions (MI). However, the long-term complications in the chronic phase of MI, especially chronic heart failure (CHF) culminating in major adverse cardiovascular events (MACE), have become epidemic. Currently, ~2 million MI patients in the US are living with CHF; their 5-year survival rate is 50%.

An important and long-established predictor of CHF is the acute MI size, which is fundamentally tied to time to reperfusion. In the past two decades, advances in cardiac MRI (CMR) have established that persistent (or late) microvascular obstruction (PMO) is another independent predictor of CHF. PMO is an acute feature of MI where microvascular blood flow to the MI territory is lost despite reperfusion in epicardial arteries. PMOs are present in ~50% of acute MIs and resolve in <2 weeks. Notably, a multinational consortium recently reported that the presence of PMO carries a 4-fold greater risk for MACE (hospitalization/death) in the chronic period than acute MI size. Hence, therapeutic targeting of PMOs holds great promise for MI patients. Yet, current post MI medications are not specific to patients with PMO; and have not shown any incremental benefit to the patients with PMO over other MI types. Moreover, although much effort has been spent on preventing PMO from occurring, it has not yet been possible to consistently achieve this. These observations have led to recent emphatic calls for improved understandings of how PMOs drive adverse remodeling in the chronic phase of MI so that effective therapeutics may be developed.

Importantly, infarcted hearts with PMOs are known to adversely remodel in the chronic phase of MI, well after the PMOs have resolved—suggesting the existence of long-lived effects of PMO. In this regards, a frequent accompanying feature of PMO is reperfusion hemorrhage—extravasation of blood into the interstitium. Serial CMR definition has been instrumental in showing that hemorrhagic MIs, which are always accompanied by PMO, are known to remodel adversely. We developed clinically relevant animal models and rapidly translatable CMR methods to noninvasively study the pathophysiology of ischemic heart disease. Specifically, we investigated the long-term fate of hemorrhage and its influence on the heart. This led us to discover that PMOs with hemorrhage lead to iron deposits and persistent inflammation at 8 weeks post MI; and that this iron deposit is an independent marker of adverse remodeling in the chronic phase of MI in animals and patients (see e.g., Kali A, Kumar A, Cokic I, Tang R L, Tsaftaris S A, Friedrich M G, Dharmakumar R. Chronic manifestation of postreperfusion intramyocardial hemorrhage as regional iron deposition: A cardiovascular magnetic resonance study with ex vivo validation. Circulation. Cardiovascular imaging. 2013; 6:218-228).

Our data suggested that every PMO, including but not limited to hemorrhagic MIs, resolves into nanocrystals of ferric iron in chronic MI. Similar to gout, a disease in which urate crystals form and cause production of inflammatory cytokines (especially IL-1β), we found that the amount of iron crystals within chronic MI is related to the amount of inflammatory cytokines (including IL-1β). Moreover, by 6 months after MI, significant adverse remodeling (infarct thinning and fatty infiltration) were evident and was correlated with the extent of iron within MI. Importantly, decreasing urate crystals and blocking IL-1β have both been proven effective in treating gout. Without wishing to be bound by any particular theory, we believe that (a) PMO-driven iron deposition induces a pro-inflammatory macrophage phenotype, leading to accentuation and prolongation of the inflammatory response and cause adverse remodeling; and (b) therapies against this iron-mediated toxicity, such as deferiprone, a clinically approved intracellular chelator of ferric iron, may be a direct avenue for treating post MI patients.

A CMR method is developed for monitoring the extent of iron and fat within infarcted hearts over a 6-month period post MI in a clinically relevant animal model. Typically fat is not present at 8 weeks, but by 6 months post MI, fat can be found within some chronic MI. Quantification of iron is error prone when fat is present. To simultaneously and accurately follow iron and fat over a longer period of chronic MI when adverse remodeling is most evident, a confounder-corrected chemical shift-encoded T2* mapping can be used.

Figure 15:
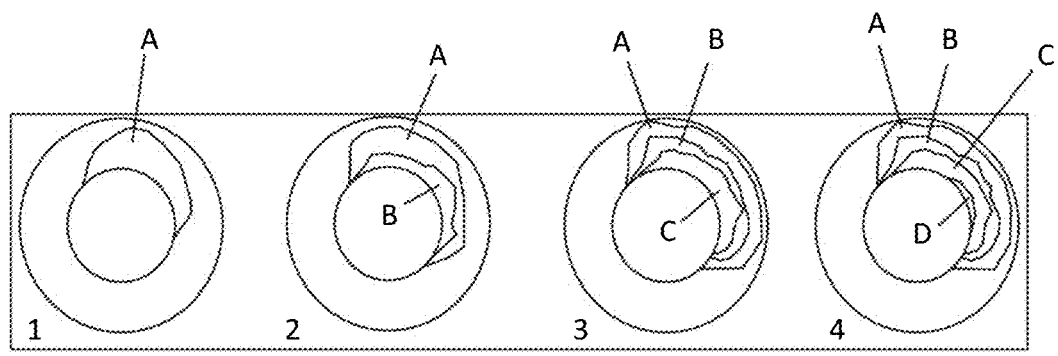
FIG. 15 depicts, in accordance with various embodiments of the present invention, schematic of types of reperfused acute MI. Myocyte death proceeds from the subendocardium as a "wave" of injury with increasing ischemic time. Key features of different MIs are: Type 1: Early, reperfusion with myocyte injury (MYI) only; Type 2: MYI+ microvascular injury (MVI); Type 3: MYI+ severe MVI; Type 4: MYI+ severe MVI with hemorrhage. Zones A: MYI only; B: MYI+ MVI; C: MYI+ severe MVI; and D: MYI+ severe MVI with hemorrhage. In zone B, there is slow flow within MVI; in zone C, there is no reflow; in Zone D, there is no reflow and blood is extravasated into the interstitium. Heart is shown in short-axis orientation.

Chronic heart failure epidemic and persistent microvascular obstruction are intimately related. I) Prevalence of chronic heart failure in post MI patients: Acute myocardial infarction (MI), from sudden obstruction of coronary arteries, affects ~1 million people in the US each year. Re-establishment of blood flow (reperfusion) through the epicardial arteries has been a major advancement as it has markedly reduced immediate death from acute MI. However, adverse LV remodeling during the post-MI period can culminate in CHF, which increases the rate of mortality. Evidence from the Framingham Study indicates that the incidence of post MI CHF has increased in the recent decades. In the US, it is estimated that +2.1 million patients are currently living with post MI CHF, and more than 250,000 new cases are reported every year. The 5-year survival rate of patients diagnosed with CHF is ~50%. The terminal recourse to these patients is heart transplantation (limited by availability of donor hearts, eligibility and cost) or stem cell therapy, which is still under development. II) Not all acute MIs are the same: A schematic of various types of acute MI built on the "wave front hypothesis" is shown in FIG. 15. Importantly, 50% of acute MIs are Types 3 and 4, where the MI territory has persistent microvascular obstruction (PMO), visualized as "no-reflow" zones (zones C and D in FIG. 15), despite re-establishment of blood flow in the culprit epicardial coronary artery. III) Acute MIs with PMO are more predictive of adverse events in the long term than MI Size: A key feature of MI is its size; and it has been established as an independent prognostic factor of MACE (death, hospitalization for CHF and adverse LV remodeling. With advances in imaging, particularly CMR, PMO (Types 3 and 4, refer to FIG. 15) has also emerged as a key prognostic factor of MACE. ENREF 21 Recent multinational studies (>1000 patients) have gone one step further—they showed that after multivariate adjustment, PMO has a 4-fold greater hazard ratio for MACE than MI size.

Current/Previously Explored Post MI Therapeutic Strategies have Limitations in Decreasing PMO.

Currently available post MI medications are not specific to patients with PMO; and have not been specifically beneficial to patients with PMO over other MI types.

Mechanistic Model for how PMO Promotes Adverse LV Remodeling in the Chronic Phase.

Figure 17:
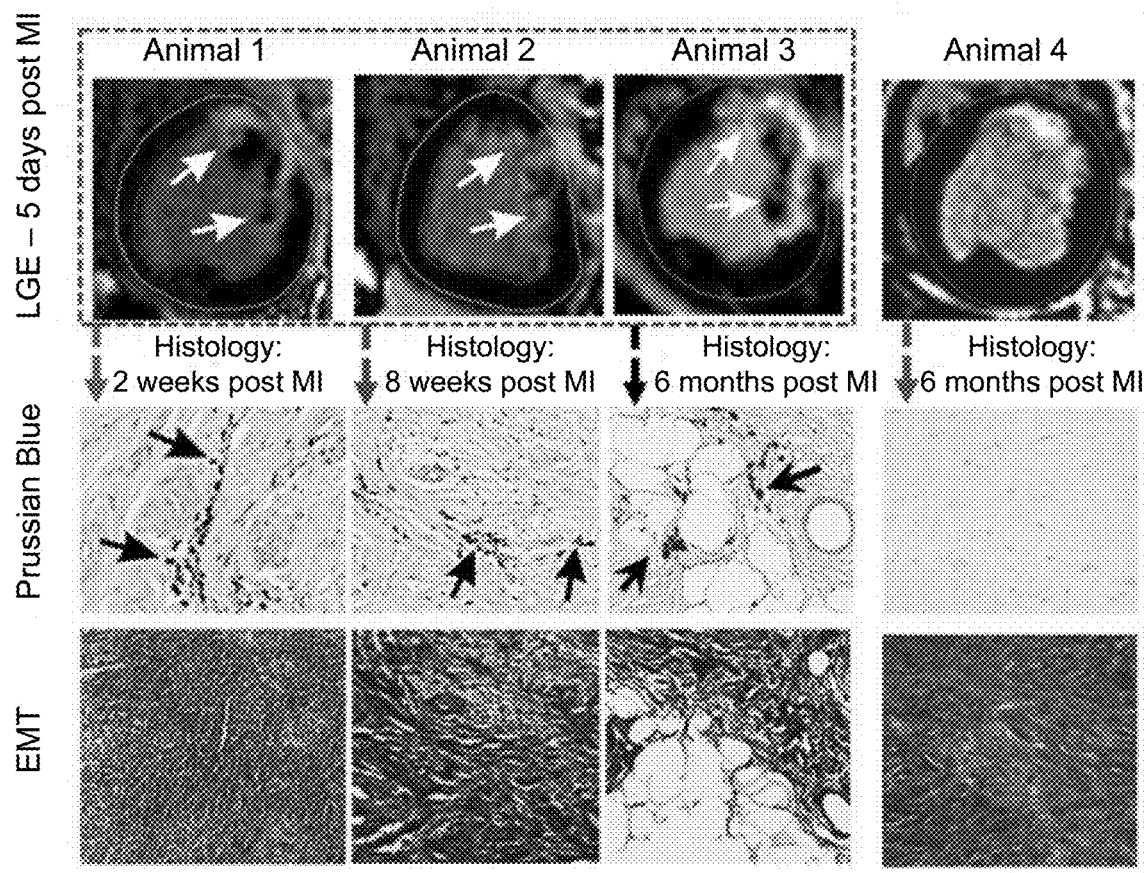
FIG. 17 depicts, in accordance with various embodiments of the present invention, acute MIs with PMO resolving into iron and infiltrated by fat in chronic phase of MI. LGE CMR acquired 5 days post MI shows evidence of PMO (arrows) in Animals 1-3. Histological evidence from animals sacrificed at 2 weeks, 8 weeks and 6 months show iron deposition (Prussian blue, blue dots), fatty infiltration (Prussian blue and Masson's Trichrome (EMT)) sections as white globules by 6 months. Conversely, Animal 4 did not have PMO on LGE CMR 5 days post MI or histological evidence of iron or fat within MI territory at 6 months post MI.
Figure 18:
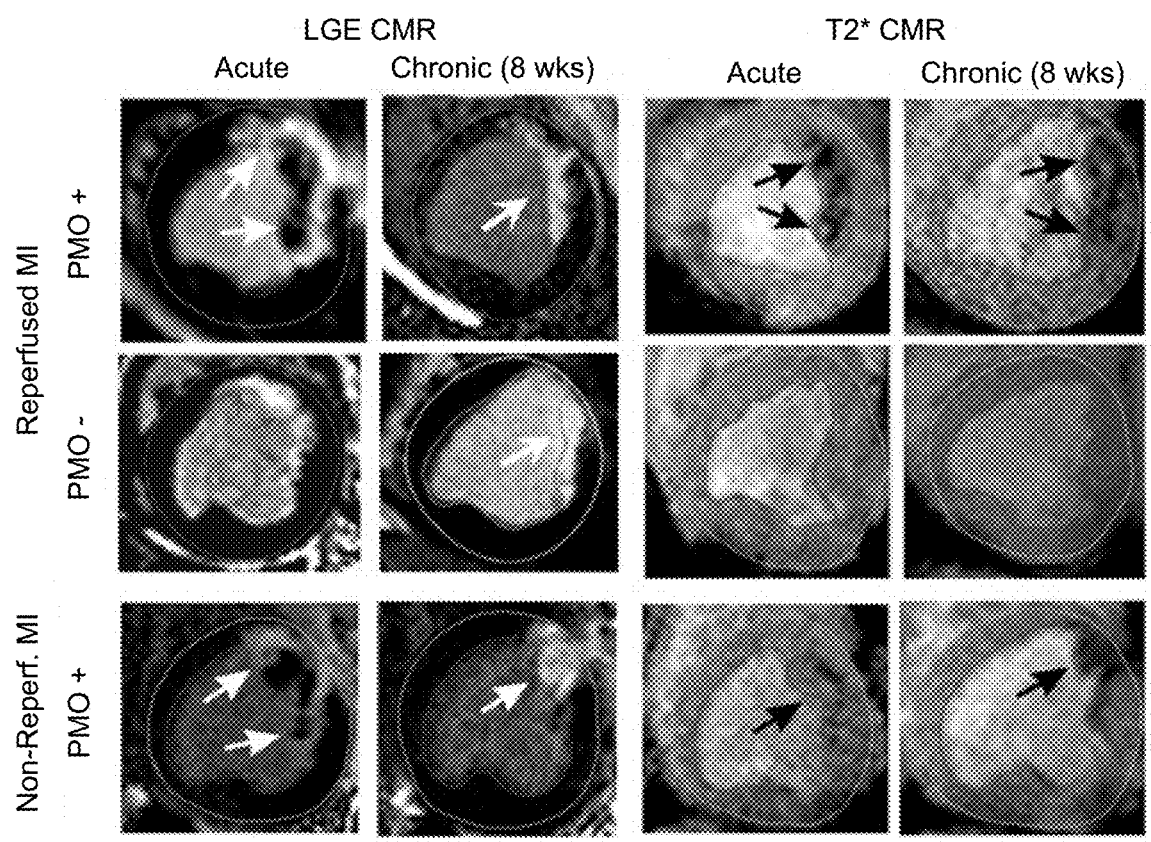
FIG. 18 depicts, in accordance with various embodiments of the present invention, persistent microvascular obstruction (PMO) with/without hemorrhage leads to iron deposits in chronic phase of MI.
Figure 19A:
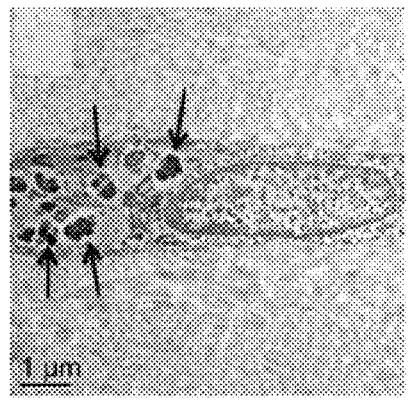
FIGS. 19A-19F depict, in accordance with various embodiments of the present invention, TEM, atomic-resolution imaging and X-ray EDS showing the physicochemical features of chronic iron deposits at 8 weeks post MI.
Figure 19B:
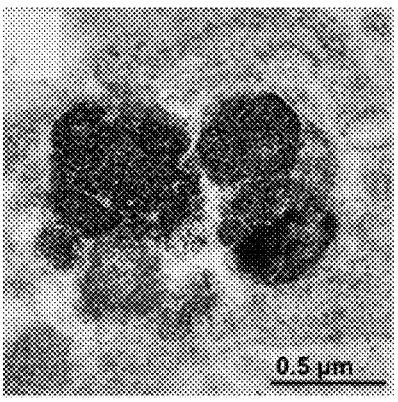
Figure 19C:
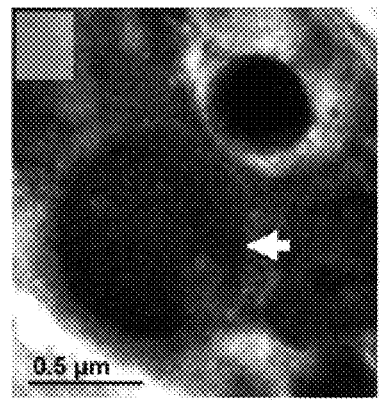
Figure 19D:
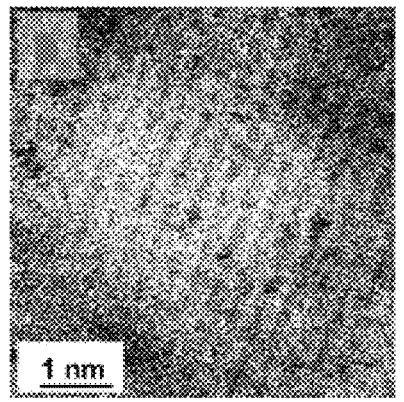
Figure 19E:
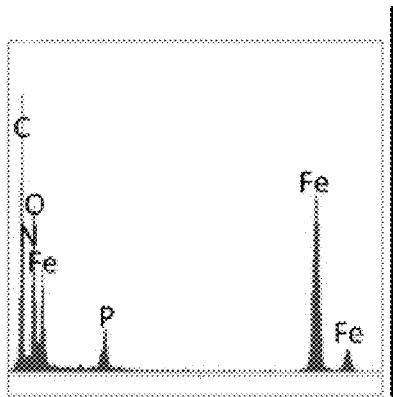
Figure 19F:
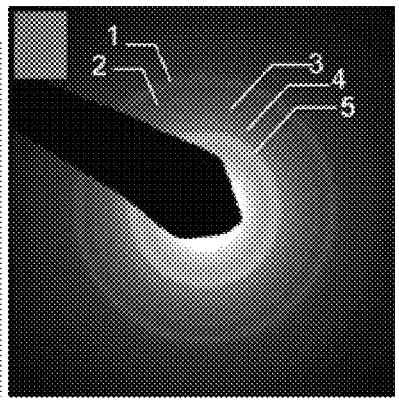
Figure 20:
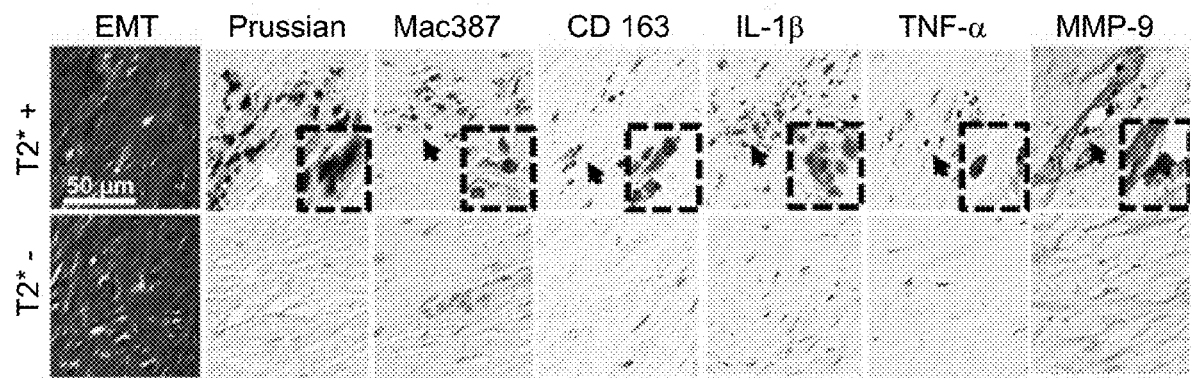
FIG. 20 depicts, in accordance with various embodiments of the present invention, evidence of co-localization of macrophages, cytokines and MMP in iron-rich MI. Contiguous sections stained with EMT, PB, and antibodies for Mac387, CD163, IL-1β, TNF-α, and MMP-9 are shown (insets are enlarged regions of interest) from $T_2^*+$ and $T_2^*-$ tissue.
Figure 21:
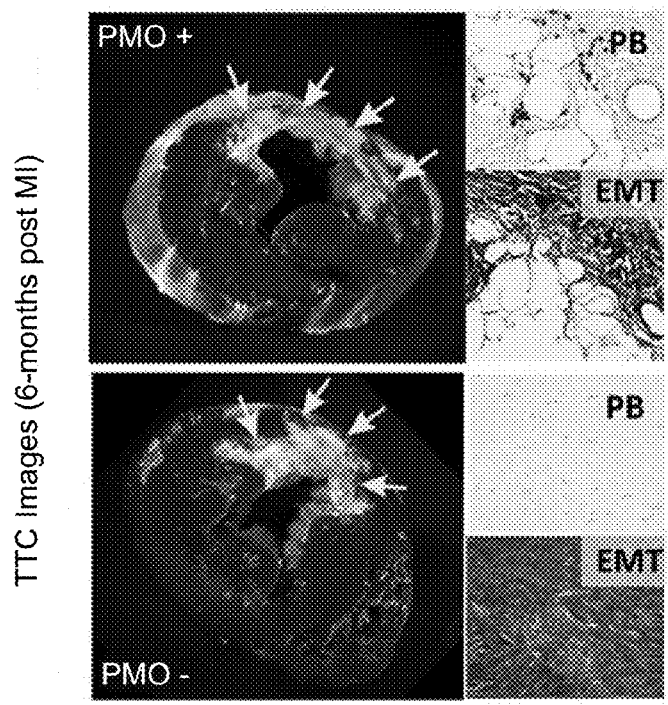
FIG. 21 depicts, in accordance with various embodiments of the present invention, iron deposits and infarct thinning at 6 months post MI. Iron-rich MIs are significantly thinner than those MI without iron at 6 month.

Without wishing to be bound by any particular theory, we believe that most, if not all, PMOs resolve into MI zones with ferric iron crystals and mediate adverse structural, functional and compositional remodeling. This is summarized in FIG. 17 (black arrows).

Figure 16:
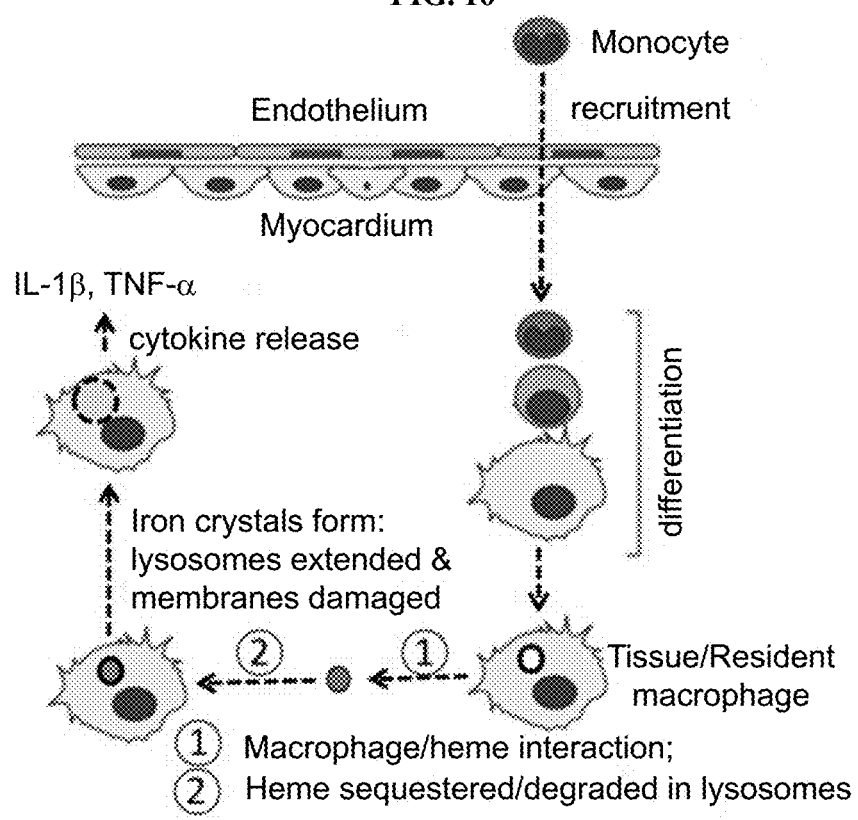
FIG. 16 depicts, in accordance with various embodiments of the present invention, iron crystals inducing inflammatory cytokine release in chronic MI. Monocytes recruited from blood, differentiating into tissue macrophages interact with byproducts of red blood cells from PMO and crystalize them within lysosomes. With greater uploading lysosomal membranes disrupt causing the macrophages to release proinflammatory cytokines (IL-1β, TNF-α).

I) Adverse Structural/Functional Remodeling:

Without wishing to be bound by any particular theory, we believe that when degraded red blood cells from PMO are internalized within lysosomes of macrophages, they crystalize; and when lysosomes are over-extended, their membranes are damaged causing macrophages to release proinflammatory cytokines (FIG. 16).

Crystals are Pro-Inflammatory:

The concept that crystalline material in tissue is proinflammatory and associated with chronic disease is recently well established. This has been particularly clear in gout, where uric acid crystals form and are phagocytosed by macrophages—leading to disruption of lysosomal membranes, inflammasome activation, and IL-1β production. A similar model has been proposed for a role for cholesterol crystals in promoting IL-1β- and inflammasome-dependent atherosclerosis and in silicosis, where silica crystals promote inflammasome- and IL-1β-dependent chronic inflammatory disease in the lungs. Lysosomal disruption and inflammasome activation are also linked to increased cell death, which can result in crystals being released and phagocytosed again by newly recruited macrophages. The result of this process is a chronic inflammatory loop—consistent with our early observations of the chronic phase of MI with iron.

Persistent Inflammation is Associated with Adverse Remodeling:

During the acute phase of MI, abundant pro-inflammatory monocytes are recruited to the site of infarct and regulate fibrogenic and angiogenic responses, which is crucial to cardiac repair. However, post MI LV remodeling is dependent on the timely inhibition and resolution of the inflammatory activity. Prolonged inflammation can impair collagen deposition and scar formation resulting in reduced tensile strength and LV dilatation. Ineffective suppression of inflammation post MI is associated with adverse LV remodeling of the heart. Macrophages are capable of dynamic phenotypic changes and can regulate both induction and suppression of inflammation following MI. Studies have shown that inflammatory cytokines (e.g., IL-1β, TNF-α) secreted by macrophages upregulate matrix metalloproteinase (MMP) and mediate adverse LV remodeling. But, the links between PMO, macrophage activation and inflammatory cytokine secretion in the chronic phase of MI was not known.

II) Fatty Remodeling of Infarction:

Without wishing to be bound by any particular theory, we also believe that the macrophages loaded with ferric iron accumulate fat. Fat infiltration is a newly recognized pathologic abnormality in MI and is linked to adverse outcome. However, the basis for fatty infiltration in MI remains unknown.

Fatty Infiltration is Associated with Iron Deposition in Chronic MI and MACE:

Historically, infiltration of fat cells (lipomatous metaplasia, LM) into the myocardium was an incidental finding. Now, there is extensive evidence that LM is commonly found in MI and is associated with MACE in chronic MI patients. In a recent CMR study of 316 post MI patients with at least 6-moth old MIs, ~25% of the patients had LM within their MI and was shown to be a key predictor of MACE. The role of iron in fatty infiltration has been extensively studied. Studies have shown that iron plays a critical role in foam cell accumulation. In atherosclerosis, iron-loaded macrophages have been shown to oxidize low-density lipoproteins and then transform into foam cells. Additionally, hepatic iron overload is known to initiate and promote steatosis in fatty liver disease.

Studies with Divalent Cation Chelators have not Proven to be Effective for MACE.

Recent Trial to Assess Chelation Therapy (TACT) in post MI patients showed that 6 months of EDTA therapy did not decrease MACE. Notably, EDTA is (a) not specific (or dosed) for ferric iron; (b) cannot cross cell membranes; and (c) known to mainly chelate divalent ions. Our data suggest that iron within MI is intracellular and is trivalent. Also, TACT did not stratify patients based on evidence of iron within MI.

Deferiprone is an effective and clinically approved intracellular iron chelator in the heart, but has not been evaluated for effects on PMO-driven iron deposition: Prior studies have explored iron chelation therapies in heart but they have been limited to acute phase of MI (i.e. 1-2 days post MI) and the results have been mixed. Iron chelation therapies have been used clinically to treat iron overload cardiomyopathies (thalassemia, Friedrich's ataxia, etc.). Early efforts used deferoxamine, which needed to be administered using a portable syringe system overnight due to its short half-life in plasma. Deferiprone, a more recent iron chelator, has significantly better characteristics: longer plasma life (which permits oral administration) and effective in clearing iron by entering cells at mild doses (~30 mg/kg/day). Deferiprone has also been shown to better with regards to safety, efficacy, and patient compliance than deferoxamine We Provide a Disease-Modifying Therapy for Reducing Adverse Remodeling in the Chronic Phase.

Without wishing to be bound by any particular theory, we believe that (a) PMO– driven iron deposition induces a pro-inflammatory macrophage phenotype, leading to accentuation and prolongation of the inflammatory response and causing adverse remodeling; and (b) therapies against this iron-mediated toxicity, such as deferiprone, a clinically approved intracellular chelator of ferric iron, may be a direct avenue for treating post MI patients.

First, we test and validate a CMR method for monitoring the extent of iron and fat within infarcted hearts over a 6-month period post MI in a clinically relevant animal model. Invasive angiography can assess perfusion during intervention but has limited capability for characterizing PMO. SPECT, CT, and echocardiography, are useful for detecting microvascular obstruction but are not suitable for serial assessment of iron (limited sensitivity and ionizing radiation). CMR is best available method for longitudinal myocardial characterization throughout the post MI period (high sensitivity and no ionizing radiation). Late-enhancement (LGE) CMR can accurately measure MI size, PMO, scar burden, infarct thinning; and cine CMR can accurately quantify remodeling indices. $T2^*$ CMR is the preferred method for diagnosing other cardiac iron overload disorders (e.g., thalassemia). But its accuracy for quantifying iron is reduced when fat is present; but this limitation can be overcome with confounder-corrected $T2^*$ mapping for quantifying iron and fat fraction in the same tissue. Post MI, although fat is typically not present at 8 weeks, by 6 months fat can be found within some MI.

Without wishing to be bound by any particular theory, we provide a novel pathophysiologic concept that may explain the link between PMO and adverse remodeling. Without wishing to be bound by any particular theory, we believe that PMO results in formation of crystalized iron deposits in the infarcted myocardium, activating a pro-inflammatory macrophage phenotype and promoting formation of foam cells. Prolonged macrophage-driven inflammation may accentuate adverse remodeling by activating matrix-degrading pathways and by perturbing formation of scar. This concept has important therapeutic implications. Without wishing to be bound by any particular theory, we believe that iron in ferric state enables the oxidation of LDL leading to accumulation of fat within macrophages. An intracellular iron chelator is used to reduce inflammation and fatty infiltrations within chronic MI. These mechanisms or therapeutic strategies have never been explored in chronic MIs.

Example 12

TABLE 2

Cardiac MRI Imaging Parameters

| Imaging Method | Cine | $T2^*$-weighted | LGE |
|---|---|---|---|
| Sequence | Balanced SSFP | Multiple GRE | IR-prepared GRE |
| TR (ms) | 3.1 | 12.0 | 3.0 |
| TE (ms) | 1.6 | 2.0-9.5 ($\Delta TE = 1.5$ ms) | 1.5 |
| Flip Angle | 40° | 10° | 25° |
| Bandwidth (Hz/pixel) | 930 | 930 | 586 |
| In-plane Resolution | | $1.4 \times 1.4$ mm$^2$ | |
| Slice Thickness | | 6 mm | |
| Other Parameters | 25-30 cardiac phases | 6 TEs | Optimal TI to null the remote myocardium |

Cardiac MRI Image Analysis

All CMR image analyses were performed on cvi$^{42}$ image processing software (Circle Cardiovascular Imaging Inc., Calgary, AB). Endocardial and epicardial contours were manually drawn on all images. Remote myocardium was identified on LGE images as the region showing no hyperintensity and a reference region-of-interest (ROI) was drawn in it. Infarcted myocardium was then defined on LGE images using the Mean+5 Standard Deviations (SD) technique relative to the reference ROI. Persistent microvascular obstruction (PMO) was defined as the hypointense core within the hyperintense infarcted myocardium identified on LGE images using the Mean+5SD criterion. For the sake of simplicity, the classic PMO arising from the no-reflow phenomenon in reperfused MIs is henceforth referred to as PMO, while the PMO observed on the day 7 LGE images in non-reperfused MIs is referred to as NR-PMO (non-reperfused persistent microvascular obstruction). Infarct size was calculated by summing the volumes of the hyperintense regions on LGE images identified using the Mean+5SD criterion and the hypointense PMO cores.

The presence of iron arising from blood degradation within infarcted myocardium were identified as hypointense regions on $T2^*$-weighted images confined to the hyperintense LGE territory. The reference ROIs drawn on LGE images were copied on to the corresponding $T2^*$-weighted images and the spatial extent of the hypointense regions on $T2^*$-weighted images were identified using the Mean-2SD criterion relative to the reference ROI. Off-resonance artifacts arising due to susceptibility differences at the heart-lung interface were manually excluded.

TABLE 3

Antibodies Used for Histopathology

| Histopathological Marker | Antibody Used |
|---|---|
| CD163 | Bioss, bs-2527R |
| Mac387 | Abcam, ab22506 |
| IL-1β | Abcam, ab34837 |
| TNF-α | Abcam, ab6671 |
| MMP-9 | Abcam, ab38898 |

Tables 4 and 5 (Functional Remodeling) below provide details on functional parameters and the corresponding changes observed between acute and chronic phases of reperfused and non-reperfused myocardial infarctions

TABLE 4

Functional LV Remodeling Following Reperfused Myocardial Infarctions
REPERFUSED MYOCARDIAL INFARCTION

| Group | Parameter | End-Diastolic Volume (mL/m$^2$) | End-Systolic Volume (mL/m$^2$) | Ejection Fraction (%) |
|---|---|---|---|---|
| PMO+/$T_2^*$+ (n = 9) | Acute | 67.2 ± 11.2 | 47.8 ± 12.6 | 29.4 ± 9.7 |
| | Chronic | 75.9 ± 12.2 | 58.0 ± 14.3 | 20.2 ± 11.3 |
| | % Change (Acute to Chronic) | 15.6 ± 10.6 | 20.9 ± 14.3 | −22.3 ± 14.3 |
| | p-value (Acute vs. Chronic) | 0.04* | 0.03* | 0.03* |
| PMO+/$T_2^*$− (n = 4) | Acute | 56.3 ± 8.8 | 33.9 ± 10.8 | 39.6 ± 11.2 |
| | Chronic | 59.9 ± 9.6 | 34.5 ± 12.6 | 43.0 ± 9.8 |
| | % Change (Acute to Chronic) | 5.3 ± 12.6 | 1.1 ± 11.1 | 1.5 ± 11.5 |
| | p-value (Acute vs. Chronic) | 0.30 | 0.87 | 0.81 |

TABLE 4-continued

Functional LV Remodeling Following
Reperfused Myocardial Infarctions
REPERFUSED MYOCARDIAL INFARCTION

| Group | Parameter | End-Diastolic Volume (mL/m$^2$) | End-Systolic Volume (mL/m$^2$) | Ejection Fraction (%) |
|---|---|---|---|---|
| PMO−/T$_2$*− (n = 4) | Acute | 47.5 ± 8.3 | 27.0 ± 5.6 | 47.6 ± 9.7 |
| | Chronic | 44.6 ± 9.7 | 23.8 ± 6.4 | 46.8 ± 10.2 |
| | % Change (Acute to Chronic) | −6.1 ± 15.1 | −10.0 ± 14.2 | −0.3 ± 9.0 |
| | p-value (Acute vs. Chronic) | 0.11 | 0.57 | 0.98 |

TABLE 5

Functional LV Remodeling Following
Non-Reperfused Myocardial Infarctions
NON-REPERFUSED

| Group | Parameter | End-Diastolic Volume (mL/m$^2$) | End-Systolic Volume (mL/m$^2$) | Ejection Fraction (%) |
|---|---|---|---|---|
| NR− PMO+/T$_2$*+ (n = 16) | Acute | 61.8 ± 9.9 | 39.9 ± 8.6 | 35.9 ± 6.2 |
| | Chronic | 74.3 ± 9.2 | 46.1 ± 8.7 | 37.9 ± 8.5 |
| | % Change (Acute to Chronic) | 21.2 ± 11.3 | 17.3 ± 16.2 | 5.6 ± 15.6 |
| | p-value (Acute vs. Chronic) | <0.001* | 0.001* | 0.17 |
| NR− PMO−/T$_2$*− (n = 1) | Acute | 56.0 | 34.0 | 42.4 |
| | Chronic | 67.0 | 37.0 | 44.8 |
| | % Change (Acute to Chronic) | 19.6 | 8.8 | 5.6 |
| | p-value (Acute vs. Chronic) | — | — | — |

Example 13 Persistent Microvascular Obstruction Culminates in the Confluence of Iron Oxide Nanocrystal Formation, Proinflammatory Burden and Adverse Left Ventricular Remodeling in Chronic Myocardial Infarction Emerging evidence now supports the notion that persistent microvascular obstruction (PMO) may be more predictive of major adverse cardiovascular events than MI size itself. But, how PMO, a phenomenon limited to the acute/sub-acute period of MI, imparts adverse remodeling throughout the post MI period, particularly after its resolution, is incompletely understood. Without wishing to be bound by any particular theory, we believe that PMOs resolve into chronic iron crystals within MI territories and actively impart a proinflammatory burden and adverse remodeling of infarction and LV in the chronic phase of MI.

Canine models reperfused (n=20) and non-reperfused (n=20) with and without PMO were studied with serial cardiac MRI to characterize the spatiotemporal relationships between PMO, iron deposition, and infarct and LV remodeling indices between acute (day 7, post MI) and chronic (week 8, post MI). Histopathology and immunohistochemistry were used to validate the iron deposition, microscopically map and quantify the relationship between iron-rich chronic MI regions against pro-inflammatory macrophages, proinflammatory cytokines and matrix metalloproteinase. Atomic resolution transmission electron microscopy (TEM) was used to determine the crystallinty of iron and assess the physical effects of iron on lysosomes within macrophages and energy-dispersive X-ray spectroscopy (EDS) to identify the chemical composition of the iron composite. Results showed that PMOs lead to iron deposition within chronic MI and that the extent of chronic iron deposition is strongly related to PMO Volume (r>0.6, p<0.001). TEM and EDS analysis showed that iron within chronic MI is found within macrophages as aggregates of nanocrystals of ~2.5 nm diameter in ferric state. Correlative histological studies showed that iron content, proinflammatory burden and collagen degrading enzyme were highly correlated (r>0.7, p<0.001). Iron within chronic MI was significantly associated with infarct resorption (r>0.5, p<0.001) and adverse structural (r>0.5, p<0.001) remodeling.

Territories of PMO in the acute phase of MI resolve into iron oxide nanocrystals in ferric state in the chronic phase of MI. The amount of iron deposition is determined by the extent of persistent microvascular obstruction and is directly related to the extent of pro-inflammatory burden, infarct thinning and adverse LV remodeling. Resolution of PMO into iron deposition could be a contributing source to the adverse remodeling of the heart in the chronic phase of MI.

Infarct size is long known to be an independent predictor of adverse left-ventricular (LV) remodeling in the post myocardial infarction (MI) period. In addition to infarct size, several clinical and pre-clinical studies have shown that the extent of microvascular obstruction (MO) is an important independent predictor of adverse LV remodeling. Emerging evidence now supports the notion that MO may be more predictive of major adverse cardiovascular events (MACE) than infarct size itself. Several studies have suggested recruitment of inflammatory cells into the core of infarction is prohibited leading to delayed infarct healing. But, how MO, a phenomenon limited to the acute/sub-acute period of MI, imparts adverse remodeling throughout the post MI period, particularly after its resolution, is incompletely understood.

Recent studies have shown that MO is frequently accompanied by reperfusion hemorrhage and that it is these types of MIs that remodel the worst and are at the greatest risk for MACE. Serial imaging studies along with histological evidence have shown that reperfusion hemorrhage leads to chronic iron deposition, which is associated with prolonged recruitment of macrophages. However, the physiochemical characteristics of the iron deposits within the infarcted myocardium, the phenotypes of the macrophages in iron-rich infarct regions, and their relation to infarct remodeling or the global structural/functional LV remodeling are not known. Moreover, MO is not always accompanied by acute reperfusion hemorrhage, but infarctions with MOs in the absence of hemorrhage also have significantly poor outcome over infarctions without MO. Thus, even if post MI iron influences remodeling of hemorrhagic MI in the chronic period, this would not explain the outcomes associated with infarctions with MO but no hemorrhage.

Among the methods used for noninvasively characterizing MO, the hypointense core within late-gadolinium enhancement (LGE) cardiac magnetic resonance imaging (CMR) at 7-10 days post MI (referred below as persistent MO, PMO) has emerged as a reliable means for detecting MOs that are associated with adverse outcomes. In this study we investigated the fate of acute MIs with PMO (with and without reperfusion hemorrhage) in the chronic phase to elucidate the interplay between (a) the compositional changes in PMO territories; (b) inflammatory response; and (c) adverse remodeling of infarct zone and LV. Specifically, without wishing to be bound by any particular theory, we believe that (a) every PMO (with or without reperfusion hemorrhage) resolves into crystallized iron in ferric state with the amount of iron deposition dependent on the size of PMO; and (b) the magnitude of iron deposition is related to proinflammatory burden and a potent, independent, predictor of adverse infarct and LV remodeling. We used canine models infarction with PMO (with and without hemorrhage) and serial CMR to characterize the spatiotemporal relationships between PMO, iron deposition, and infarct and LV remodeling indices. We used histopathology to validate the iron deposition, microscopically map and quantify the relationship between iron-rich chronic MI regions against proinflammatory macrophages and cytokines and assess collagen metabolism. In addition, we used atomic resolution transmission electron microscopy (TEM) to determine the crystallinty of iron and assess the physical effects of iron on lysosomes within macrophages, energy-dispersive X-ray spectroscopy (EDS) to identify the chemical composition of the iron composite.

Methods

Animal Preparation and CMR Protocol

Canines (n=40) were studied according to the protocols approved by the institutional Animal Care and Use Committee. Twenty canines were subjected to ischemia-reperfusion injury by occluding the left anterior descending (LAD) artery for 3 hours followed by reperfusion (Reperfused Group). The remaining 20 canines were subjected to permanent ligation of the LAD (Non-Reperfused Group). All canines underwent CMR at 7 days (acute) and 56 days (chronic) post-MI on a 3 T clinical MRI system (MAGNETOM Verio, Erlangen, Siemens Healthcare). ECG-triggered breath-held 2D Cine-SSFP, $T_2$*-weighted, and Late Gadolinium Enhancement (LGE) images were acquired (refer to the Table 2 for imaging parameters). Animals were euthanized following the day 56 CMR scan and their hearts were excised for histological examination.

CMR Image Analyses

All CMR image analyses were performed on cvi$^{42}$ image processing software (Circle Cardiovascular Imaging Inc., Calgary, AB, Canada). LV structural remodeling was quantified using end-diastolic sphericity index (EDSI) measurements from cine-SSFP images. LV functional remodeling was quantified using end-diastolic volume (EDV), end-systolic volume (ESV), and ejection fraction (EF) measurements from cine-SSFP images normalized to the body surface area. Percentage change in the LV structure and function parameters ($\Delta$EDSI, $\Delta$EDV, $\Delta$ESV, and $\Delta$EF) between the acute and chronic phases post-MI were also calculated. Semi-automatic thresholding was used to identify infarcted myocardium and persistent microvascular obstruction (PMO) from LGE images (refer to the "Cardiac MRI Image Analysis" section in Example 12 for additional details). For the sake of simplicity, the classic PMO arising from the no-reflow phenomenon in reperfused MIs is henceforth referred to as PMO, while the PMO observed on the day 7 LGE images in non-reperfused MIs is referred to as NR-PMO (non-reperfused persistent microvascular obstruction). Hypointense regions on T2*-weighted images confined to the hyperintense LGE territory, indicative of iron arising from blood degradation within infarcted myocardium, were quantified using semi-automatic thresholding.

Based on the presence or absence of PMO and iron within the infarcted territories at 7 days post-MI, canines from the Reperfused group were classified as PMO$^+$/T2*$^+$ (both PMO and T2* loss are present), PMO$^+$/T2*$^-$ (PMO is present but T2* loss is absent), PMO$^-$/T2*$^+$ (PMO is absent but T2* loss is present), and PMO–/T2*$^-$ (both PMO and T2* loss are absent). Similarly, based on the presence or absence of NR-PMO and iron within the infarcted territories on day 7 post-MI, canines from the Non-Reperfused group were classified as NR-PMO$^+$/T2*$^+$, NR-PMO$^+$/T2*$^-$, NR-PMO$^-$/T2*$^+$, and NR-PMO$^-$/T2*$^-$. Infarct, PMO, and iron volumes were calculated at both acute and chronic phases across all the groups as the percentage of total LV myocardial volume. Infarct resorption was quantified as the absolute change in infarct volume normalized to LV volume (% LV) between acute and chronic phases. T2* values of the remote myocardium, entire infarcted myocardium, and the iron deposits within the infarcted myocardium were also measured.

Histopathological Validation and Quantification of Inflammatory Burden and Collagen Degradation Freshly explanted hearts from the canines were sectioned along the short-axis direction from base to apex into 1-cm thick slices. Infarcted and remote territories were identified on the basis of TTC staining. Ex-vivo 2D $T_2$*-weighted images (same parameters were used as those for the in-vivo images) were subsequently acquired from the slices positive for MI on TTC staining. Based on the presence of hypointense cores within the infarcted territories on the ex-vivo $T_2$*-weighted images, slices were classified as those with and without iron deposition ($T_2$*+ and $T_2$*– respectively). Paraffin-embedded serial sections (5 μm) from representative segments of infarcted and remote areas were stained with H&E stain for necrosis, EMT stain for fibrosis, and Perl's stain for iron deposition. For immunostaining, sections were probed with antibodies against the markers of canine macrophages (Mac387 and CD163), proinflammatory cytokines (IL-1 and TNF-$\alpha$) and matrix metalloprotinease (MMP-9) (refer to Table 3 for additional details). All quantitative histological analyses were performed following digitization of slides on ScanScope AT (Aperio Technologies, Vista, Calif.). Morphometric analysis was performed using Definiens Tissue Studio (Definiens, Parsippany, N.J.) software. Predefined stain-specific algorithms and classification tools were created utilizing Definiens eCognitionNetwork Language™ to identify positive and negative stained area under the marker (for every 1 μm$^2$) within each tissue region in an automated fashion to reduce operator bias. Thresholds were set to classify the following: blue for iron, and DAB stain for CD163, Mac387, IL-1$\beta$, TNF-$\alpha$, and MMP-9.

Transmission Electron Microscopy, Atomic Resolution Imaging and Energy-Dispersive X-Ray Spectroscopy (EDS)

Sections positive for iron from ex-vivo sections were sectioned further into 1 mm$^3$ and fixed in 2.5% glutaraldehyde (Electron Microscopy Sciences (EMS), Hatfield, Pa.) and processed by washing them with dH$_2$O, and a gradual dehydration by using ethanol series (25%, 33, 50, 75, and 3×100% ethanol). The traditional stains for contrast enhancement such as OsO$_4$ were purposely omitted to preserve the redox state of the biominerals. Samples were then infiltrated in LR White acrylic resin (EMS), and polymerized at 60° C. for 24 hours. The hardened resin blocks were sectioned on a Leica EM UC6 ultra-microtome using a 45 diamond knife (Diatome). 70-nm thick sections were collected on Cu grids coated with ultrathin carbon film on holey carbon support film (Ted Pella, Inc., Redding, Calif.) and imaged on a Tecnai T-12 TEM (FEI, Hillsboro, Oreg.) with a LaB6 filament, operating at 120 kV. Images were collected digitally with a 2×2K Ultrascan 1000 CCD (Gatan). For the atomic resolution imaging, the previously identified areas of interest were correlatively imaged using Titan S/TEM (FEI), operating at 300 kV. The elemental analysis was performed with energy dispersive spectroscopy, using a Si(Li) detector (EDAX), coupled to the STEM.

Statistical Analyses

All statistical analyses were performed using IBM SPSS Statistics (version 21.0, IBM Corporation, Armonk, N.Y.). Shapiro-Wilk test and quantile-quantile plots were used to test the normality of the data. Depending on the normality of the data, analysis of variance or Kruskal-Wallis test along with post-hoc analyses were used to compare measurements among the different canine groups. Bonferroni correction was used for multiple comparisons. Univariate and multivariate linear regression analyses were performed to determine the associations among different measurement variables. Statistical significance was set at p<0.05. Normal data is expressed as Mean±SD, while non-normal data is expressed as Median with interquartile range.

Results

Three canines within the Reperfused group and four canines from the Non-Reperfused group died within the first week post-MI. The remaining 17 canines from the Reperfused group and 16 canines from the Non-Reperfused group sustained MIs as confirmed by LGE images on day 7.

Persistent Microvascular Obstructions Lead to Iron Deposition within Chronic MI

A. Chronic Iron Deposition in Reperfused MIs: CMR Findings

Figure 22:
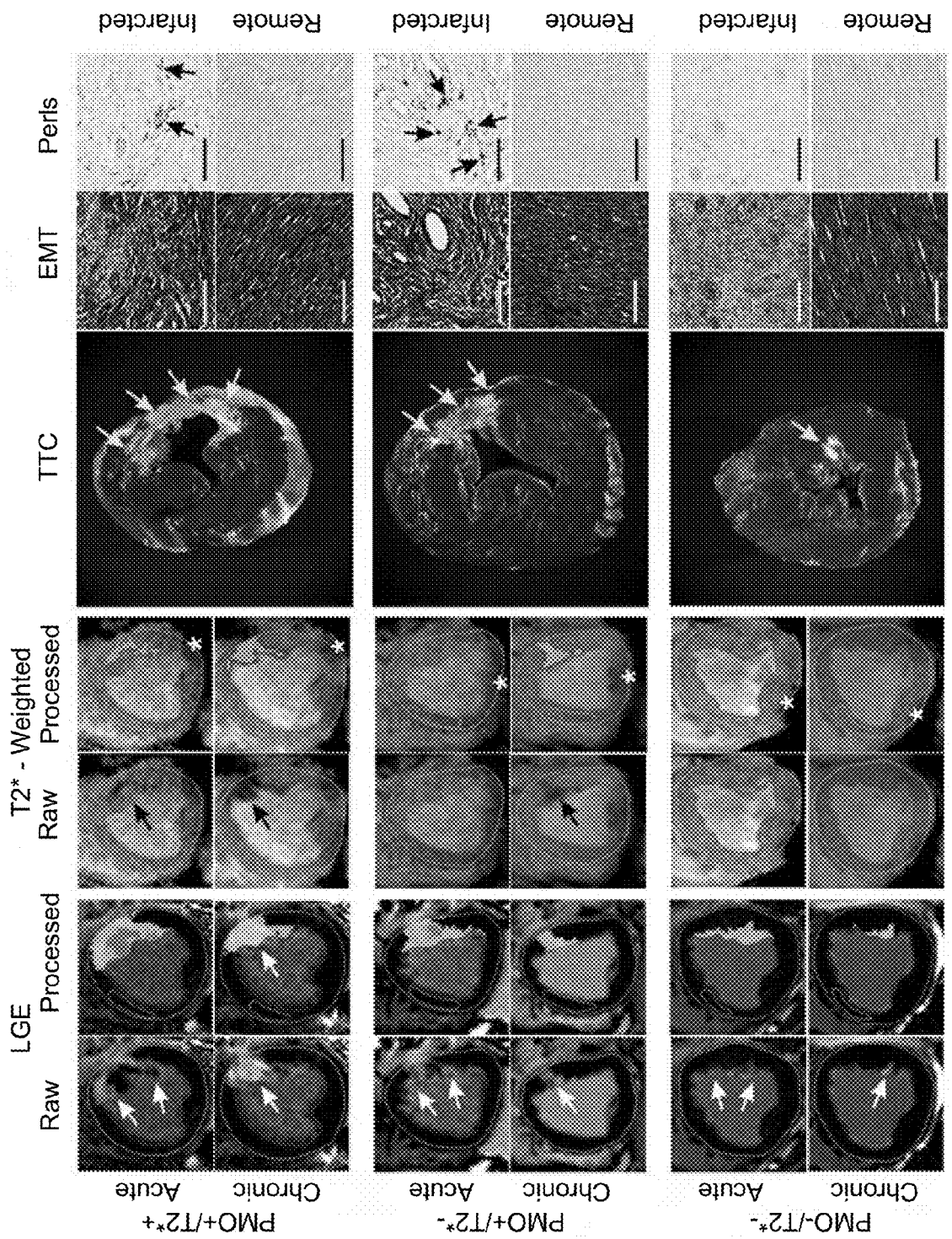
FIG. 22 depicts, in accordance with various embodiments of the present invention, chronic iron deposition in reperfused myocardial infarctions. Representative in-vivo raw and processed LGE and $T_2^*$-weighted images from Reperfused canines acquired in both acute and chronic phases post-MI are shown. Arrows point to the sites of MI and iron deposition on LGE and $T_2^*$-weighted images respectively. Corresponding ex-vivo histological sections stained with TTC, EMT and Perls stain are also shown. Note the significant chronic iron deposition in the $PMO^-/T_2^{*-}$ group, despite the absence of acute reperfusion hemorrhage. Perls stain confirmed the presence of chronic iron deposition (blue deposits pointed at by the arrows) in the $PMO^+/T_2^{*+}$ and $PMO^+/T_2^{*-}$ groups, but not in the $PMO^-/T_2^{*-}$ group. Asterisks in the $T_2^*$-weighted images point to the sites of off-resonance artifacts that were manually excluded in the final analysis.

Within the Reperfused group, 9 canines were classified as $PMO^+/T2^{*+}$, 4 canines were classified as $PMO^+/T2^{*-}$, and 4 canines were classified as $PMO^-/T2^{*-}$ at 7 days post-MI. None of the reperfused canines showed iron deposition within the infarcted territories in the absence of PMO on day 7 post-MI. Representative T2*-weighted and LGE images from the $PMO^+/T2^{*+}$, $PMO^+/T2^{*-}$, and $PMO^-/T2^{*-}$ groups in both acute and chronic phases are shown in FIG. 22, along with corresponding ex-vivo histology sections stained with TTC, EMT, and Perl's stains. No PMO could be observed on LGE images in all the 3 groups in the chronic phase. In the PMO+/T2*+ group, significant T2* losses indicative of iron deposition could be visually observed in all the canines within the infarcted territories in both acute and chronic phases. While none of the canines in the $PMO^+/T2^{*-}$ showed T2* losses within the infarct in the acute phase, all the canines subsequently showed significant T2* losses within the infarct in the chronic phase. None of the canines in the $PMO^-/T2^{*-}$ group showed any T2* losses within the infarct in both acute and chronic phases. TTC images confirmed the presence of infarction in all the groups (FIG. 22). Perls staining further confirmed the presence of iron deposition in the chronic phase in the $PMO^+/T2^{*+}$ and $PMO^+/T2^{*-}$ groups, and the absence of iron deposition in the $PMO^-/T2^{*-}$ group (FIG. 22).

B. Chronic Iron Deposition in Non-Reperfused MIs: CMR Findings

Figure 23:
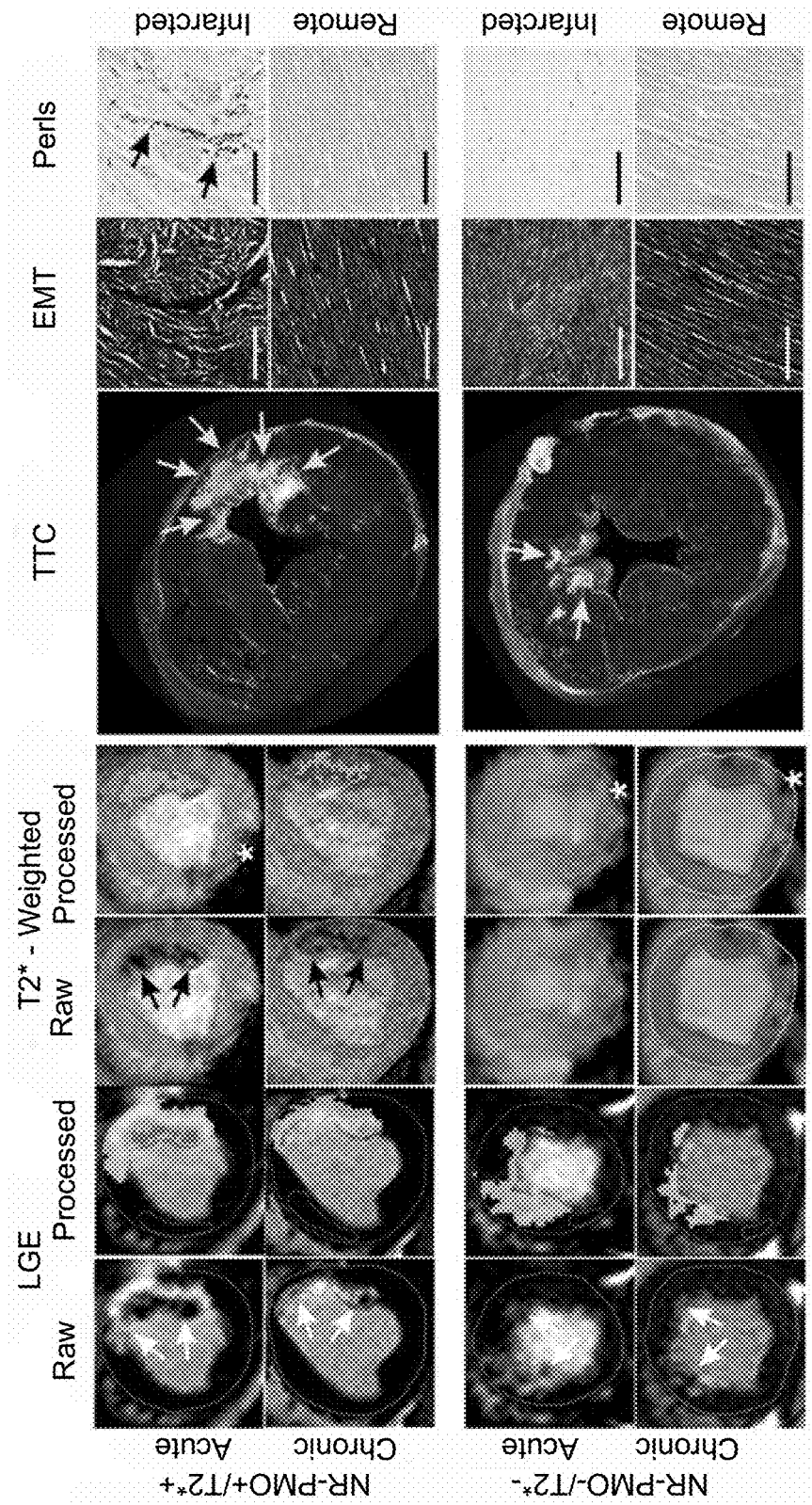
FIG. 23 depicts, in accordance with various embodiments of the present invention, chronic iron deposition in non-reperfused myocardial infarctions. Representative in-vivo raw and processed LGE and $T_2^*$-weighted images from Non-reperfused canines acquired in both acute and chronic phases post-MI are shown. Arrows point to the sites of MI and iron deposition on LGE and $T_2^*$-weighted images respectively. Corresponding ex-vivo histological sections stained with TTC, EMT and Perls stain are also shown. Note the significant chronic iron deposition in the $NR-PMO^-/T_2^{*+}$ group as observed on the in-vivo $T_2^*$-weighted images. Perls stain confirmed the presence of chronic iron deposition (blue deposits pointed at by the arrows) in the $NR-PMO^-/T_2^{*+}$ group, but not in the $NR-PMO^-/T_2^{*-}$ group. Asterisks in the $T_2^*$-weighted images point to the sites of off-resonance artifacts that were manually excluded in the final analysis.

Within the Non-Reperfused group, 15 canines were classified as $NR-PMO^+/T_2^{*+}$, and 1 canine was classified as $NR-PMO^-/T_2^{*-}$. No canine was classified as either $NR-PMO^+/T_2^{*+}$ or $NR-PMO^-/T_2^{*-}$. Representative T2*-weighted and LGE images from the $NR-PMO^+/T_2^{*+}$ and $NR-PMO^-/T_2^{*-}$ groups in both acute and chronic phases are shown in FIG. 23, along with corresponding ex-vivo histology sections stained with TTC, EMT, and Perl's stains. No PMO could be observed on LGE images in both of the groups in the chronic phase. In the $NR-PMO^+/T_2^{*+}$ group, significant T2* losses indicative of iron deposition could be visually observed in all the canines within the infarcted territories in both acute and chronic phases. The only canine in the $NR-PMO^-/T_2^{*-}$ group did not show any T2* losses within the infarct in both acute and chronic phases. TTC images confirmed the presence of MI in all the groups (FIG. 23). Perls staining further confirmed the presence of iron deposition in the chronic phase in the $NR-PMO^+/T_2^{*+}$ group, but not in the $NR-PMO^-/T2^{*-}$ group.

Extent of Chronic Iron Deposition is Strongly Related to Acute PMO Volume

A. Infarct, PMO, and Iron Volumes in Reperfused MIs

Figure 24A:
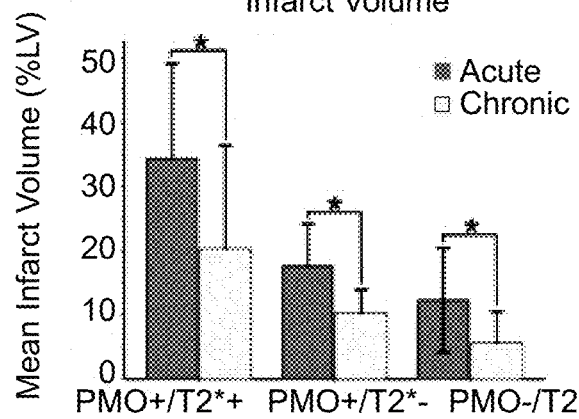
FIGS. 24A-24H depict, in accordance with various embodiments of the present invention, infarct, PMO, and iron volumes in reperfused and non-reperfused myocardial infarctions. Mean infarct volume (% LV, FIG. 24A), PMO volume (% LV, FIG. 24B), iron volume (% LV, FIG. 24C), and relationships between PMO volume with acute and chronic iron volumes (FIG. 24D) are shown from canines with reperfused MIs. Similarly, mean infarct volume (% LV, FIG. 24E), NR-PMO volume (% LV, FIG. 24F), iron volume (% LV, FIG. 24G), and relationships between PMO volume with acute and chronic iron volumes (FIG. 24H) are shown from canines with non-reperfused MIs. * denotes statistically significant differences (p<0.05).
Figure 24B:
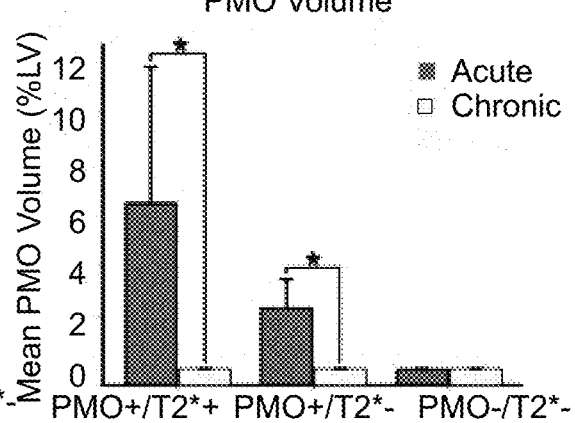
Figure 24C:
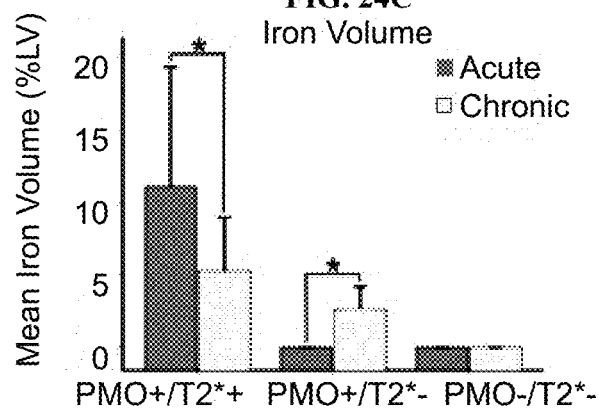
Figure 24D:
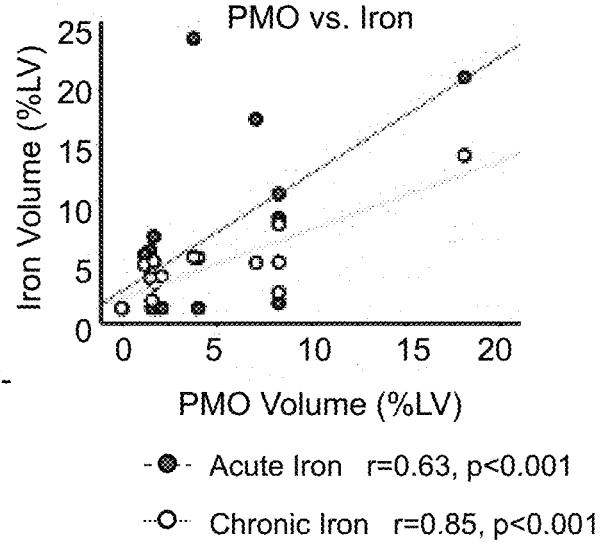

In the reperfused MIs, mean acute infarct volume in the $PMO^+/T_2^{*+}$ group (33.9±15.1%) was significantly higher than that of $PMO^+/T_2^{*-}$ group (17.6±6.6%, p<0.001) and the $PMO^-/T2^{*-}$ group (12.2±8.1%; FIG. 24A). Mean acute PMO volume in the $PMO^+/T_2^{*+}$ group (6.1±6.6%) was also significantly higher than that of the $PMO^+/T_2^{*-}$ group (2.4±1.1%, p<0.001; FIG. 24B). In the chronic phase, mean infarct volume in the $PMO^+/T_2^{*+}$ group (20.9±15.6%; FIG. 24A) was significantly higher than that of $PMO^+/T_2^{*-}$ group (10.2±3.8%, p<0.001) and the $PMO^-/T_2^{*-}$ group (5.64.9%, p<0.001). Mean infarct volume decreased significantly between acute and chronic phases across all the groups (p<0.001 for all cases). Mean chronic iron volume in the $PMO^+/T_2^{*+}$ group (5.3±3.7%) was also significantly higher than that of the $PMO^+/T_2^{*-}$ group (2.6±1.6%, p<0.001; FIG. 24C). Relative to the acute phase, mean iron volume in the chronic phase decreased significantly in the $PMO^+/T_2^{*+}$ group (9.3±6.6% vs. 5.3±3.7%, p=0.02; FIG. 24C). In contrast, mean iron volume in the $PMO^+/T_2^{*-}$ group increased from 0 in the acute phase to 2.6±1.6% (p=0.01; FIG. 24C). Significant linear relationships were observed between the PMO volume and acute iron volume (r=0.63, p<0.001; FIG. 24D), and PMO volume and chronic iron volume (r=0.85, p<0.001; FIG. 24D).

B. Infarct, PMO, and Iron Volumes in Non-Reperfused MIs

Figure 24E:
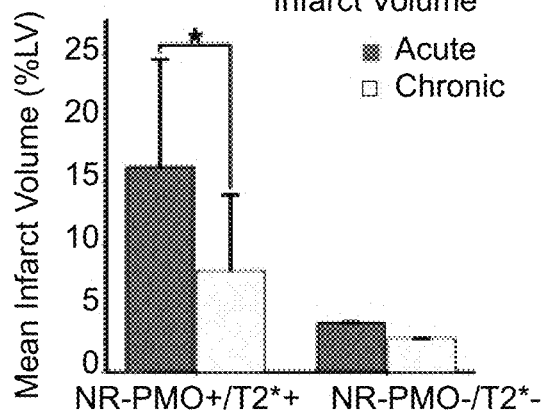
Figure 24F:
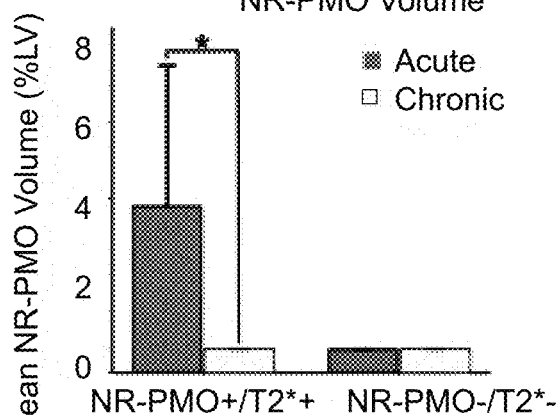
Figure 24G:
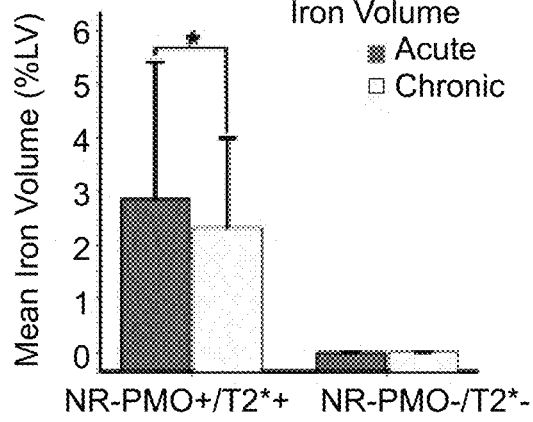
Figure 24H:
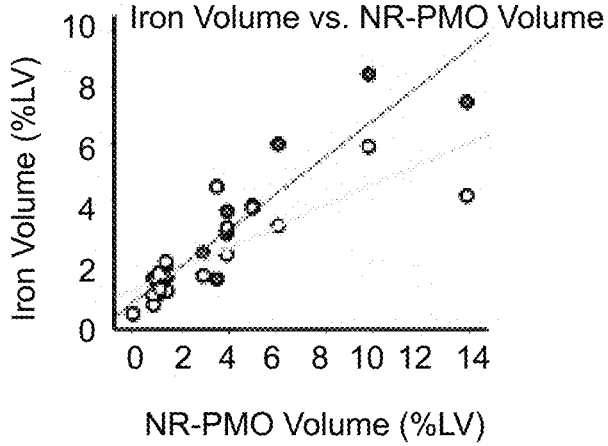

In the non-reperfused MIs, mean infarct volume in the $NR-PMO^+/T_2^{*+}$ group was significantly higher than that of $NR-PMO^-/T_2^{*-}$ group in both acute (15.4±8.7% vs. 3.9%, p<0.001) and chronic phases (7.6±5.9% vs. 2.6%, p<0.001; FIG. 24E). Mean infarct volume decreased significantly between acute and chronic phases in both the groups (p<0.001 for both cases). Relative to the acute phase, mean iron volume in the chronic phase decreased significantly in the $NR-PMO^+/T_2^{*+}$ group (2.7±2.5% vs. 2.2±1.7%, p=0.02; FIG. 24G). Significant linear relationships were observed between the NR-PMO volume and acute iron volume (r=0.93, p<0.001; FIG. 24H), and NR-PMO volume and chronic iron volume (r=0.81, p<0.001; FIG. 24H).

Iron Accumulates within Chronic Infarction Territories as Nanocrystals

Figure 26A:
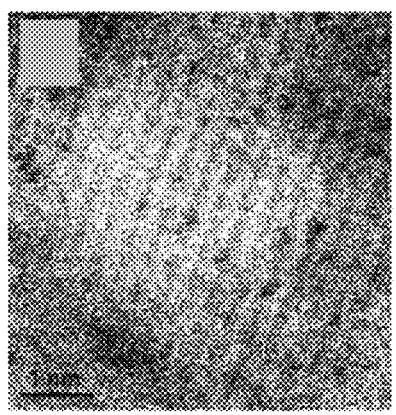
FIGS. 26A-26C depict, in accordance with various embodiments of the present invention, physiochemical characterization of crystalline iron within macrophages.
Figure 26B:
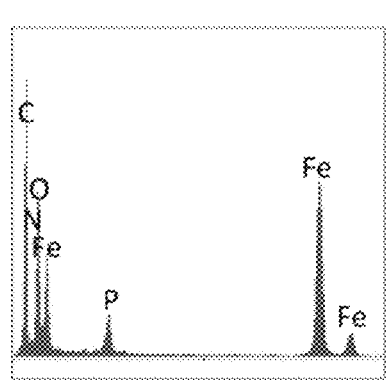
Figure 26C:
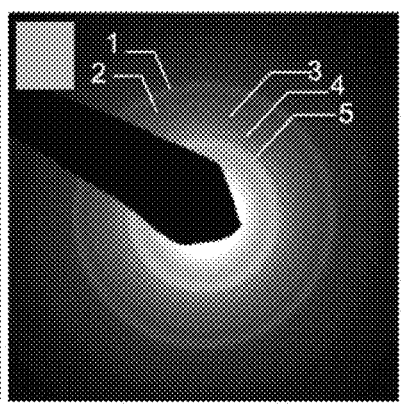

TEM of myocardial sections of chronic infarction, identified to be positive for iron from ex-vivo T2* CMR, revealed the presence of electron dense materials within macrophages that were organized into nodules (~200 nm in diameter; FIGS. 25A-25E). The individual nodules were themselves found to be composed of highly crystalline nanoparticles (~2.5-nm in diameter). A closer look at the electron dense material showed that the material to be enclosed by membranes of spherical organelles suggestive of lysosomes. Atomic resolution scanning TEM of the particulate matter showed highly ordered pattern of atoms and the EDS spectrum showed a strong presence of iron with diffraction pattern (with diffraction rings at 0.150 nm, 0.176 nm, 0.214 nm, 0.226 nm, and 0.256 nm) that was an exact fit with 6-line hydroxy ferrihydrite (FIGS. 26A-26C), which has the chemical formula of $5Fe_2O_3 \cdot 9H_2O$ with iron in Fe(III) state.

Figure 27A:
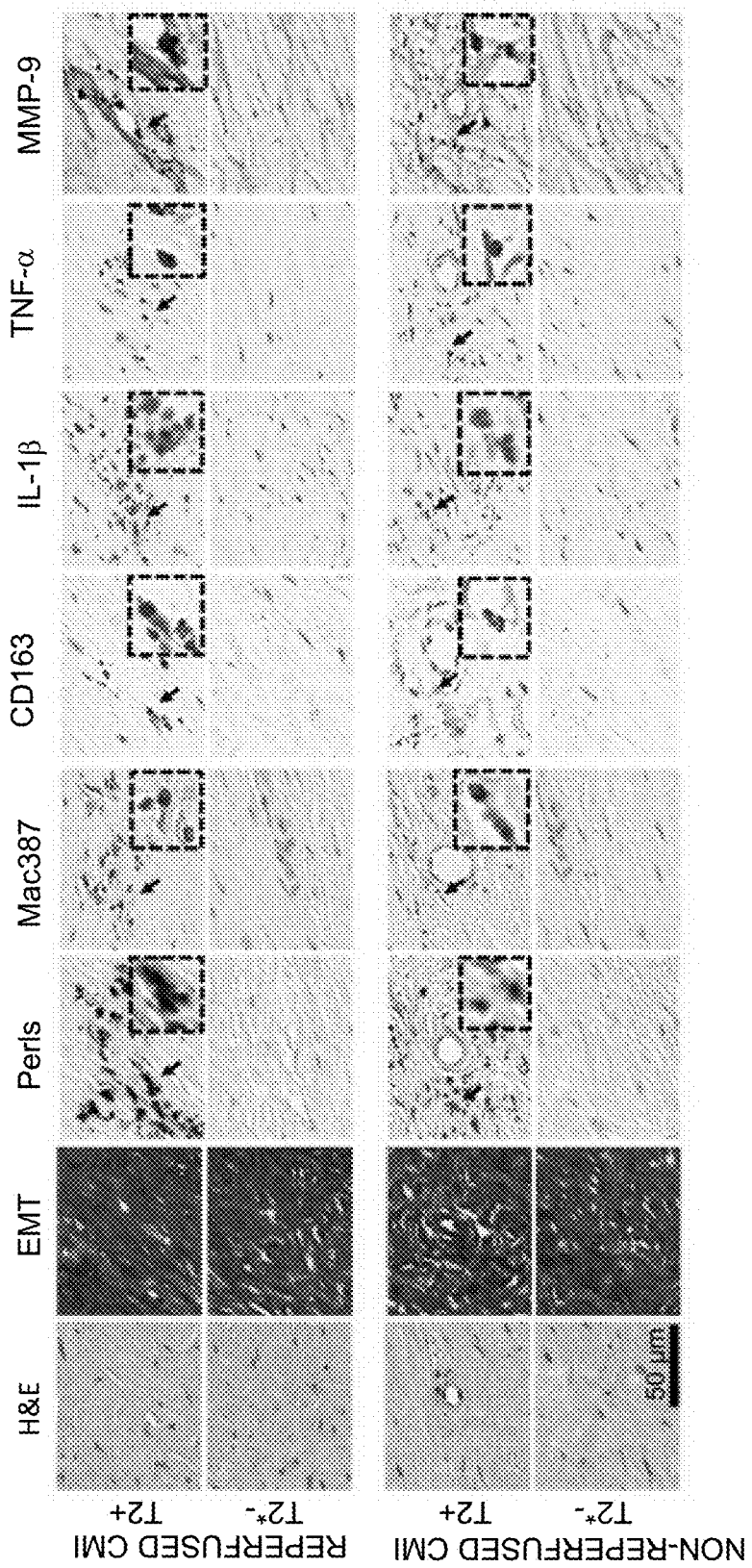

Iron Content, Proinflammatory Burden and Collagen Degradation are Highly Correlated Representative microscopic immunohistological sections of reperfused and non-reperfused MIs obtained from canines with and without $T_2^*$ losses ($T_2^*+$ and $T_2^*-$ respectively) as observed on ex-vivo $T_2^*$-weighted images are shown in FIG. 27A. Significant collagen deposition within the infarcted territories could be observed in all cases, while Perl's stain confirmed the presence of iron deposition only in the $T_2^*+$ cases. Significant co-localization of Mac387+ cells with iron deposits was observed in both reperfused and non-reperfused MIs. There was intense IL-1β and TNF-α immunoreactivity associated with Mac387+ cells. Linear regression analyses showed strong associations of area of iron (Perl's stain) with area of, area of Mac387+ cells (r=0.93, p<0.001; FIG. 27B), CD163+ cells (r=0.80, p<0.001; FIG. 27C), area of IL-1β activity (r=0.73, p<0.001; FIG. 27D), area of TNF-α activity (r=0.85, p<0.001; FIG. 27E), and area of MMP-9 activity (r=0.92, p<0.001; FIG. 27F).

Figure 28A:
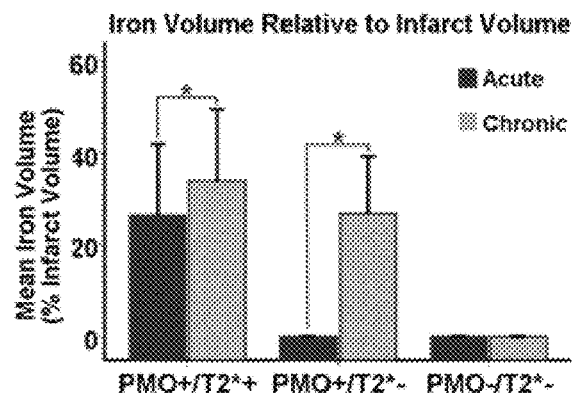
FIGS. 28A-28D depict, in accordance with various embodiments of the present invention, relationship between iron volume and infarct remodeling in reperfused and non-reperfused myocardial infarctions. Mean iron volume as a fraction of infarct volume (both normalized to LV volumes) in acute and chronic phases of infarctions is shown in FIG. 28A (reperfused MI) and FIG. 28C (non-reperfused MI). The relationship between infarct resorption as a function of acute and chronic iron volumes are shown in FIG. 28B (non-reperfused MI) and FIG. 28D (non-reperfused MI). *denotes statistically significant differences (p<0.05); and † denotes no statistically significant differences (p>0.05).
Figure 28B:
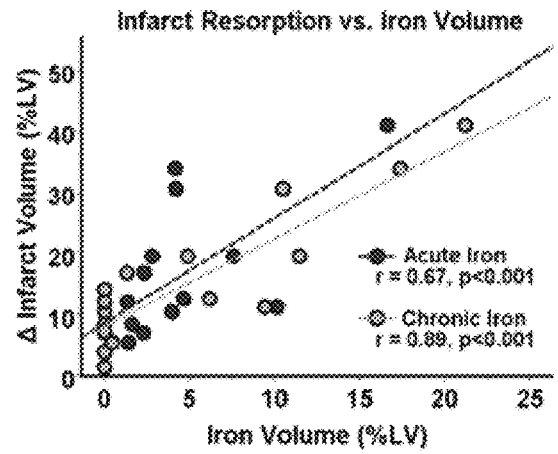
Figure 28C:
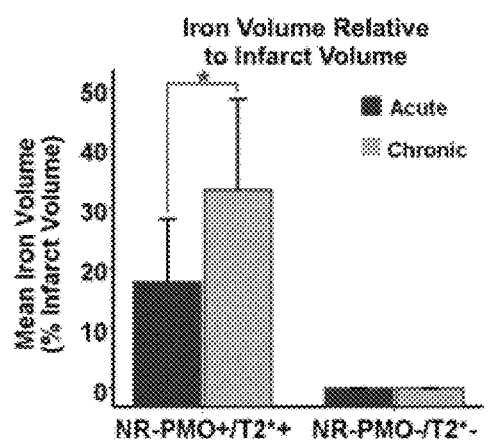
Figure 28D:
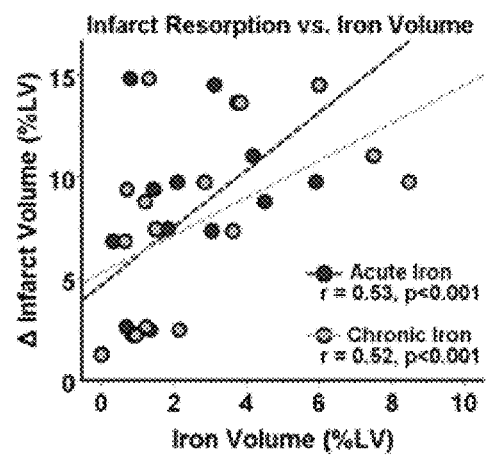

Iron within Chronic MI is Associated with Adverse Remodeling if Chronic Infarction Relationship Between Iron Volume and Infarct Remodeling In reperfused MIs, mean iron volume calculated as a percentage of the total infarct volume significantly increased between acute and chronic phases in both $PMO^+/T_2^{*+}$ (26.3±15.6% vs. 33.8±15.5%, p=0.003) and $PMO^+/T_2^{*-}$ groups (0 vs. 26.7±12.5%, p<0.001; FIG. 28A). Infarct resorption was linearly related to both acute (r=0.67, p<0.001) and chronic iron volumes (r=0.89, p<0.001; FIG. 28B). In non-reperfused MIs, mean iron volume calculated as a percentage of the total infarct volume significantly increased between acute and chronic phases in the $NR\text{-}PMO^+/T_2^{*+}$ group (17.7±10.5% vs. 33.2±15.1%, p=0.01; FIG. 28C). Infarct resorption was linearly related to both acute (r=0.53, p<0.001) and chronic iron volumes (r=0.52, p<0.001; FIG. 28D).

Figure 29A:
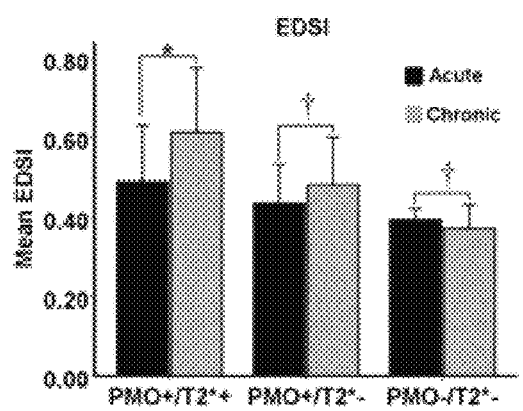
FIGS. 29A-29H depict, in accordance with various embodiments of the present invention, relationship between Iron Volume and LV Structural Remodeling in reperfused and non-reperfused myocardial infarctions. Mean EDSI from reperfused MIs (FIG. 29A) and non-reperfused MIs (FIG. 29E), as well as ΔEDSI from reperfused MIs (FIG. 29B) and non-reperfused MIs (FIG. 29F). *denotes statistically significant difference (p<0.05); and † denotes no statistically significant difference (p>0.05). Significant linear relationships between ΔEDSI and reperfused acute ($R^2=0.68$, p<0.001) and chronic reperfused infarct volumes ($R^2=0.53$, p<0.001) were observed (FIG. 29C). Similar observations were evident between ΔEDSI and non-reperfused acute ($R^2=0.73$, p<0.001) and chronic reperfused infarct volumes ($R^2=0.63$, p<0.001). Significant linear relationships between ΔEDSI and reperfused acute ($R^2=0.53$, p<0.001) and chronic reperfused iron volumes ($R^2=0.65$, p<0.001) were observed (FIG. 29D). Similar observations were evident between ΔEDSI and non-reperfused acute ($R^2=0.67$, p<0.001) and chronic reperfused infarct volumes ($R^2=0.65$, p<0.001).
Figure 29B:
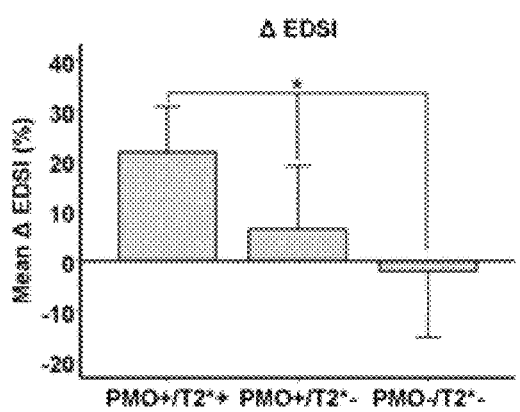
Figure 29C:
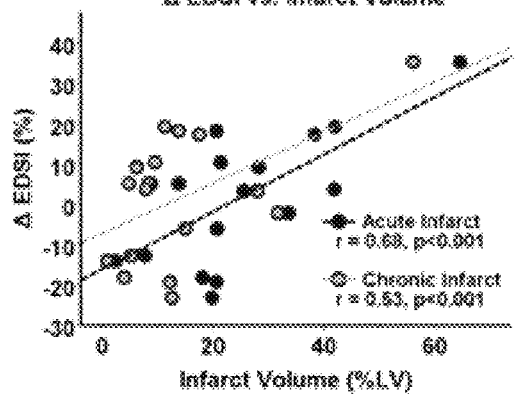
Figure 29D:
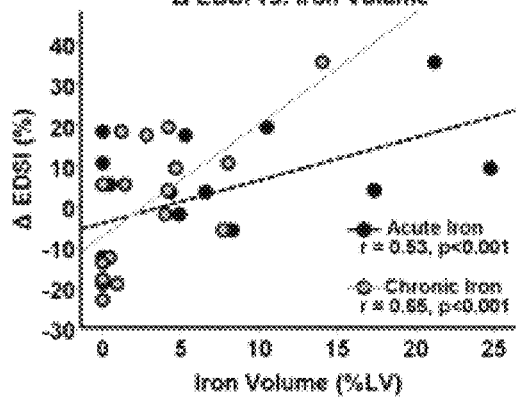

Iron within Chronic MI is Associated with Adverse Structural and Functional LV Remodeling A. Relationship Between Iron Volume and Structural LV Remodeling In the reperfused MIs, $PMO^+/T_2^{*+}$ group had significantly larger EDSI (FIG. 29A) compared to $PMO^+/T_2^{*-}$ and $PMO^-/T_2^{*-}$ groups in both acute and chronic phases (p=0.001 for acute EDSI between $PMO^+/T_2^{*+}$ and $PMO^+/T_2^{*-}$; p=0.01 for acute EDSI between $PMO^+/T_2^{*-}$ and $PMO^-/T_2^{*-}$; p<0.001 for acute EDSI between $PMO^+/T_2^{*+}$ and $PMO^-/T_2^{*-}$; p<0.001 for all comparisons in the chronic phase). The $PMO^+/T_2^{*+}$ group also had significantly larger EDSI (p=0.02) in the chronic phase compared to the acute phase. However, there was no significant difference in EDSI between the acute and chronic phases in both $PMO^+/T_2^{*-}$ (p=0.39) and $PMO^-/T_2^{*-}$ (p=0.65) groups. Compared to the $PMO^+/T_2^{*-}$ and $PMO^-/T_2^{*-}$ groups, $PMO^+/T_2^{*+}$ group had significantly higher ΔEDSI (FIG. 29 B) between the acute and chronic phases (p<0.001 for all comparisons). Linear regression analyses showed significant associations of ΔEDSI with both infarct and iron volumes measured at both acute and chronic phases (acute infarct: r=0.68, chronic infarct: r=0.53, FIG. 29C; acute iron: r=0.53, chronic iron: r=0.65, FIG. 29D; p<0.001 for all cases). Multivariate regression analyses showed that both infarct and iron volumes measured at both acute (infarct: β=2.02, p=0.002; iron: β=1.57, p=0.02) and chronic phases (infarct: β=3.46, p=0.003; iron: β=4.12, p<0.001) were significant and independent predictors of ΔEDSI.

Figure 29E:
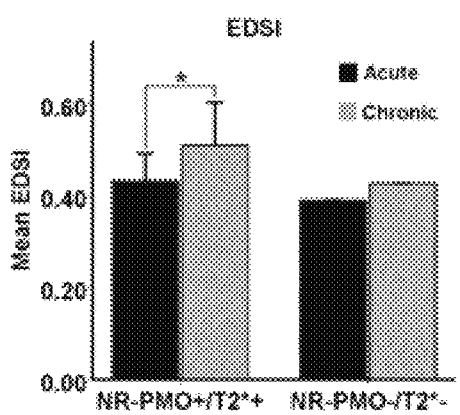
Figure 29F:
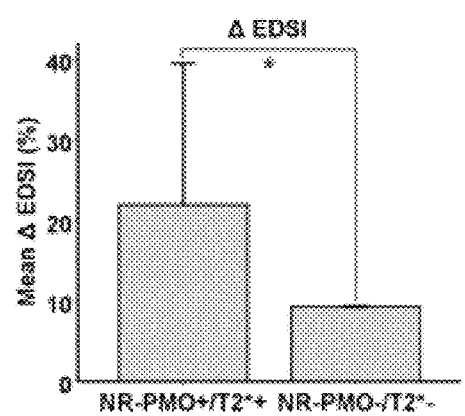
Figure 29G:
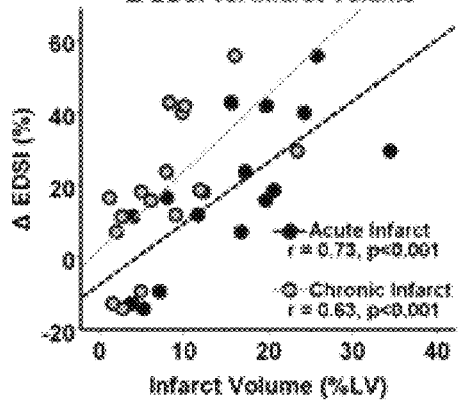
Figure 29H:
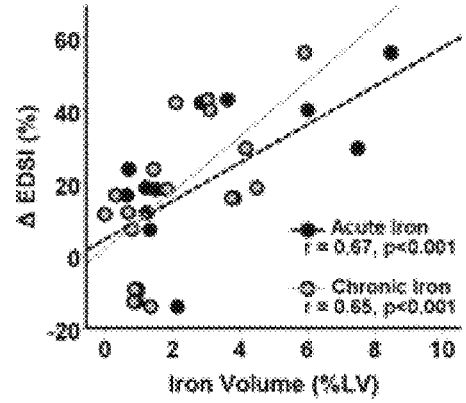

In the non-reperfused MIs, there was no significant difference in EDSI (p=0.56) between the $NR\text{-}PMO^+/T_2^{*+}$ and $NR\text{-}PMO^-/T_2^{*-}$ groups in the acute phase (FIG. 29E). In the chronic phase, canines in the $NR\text{-}PMO^+/T_2^{*+}$ group had significantly larger EDSI (p<0.001) compared to the control canine. The $NR\text{-}PMO^+/T_2^{*+}$ canines also had significantly larger EDSI (p=0.001) in the chronic phase compared to the acute phase (FIGS. 27A-27F). Compared to the $NR\text{-}PMO^-/T_2^{*-}$ canine, canines in the $NR\text{-}PMO^+/T_2^{*+}$ group had significantly higher ΔEDSI between the acute and chronic phases (p=0.01; FIG. 29F). Linear regression analyses showed significant associations of ΔEDSI with both infarct and iron volumes measured at both acute and chronic phases (acute infarct: r=0.73, chronic infarct: r=0.63, FIG. 29G; acute iron: r=0.67, chronic iron: r=0.65, FIG. 29H; p<0.001 for all cases). Multivariate regression analyses showed that both infarct and scar volumes measured at both acute (infarct: β=2.75, p=0.006; iron: β=1.64, p=0.01) and chronic phases (infarct: β=4.16, p=0.002; iron: β=4.81, p<0.001) were significant and independent predictors of ΔEDSI.

B. Relationship between Iron Volume and Functional LV Remodeling

In the reperfused MIs, canines in the $PMO^+/T_2^{*+}$ group had significantly larger EDV, larger ESV, and lower EF compared to the canines in the $PMO^+/T_2^{*-}$ and $PMO^-/T_2^{*-}$ groups in both acute and chronic phases (EDV and ESV: p<0.001 for all comparisons in both acute and chronic phases; EF: p<0.001 for all comparisons in the acute and chronic phases, except p=0.03 for chronic EF between $PMO^+/T_2^{*-}$ and $PMO^-/T_2^{*-}$; refer to Table 4). The $PMO^+/T_2^{*+}$ group also had significantly larger EDV (p=0.04), larger ESV (p=0.03), and lower EF (p=0.03) in the chronic phase compared to the acute phase. However, there was no significant difference in the functional remodeling parameters between the acute and chronic phases in the $PMO^+/T_2^{*-}$ (EDV: p=0.30, ESV: p=0.87, EF: p=0.81) and $PMO^-/T_2^{*-}$ (EDV: p=0.11, ESV: p=0.57, EF: p=0.98) groups. Compared to the canines in the $PMO^+/T_2^{*-}$ and $PMO^-/T_2^{*-}$ groups, canines in the $PMO^+/T_2^{*+}$ group had significantly higher ΔEDV, ΔESV, and ΔEF between the acute and chronic phases (ΔEDV and ΔESV: p<0.001 for all comparisons; ΔEF: p<0.001 for $PMO^+/T_2^{*+}$ vs. $PMO^+/T_2^{*-}$ and $PMO^+/T_2^{*+}$ vs. $PMO^-/T_2^{*-}$, p=0.98 for $PMO^+/T_2^{*-}$ vs. $PMO^-/T_2^{*-}$). Neither infarct volume nor iron volume measured at either acute or chronic phase could significantly predict ΔEDV, ΔESV, or ΔEF.

In the non-reperfused MIs, canines in the $NR\text{-}PMO^+/T_2^{*+}$ group had significantly larger EDV (p=0.002) and lower EF (p<0.001) to the $NR\text{-}PMO^-/T_2^{*-}$ canine in the acute phase (refer to Table 5). However, there was no significant difference in ESV (p=0.21) between the two groups in the acute phase. In the chronic phase, canines in the $NR\text{-}PMO^+/T_2^{*+}$ group had significantly larger EDV (p<0.001), larger ESV (p=0.01), and lower EF (p=0.002) compared to the control canine. The $NR\text{-}PMO^+/T_2^{*+}$ canines also had significantly larger EDV (p<0.001) and larger ESV (p=0.001) in the chronic phase compared to the acute phase. However, there was no significant difference in EF between the acute and chronic phases in the $NR\text{-}PMO^+/T_2^{*+}$ canines (EF: p=0.17). Compared to the $NR\text{-}PMO^-/T_2^{*-}$ canine, canines in the $NR\text{-}PMO^+/T_2^{*+}$ group had significantly higher ΔEDV and ΔESV between the acute and chronic phases (ΔEDV: p<0.001; ΔESV: p=0.001). However, ΔEF in the $PMO^+/T_2^{*+}$ group was not significantly different than that of the control canine (p=0.60). Neither infarct volume nor iron volume measured at either acute or chronic phase could significantly predict ΔEDV, ΔESV, or ΔEF.

MO is a well-known marker of ischemia-reperfusion injury, but the underlying mechanisms by which it leads to adverse effects in the long-term well beyond its resolution are not well understood. In this study, we have shown that PMO, with or without reperfusion hemorrhage can lead to significant chronic iron deposition within the infarcted territories, and the extent of chronic iron deposition is strongly related to the extent of PMO observed in the acute phase. In canines with reperfused MIs, we have shown that although PMO may not always be associated with reperfusion hemorrhage as seen on T2*-weighted images in the acute phase, it can still resolve into iron deposition within the infarcted territories in the chronic phase. This was further validated by the occurrence of significant chronic iron deposition within non-reperfused MIs, which are classically known to not have any reperfusion hemorrhage. We have also shown that the chronic iron deposition post-PMO resolution is a significant and independent predictor of adverse LV remodeling on the basis of end-diastolic sphericity index in the chronic phase. Significant pro-inflammatory burden was also found to be associated with the chronic iron deposition.

Iron Deposits within Reperfused and Non-Reperfused Chronic MI

Recent studies in canines and patients with healed MIs have shown that acute reperfusion hemorrhage resolves into iron deposits within the infarcted tissue up to several months post-reperfusion. However, the possibility of chronic iron deposition in the presence of PMO alone without any concurrent reperfusion hemorrhage has not been previously investigated. The mechanisms by which PMO leads to chronic iron deposition remain to be investigated. One possible mechanism could be that the stagnant blood within the blocked 'no-reflow' microvasculature could gradually degrade. The eventual breakdown of the no-reflow microvasculature can externalize the degraded stagnant blood into the scar tissue and manifest itself as iron deposits.

The occurrence of chronic iron deposition within non-reperfused MIs has also not been shown previously in the literature. It has shown that PMO, defined as hypointense cores on LGE images, is equally prevalent in patients with non-reperfused MIs as in reperfused MIs. While the PMO observed in reperfused MIs is attributed to plugging of microvasculature by inflammatory cells, erythrocytes and other microembolic debris, the pathological mechanism of PMO observed in non-reperfused MIs could be due to permanently occluded coronary artery that has not been reperfused. However, the mechanism of iron deposition in non-reperfused MIs could be still similar to that observed in reperfused MIs. The permanently ligated vasculature is expected to eventually degrade and the stagnant blood and blood-degradation products within it can be externalized into the scar tissue, which manifest as chronic iron deposits. Our results suggest that chronic iron deposition is a fingerprint of PMO observed in the acute phase, and could be a mechanism through which PMO exerts adverse effects in the long-term.

Crystallized Ferric Iron Deposits and Inflammation

TEM, atomic resolution scanning TEM, and EDS studies showed for the first time that the iron deposits within chronic MI are found as nodules (likely holoferritin) composed from nanocrystals of iron in ferric form. Moreover, the TEM images also showed that iron composites are enclosed by membranous organelles that appear to be loaded to their physical limits (diameter >1 µm). These findings, along with evidence from previous studies, may help to explain the proinflammatory burden in chronic MI with iron deposits.

Lysosomes are membrane bound spherical organelles, which are rich in hydrolytic enzymes and are typically less than 1 µm in diameter. Disruption of these membranes, due to excessive uptake of hard/sharp crystalline material similar to iron deposits we characterized here, is known to be a key contributor to several inflammatory disease processes. Several studies have shown that such disruptions can set forth cascading inflammatory responses leading to up regulation of proinflammatory cytokines (IL-1β and TNF-α). Given our observations that the extent of inflammatory cytokines were closely related to extent of iron burden (FIGS. 27A-27F), in light of prior studies in the literature, it appears that that iron overloading within the macrophages may be a key mechanism by which the inflammatory response is perpetuated within chronic infarctions with a prior history of PMO. In addition, it is also know that ferric iron catalyzes Fenton reactions to produce reactive oxygen species, which are known to impart oxidative stress throughout the myocardium. Without wishing to be bound by any particular theory, we believe that the ferric iron deposits within the chronic MI may mediate distress on the healthy myocardium.

Proinflammatory Burden and Adverse Remodeling

Chronic iron deposition within reperfused MIs has been previously implicated in adverse LV remodeling and arrhythmogenesis in healed MIs. In line with previous observations, our study has shown that iron deposition post-PMO resolution is a strong predictor of LV structural remodeling. The role of iron in the onset of adverse LV remodeling and heart failure is well documented in non-ischemic iron-overload cardiomyopathies. Regarding the exact mechanism by which iron deposition post-PMO resolution in MIs mediates adverse LV remodeling, active and prolonged pro-inflammatory activity co-localized with iron deposits with chronic infarctions observed in this study may be one mechanism. In this study, we observed significant co-localization of Mac387+ cells with post-PMO iron deposition in the chronic infarcted territories, which is similar to earlier observations in chronic reperfused MIs that sustained acute reperfusion hemorrhage. We have also found that the extent of iron deposition is directly proportional to the extent of Mac387+ co-localization. The monoclonal antibody Mac387 is specific calgranulin, a protein expressed by newly-recruited monocytes and is significantly downregulated when they mature to macrophages. It has been shown that the number of Mac387+ cells in the infarcted myocardium was significantly reduced at 7 days post-reperfusion, and this marker can be used an index for new recruitment of leukocytes in the heart. Our finding of the presence of Mac387+ cells to be highly co-localized with iron and iron scavenger receptor CD163 in this study shows an active and prolonged iron-driven inflammatory process within chronic infarcts that extends well beyond the acute inflammatory stage. The interaction of Mac387+ cells with post-PMO iron remains to be investigated, but since CD163 is a key marker of iron-induced macrophage activation, iron phagocytosis and clearance seem to be the plausible explanations. It was previously shown that iron-oxide particles from ferumoxide labeled stem cells are internalized by macrophages. The role of monocyte-derived macrophages in iron phagocytosis is also well known in other pathologies such as atherosclerotic plaques and in the liver.

A number of pro-inflammatory cytokines, which have been implicated in the development of LV dysfunction and LV remodeling dysfunction, are known to be released when monocytes mature into macrophages. We found that Mac387+ cells are associated with significant IL-1β, TNF-α and MMP-9 activities. TNF-α is a well-known potent proinflammatory cytokine implicated in development of LV dysfunction, LV remodeling and endothelial dysfunction. MMP-9 activity is well known to be associated with extracellular matrix degradation and modulating mechanical architecture of the scar. Interleukin-1β has been shown to promote matrix degradation by enhancing MMP synthesis while reducing collagen deposition and has emerged as an important therapeutic target in the chronic phase post-MI. These results suggest that the macrophages derived from Mac387+ cells are in an unrestrained pro-inflammatory M1 activation state that can potentially worsen LV remodeling.

Recent studies have been instrumental in shedding light on the relation between MO and inflammation. These studies have shown that in cases of reperfused MIs with MO, monocyte recruitment is delayed in the acute and sub-acute period; and, in cases where erythrocyte extravasation (hemorrhage) accompanies MO, iron accumulates within the MI territories in the chronic phase and is site of intense macrophage recruitment. Although adequate inflammatory activity is necessary for wound healing, long-term persistence of inflammation is detrimental to the reparative effects. Mechanistically, the extent of LV remodeling in the post-MI period is related to the timely inhibition and resolution of the inflammatory activity. In particular, prolonged inflammation has been shown to impair collagen deposition and scar formation resulting in reduced tensile strength and LV dilatation. Early studies suggest that ineffective suppression of inflammation post-MI is associated with adverse LV remodeling of the heart. The finding that iron deposits within chronic MI plays an intermediary role in wound healing may be of substantial clinical relevance as it can unravel how PMO imparts adverse long-term effects on the infarcted heart and underscore iron as a therapeutic target in post-infarction heart failure.

Supported by extensive histopathology, we have used T2*-weighted CMR in our study to validate the occurrence of acute reperfusion hemorrhage and chronic iron deposition within infarcted tissue. T2* CMR has been previously validated in several studies to be a highly sensitive technique for the detection of both acute hemorrhage (see e.g., O'Regan D P, Ariff B, Neuwirth C, Tan Y, Durighel G, Cook S A. Assessment of severe reperfusion injury with T2* cardiac MRI in patients with acute myocardial infarction. Heart 2010; 96:1885-91.; Kali A, Tang R L, Kumar A, Min J K, Dharmakumar R. Detection of acute reperfusion myocardial hemorrhage with cardiac MR imaging: T2 versus T2. Radiology 2013; 269:387-95; and Kumar A, Green J D, Sykes J M et al. Detection and quantification of myocardial reperfusion hemorrhage using T2*-weighted CMR. JACC Cardiovasc Imaging 2011; 4:1274-83.) and chronic iron deposition in MIs (see e.g., Kali A, Kumar A, Cokic I et al. Chronic manifestation of postreperfusion intramyocardial hemorrhage as regional iron deposition: a cardiovascular magnetic resonance study with ex vivo validation. Circ Cardiovasc Imaging 2013; 6:218-28.). However, T2*-weighted CMR is also susceptible to off-resonance artifacts in the infero-lateral LV wall, which become highly pronounced at high magnetic field strengths, such as at 3 T. These off-resonance artifacts can be potentially misinterpreted as hemorrhage or chronic iron. For this reason, we have limited our analysis to LAD infarctions, as the anteroseptal LV wall is less prone to off-resonance artifacts. To minimize the off-resonance artifacts, we performed careful volume-selective shimming and short TEs. With the aid of LGE imaging, hemorrhage and chronic iron can still be adequately differentiated from off-resonance artifacts, as these two pathological features are always confined to the infarcted territories. Moreover, blooming effect from hemorrhage and chronic iron originate from the endocardium, while off-resonance artifacts originate from epicardium.

We observed a clear relationship of EDSI with infarct and iron volumes, which suggests that longer follow ups (e.g. 6 months) may have lead to worse functional LV remodeling in animals with iron deposits. While we analyzed LAD infarctions, the observations could be valid regardless of the culprit coronary artery.

CONCLUSION

Territories of persistent microvascular obstructions in the acute phase of MI, with or without reperfusion hemorrhage, resolve into iron oxide nanocrystals in ferric state in the chronic phase of MI. The amount of iron deposition is determined by the extent of persistent microvascular obstruction and is directly related to the extent of pro-inflammatory burden, infarct thinning and adverse LV remodeling. Post-resolution of persistent microvascular obstruction into iron could be a potential contributing source to the adverse remodeling of the heart in the chronic phase of MI.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method for treating a subject with myocardial infarction, comprising:
   administering to the subject an effective amount of a composition comprising a chelating agent, at least in chronic phase of the myocardial infarction, based on knowledge of an increase in iron oxide deposition in the chronic phase in the infarcted region relative to a remote region following reperfusion hemorrhage,
   wherein the subject has undergone reperfusion following the myocardial infarction, the subject has hemorrhage in the myocardial infarct, and
   the subject has been detected to have an increase in iron oxide deposition in a hemorrhagic infarcted region of the subject's heart relative to the remote region of the subject's heart.

2. The method of claim 1, further comprising administering an effective amount of one or more of an anti-inflammatory agent, a lipid-lowering agent, a carbon monoxide therapy, a heme-oxygenase regulating drug, and an agent capable of promoting heart blood flow.

3. The method of claim 1, wherein the subject is a patient with ischemic heart disease.

4. The method of claim 1, further comprising imaging the subject's heart after the administration of the composition to detect a subsequent level of iron or deposits that contain iron in an infarcted region relative to the remote region.

5. The method of claim 4, further comprising administering to the subject a subsequent dose of a chelating agent if a higher level of iron or deposits that contain iron is indicated in the infarcted region relative to a remote region, or discontinuing administration of the chelating agent if the level of iron or deposits that contain iron is not indicated as higher in the infarcted region relative to the remote region.

6. The method of claim 1, further comprising diagnosing the hemorrhage in the myocardial infarct in the subject prior to the administration of the composition to the subject.

7. The method of claim 1, further comprising selecting a subject having the hemorrhage in the myocardial infarct for the treatment based on imaging of the subject's heart, before the administration of the composition to the subject.

8. The method of claim 1, further comprising measuring blood levels of any one or more of hepcidin, carbon monoxide, bilirubin, unbound iron, Fe bound to transferrin, ferritin, heme (heam) oxgenase, and biliverdin in the subject, wherein an increase in the hepcidin, the biliverdin, the bilirubin, the carbon monoxide, the heme (haem) oxygenase, the Fe bound to transferrin, the ferritin and/or a decrease in the UIBC indicates the subject has the hemorrhage in the myocardial infarct.

9. The method of claim 1, wherein the chelating agent comprises Deferoxamine, Deferasirox, Deferiprone, or a combination thereof.

10. The method of claim 1, wherein the administration at least in the chronic phase comprises administering from 10 days to 15 days, from 15 days to 20 days, from 20 days to 25 days, from 25 days to 30 days, or from 56 days to 6 months following the onset of the myocardial infarction.

11. The method of claim 4, wherein the imaging is performed with cardiac magnetic resonance (CMR) imaging, T2* CMR, chemical shift-encoded T2* CMR, T2 CMR, Ti CMR, T1ρ CMR, late-gadolinium enhancement CMR (LGE-CMR), cine CMR, single-photon emission computed tomography (SPECT), positron emission tomography (PET), computed tomography (CT), or a combination thereof.

12. The method of claim 4, wherein the imaging is cardiac magnetic resonance imaging obtained from 5-10 days, 10-15 days, 15-20 days, 20-25 days, 25-30 days, or from 56 days to 6 months, following the onset of the myocardial infarction.

13. A method of treating a subject with microvascular obstructions (MO) or tissue necrosis in the heart, comprising:
 administering to the subject an effective amount of a composition comprising a chelating agent and one or more of an anti-inflammatory agent, a lipid-lowering agent, a carbon monoxide therapy, a heme-oxygenase regulating drug, and an agent capable of promoting heart blood flow in chronic phase of a myocardial infarction, wherein the subject has been diagnosed with the MO or tissue necrosis in the heart.

14. The method of claim 13, wherein the MO is diagnosed based on imaging the subject's heart and identifying the MO in the heart's myocardial tissue, non-myocardial tissue, myocardium, endocardium, epicardium, pericardium, valvular tissue, non-valvular tissue, pulmonary valve, tricuspid valve, mitral valve, aortic valve, blood vessel, coronary blood vessel, non-coronary blood vessel, coronary artery, cardiac vein, superior vena cava, inferior vena cava, pulmonary trunk, pulmonary artery, pulmonary vein, right pulmonary vein, left pulmonary vein, or aorta, or a combination thereof.

15. The method of claim 13, wherein the subject has or has had myocardial infarction, and the MO or tissue necrosis is diagnosed in an infarcted region, non-infarcted region, or both.

16. The method of claim 13, wherein the chelating agent comprises deferoxamine, deferasirox, or deferiprone, or a combination thereof; the anti-inflammatory agent comprises a corticosteroid, nonsteroidal anti-inflammatory drug (NSAID), anti-IL-1beta, anti-TNF-α, anti-IL-6, anti-MMP, macrophage modulators, phosphatidylserine-presenting liposomes, NLRP3 inflammasome inhibitor, 16673-34-0 (5-chloro-2-methoxy-N-[2-(4-sulfamoylphenyl)ethyl]benzamide)), inflammasome antagonists, anti-diabetic medication, insulin, metformin, sulfonylureas, thiazolidinediones, dipeptidyl peptidase-4 inhibitors, SGLT2 inhibitors, glucagon-like peptide-1 analog, or a combination thereof; the lipid-lowering agent is a statin, cholesterol absorption inhibitors, bile-acid-binding resins/sequestrants, niacin, vitamin B3, or a combination of; and/or the agent capable of promoting heart blood flow comprises a coronary vasodilator.

17. A method of treating a subject having had myocardial infarction (MI) and undergone reperfusion, or who has microvascular obstructions (MO) or tissue necrosis in the heart, comprising:
 administering to the subject an effective amount of a composition from 10 days to 15 days, from 15 days to 20 days, from 20 days to 25 days, from 25 days to 30 days, or from 56 days to 6 months since the onset of the MI, the MO or the tissue necrosis,
 wherein the composition comprises a chelating agent and one or more of an anti-inflammatory agent, a lipid-lowering agent, a carbon monoxide therapy, a heme-oxygenase regulating drug, and an agent capable of promoting heart blood flow.

18. The method of claim 17, wherein the subject is identified as having an elevated level of iron or deposits that contain iron in the infarcted region relative to a remote region of the heart in chronic phase of the MI and/or as having the MO in the heart in acute phase of the MI.

* * * * *